US008378340B2

(12) United States Patent
Kobayashi et al.

(10) Patent No.: US 8,378,340 B2
(45) Date of Patent: Feb. 19, 2013

(54) AROMATIC COMPOUND

(75) Inventors: Satoshi Kobayashi, Tsukuba (JP); Satoshi Mikami, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/487,405

(22) Filed: Jun. 4, 2012

(65) Prior Publication Data

US 2012/0238765 A1   Sep. 20, 2012

Related U.S. Application Data

(62) Division of application No. 12/815,964, filed on Jun. 15, 2010, now Pat. No. 8,222,426, which is a division of application No. 10/574,563, filed as application No. PCT/JP2004/015001 on Oct. 5, 2004, now Pat. No. 7,842,941.

(30) Foreign Application Priority Data

Oct. 6, 2003 (JP) .................................. 2003-346688

(51) Int. Cl.
   H01L 35/24    (2006.01)
   C07D 333/76   (2006.01)
(52) U.S. Cl. ........................................... 257/40; 549/46
(58) Field of Classification Search .................... 549/46; 257/40
   See application file for complete search history.

(56) References Cited

U.S. PATENT DOCUMENTS

| 3,136,782 | A | 6/1964 | Bimber et al. |
| 3,929,832 | A | 12/1975 | Sicree et al. |
| 5,833,994 | A | 11/1998 | Wheelock et al. |
| 6,022,307 | A | 2/2000 | Salvati et al. |
| 6,168,838 | B1 | 1/2001 | Schmidt et al. |
| 6,329,082 | B1 | 12/2001 | Kreuder et al. |
| 2001/0053842 | A1 | 12/2001 | Woo et al. |
| 2002/0051895 | A1 | 5/2002 | Cho et al. |
| 2004/0002576 | A1 | 1/2004 | Oguma et al. |
| 2004/0124399 | A1 | 7/2004 | Schmidt et al. |
| 2004/0253389 | A1 | 12/2004 | Suzuki et al. |
| 2005/0042195 | A1 | 2/2005 | Kobayashi et al. |
| 2005/0170202 | A1 | 8/2005 | Tamao et al. |
| 2008/0138651 | A1 | 6/2008 | Doi et al. |

FOREIGN PATENT DOCUMENTS

| EP | 1223209 A1 | 7/2002 |
| EP | 1 344 788 A1 | 9/2003 |
| JP | 01-229262 A | 9/1989 |
| JP | 02-146049 A | 6/1990 |
| JP | 2002-161130 A | 6/2002 |
| JP | 2004-083481 A | 3/2004 |
| WO | 98/27035 A1 | 6/1998 |
| WO | 98/27043 A1 | 6/1998 |
| WO | 98/30213 A2 | 7/1998 |
| WO | 02/055463 A1 | 7/2002 |
| WO | 2004/039859 A1 | 5/2004 |
| WO | WO 2004039859 A1 * | 5/2004 |

OTHER PUBLICATIONS

English translation of Office Action issued Jun. 28, 2011 in Japanese Patent Application No. 2004-292337.
K. Sielex et al., "Prediction of gas chromatographic retention indices of polychlorinated dibenzothiophenes on non-polar columns", Journal of Chromatography, A, 866 (2000), pp. 105-120.
R. Weber et al., "Mechanism of the Formation of Polychlorinated Dibenzo-p-dioxins and Dibenzofurans from Chlorophenols in Gas Phase Reactions," Chemophere. vol. 38, pp. 529-549, 1999.
L. T. Burka et al., "Identification of the Biliary Metabolites of 2,3,7,8-Tetrachlorodibenzofuran in the Rat", Chemosphere, vol. 21, Nos. 10-11, pp. 1231-1242, 1990.
L. T. Burka et al., "Synthesis of Possible Metabolites of 2,3,7,8-Tetrachlorodibenzofuran", J. Agric. Food Chem. 1989, 37, pp. 1528-1532.
H. Kuroki et al., "Synthesis and Mass Spectral Properties of Polychlorinated Dibenzofuran (PCDF) Metabolites", Chemosphere, vol. 16, Nos. 8/9, pp. 1641-1647, 1987.
A. Norstrom et al., "Synthesis of Chlorinated Dibenzofurans and Chlorinated Amino-Dibenzofurans from the Corresponding Diphenyl Ethers and Nitro-Diphenylethers", Chemosphere, No. 6, pp. 331-343, 1979.

(Continued)

Primary Examiner — Joseph Kosack
(74) Attorney, Agent, or Firm — Sughrue Mion, PLLC

(57) ABSTRACT

An aromatic compound of the following formula (1), (2), (5) or (6),

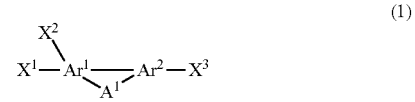 (1)

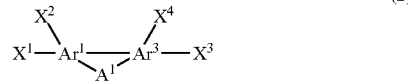

(2)

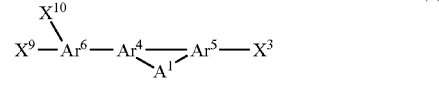

(5)

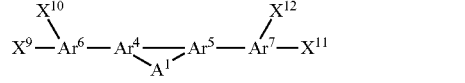

(6)

wherein, $Ar^1$ and $Ar^3$ represent a tetra-valent aromatic hydrocarbon group or a tetra-valent heterocyclic group, and $Ar^2$, $Ar^4$, $Ar^5$, $Ar^6$ and $Ar^7$ represent a tri-valent aromatic hydrocarbon group or a tri-valent heterocyclic group, $A^1$ represents $-Z^1-$, $-Z^2-Z^3-$ or $-Z^4=Z^5-$, wherein $Z^1$, $Z^2$ and $Z^3$ represent O, S or the like and $Z^4$ and $Z^5$ represent N, B, P or the like, $X^1$, $X^2$, $X^3$, $X^4$, $X^9$, $X^{10}$, $X^{11}$, and $X^{12}$ represent a halogen atom or the like.

1 Claim, No Drawings

OTHER PUBLICATIONS

H. Shah et al., "Synthesis and Opto-Electronic Properties of Polynaphthalenes From Bis-Ortho-Diynylarenes", Polymeric Materials Science and Engineering, 1999, vol. 80, p. 199.

H. Pan et al., "Diphenimides. 2.1a,b Some Ring Substituted N-2-Fluorenyl-2',2"—Diphenamic Acids and Diphenimides. Derivatives of Fluorene. XXXII.1c", Journal of Medicinal Chemistry, 1970, vol. 13, No. 3, pp. 567-568.

S. Lee et al., "Sterically Hindered Fluorenyl-Substituted Poly(p-phenylenevinylenes) for Light-Emitting Diodes", Macromolecules, 2002, vol. 35, No. 4, pp. 1356-1364.

Office Action issued on Jan. 11, 2011 from Japan Patent Office in Japanese Application No. 2004-292337.

* cited by examiner

AROMATIC COMPOUND

CROSS REFERENCE TO RELATED APPLICATIONS

This application is a divisional application of U.S. application Ser. No. 12/815,964 filed Jun. 15, 2010, which is a divisional application of U.S. application Ser. No. 10/574,563 filed Apr. 4, 2006, now U.S. Pat. No. 7,842,941, which is a National Stage of PCT/JP04/015001 filed Oct. 5, 2004, which claims benefit of Japanese Application No. 2003-346688 filed Oct. 6, 2003. The entire disclosures of the prior applications are hereby incorporated by reference.

TECHNICAL FIELD

The present invention relates to an aromatic compound having three or four condensation-reactive functional groups or their precursors which can be used as a raw material monomer for a branched polymer compound.

BACKGROUND ART

Light emitting materials of higher molecular weight (light emitting polymer) are soluble in a solvent and capable of forming a light emitting layer in a light emitting device by an application method unlike those of lower molecular weight, and thus, light emitting polymers are variously investigated and those containing an aromatic ring in the main chain are known.

As monomers for producing these light emitting polymers, aromatic compounds having two condensation-reactive functional groups (for example, WO97/05184, and the like) are used.

On the other hand, there has been recently conducted a trial of making a branched polymer compound for improving the performance of a light emitting polymer and the like, and aromatic compounds having three condensation-reactive functional groups which can be used as monomers of the compound are disclosed (for example, WO96/17035). However, for producing various branched polymer compounds, their kinds are not sufficient.

DISCLOSURE OF THE INVENTION

The present invention has an object of providing a novel aromatic compound having three or four condensation-reactive functional groups or their precursors.

That is, the present invention provides a compound of the following formula (1) or formula (2):

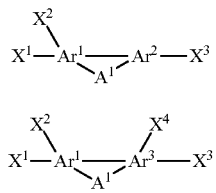

wherein, $Ar^1$ and $Ar^3$ each independently represent a tetra-valent aromatic hydrocarbon group or a tetra-valent heterocyclic group. $Ar^2$ represents a tri-valent aromatic hydrocarbon group or a tri-valent heterocyclic group, $Ar^1$, $Ar^2$ and $Ar^3$ may have a substituent, and when $Ar^1$ and $Ar^3$ have a substituent, these may be connected to form a ring and when $Ar^1$ and $Ar^3$ have a substituent, these may be connected to form a ring.

$A^1$ represents $-Z^1-$, $-Z^2-Z^3-$ or $-Z^4=Z^5-$, $Z^1$, $Z^2$ and $Z^3$ each independently represent O, S, C(=O), S(=O), $SO_2$, $C(R^1)(R^2)$, $Si(R^3)(R^4)$, $N(R^5)$, $B(R^6)$, $P(R^7)$ or $P(=O)(R^8)$, and $Z^4$ and $Z^5$ each independently represent N, B, P, $C(R^9)$ or $Si(R^{10})$.

(wherein, $R^1$, $R^2$, $R^3$, $R^4$, $R^5$, $R^6$, $R^7$, $R^8$, $R^9$ and $R^{10}$ each independently represent a hydrogen atom, halogen atom, alkyl group, alkyloxy group, alkylthio group, aryl group, aryloxy group, arylthio group, arylalkyl group, arylalkyloxy group, arylalkylthio group, acyl group, acyloxy group, amide group, acid imide group, imine residue, amino group, substituted amino group, substituted silyl group, substituted silyloxy group, substituted silylthio group, substituted silylamino group, mono-valent heterocyclic group, heteroaryloxy group, heteroarylthio group, arylalkenyl group, arylethynyl group, carboxyl group, alkyloxycarbonyl group, aryloxycarbonyl group, arylalkyloxycarbonyl group, heteroaryloxycarbonyl group or cyano group. Here, $R^1$, $R^2$, $R^3$ and $R^4$ may be mutually connected to form a ring).

In formula (1), $Ar^2$ and $A^1$ are connected to mutually adjacent atoms on $Ar^1$ ring and $Ar^1$ and $A^1$ are connected to mutually adjacent atoms on $Ar^2$ ring, and in formula (2), $Ar^3$ and $A^1$ are connected to mutually adjacent atoms on $Ar^1$ ring and $Ar^1$ and $A^1$ are connected to mutually adjacent atoms on $Ar^3$ ring.

$X^1$, $X^2$, $X^3$ and $X^4$ each independently represent a halogen atom, alkylsulfonate group, arylsulfonate group, arylalkylsulfonate group, boric ester group group, $-B(OH)_2$, methyl monohalide group, sulfonium methyl group, phosphonium methyl group, phosphonate methyl group, cyanomethyl group, formyl group, vinyl group, hydroxyl group, alkyloxy group, acyloxy group, substituted silyloxy group, amino group or nitro group, and at least one of $X^1$, $X^2$ and $X^3$ in formula (1) and at least one of $X^1$, $X^2$, $X^3$ and $X^4$ in formula (2) are selected from a halogen atom, alkylsulfonate group, arylsulfonate group, arylalkylsulfonate group, boric ester group group, $-B(OH)_2$, methyl monohalide group, sulfonium methyl group, phosphonium methyl group, phosphonate methyl group, cyanomethyl group, formyl group and vinyl group).

Further, the present invention provides a compound of the following formula (5) or formula (6):

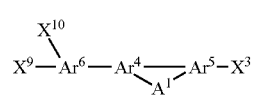

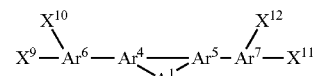

(wherein, $A^1$ and $X^3$ represent the same meaning as described above, $Ar^4$, $Ar^5$, $Ar^6$ and $Ar^7$ each independently represent a tri-valent aromatic hydrocarbon group or a tri-valent heterocyclic group, $Ar^4$, $Ar^5$, $Ar^6$ and $Ar^7$ may have a substituent, and when $Ar^4$ and $Ar^5$ have a substituent, these may be connected to form a ring.

$X^9$, $X^{10}$, $X^{11}$ and $X^{12}$ each independently represent a halogen atom, alkylsulfonate group, arylsulfonate group, arylalkylsulfonate group, boric ester group group, $-B(OH)_2$, methyl monohalide group, sulfonium methyl group, phosphonium methyl group, phosphonate methyl group, cyanomethyl group, formyl group, vinyl group, hydroxyl group, alkyloxy group, acyloxy group, substituted silyloxy group, amino group or nitro group, and at least one of $X^9$, $X^{10}$ and $X^3$ in formula (5) and at least one of $X^9$, $X^{10}$, $X^{11}$ and $X^{12}$ in formula (6) represent a halogen atom, alkylsulfonate group, arylsulfonate group, arylalkylsulfonate group, boric ester group group, —B(OH)$_2$, methyl monohalide group, sulfonium methyl group, phosphonium methyl group, phosphonate methyl group, cyanomethyl group, formyl group or vinyl group.)

Still further, the present invention provides a compound of the following formula (9), (10) or (11):

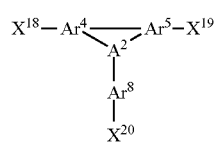

(9)

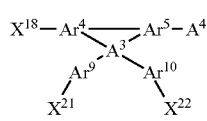

(10)

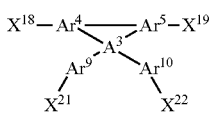

(11)

(wherein, $Ar^4$ and $Ar^5$ represent the same meaning as described above, $Ar^8$, $Ar^9$ and $Ar^{10}$ each independently represent an arylene group or a di-valent heterocyclic group, $Ar^4$, $Ar^5$, $Ar^8$, $Ar^9$ and $Ar^{10}$ may have a substituent, and when $Ar^4$ and $Ar^5$ have a substituent, these may be connected to form a ring, when $Ar^9$ and $Ar^{10}$ have a substituent, these may be connected to form a ring and when $Ar^9$ and $Ar^{10}$ have a substituent, these may be connected to form a ring.

$A^2$ represents any of the following formulae:

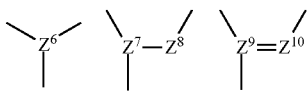

wherein, $Z^6$ represents B, P or P(=O), $Z^7$ represents C(R$^9$), Si(R$^{10}$), N, B, P or P(=O), $Z^8$ represents O, S, C(=O), S(=O), SO$_2$, C(R$^1$)(R$^2$) Si(R$^3$)(R$^4$), N(R$^5$), B(R$^6$), P(R$^7$) or P(=O)(R$^8$), $Z^9$ represents C or Si, $Z^{10}$, represents N, B, P, C(R$^9$) or Si(R$^{10}$). (wherein, R$^1$, R$^2$, R$^3$, R$^4$, R$^5$, R$^6$, R$^7$, R$^8$, R$^9$ and R$^{10}$ represent the same meaning as described above), $A^3$ represents any of the following formulae:

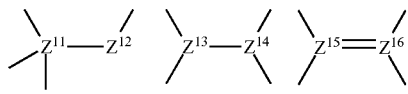

wherein, $Z^{11}$ represents C or Si, $Z^{12}$ represents O, S, C(=O), S(=O), SO$_2$, C(R$^1$)(R$^2$), Si(R$^3$)(R$^4$), N(R$^5$), B(R$^6$), P(R$^7$) or P(=O) (R$^8$), $Z^{13}$ and $Z^{14}$ each independently represent C(R$^9$), Si(R$^{10}$), B, N, P or P(=O). $Z^{15}$ and $Z^{16}$ each independently represent C or Si. (wherein, R$^1$, R$^2$, R$^3$, R$^4$, R$^5$, R$^6$, R$^7$, R$^8$, R$^9$ and R$^{10}$ represent the same meaning as described above).

$A^4$ represents a halogen atom, alkyl group, alkyloxy group, alkylthio group, aryl group, aryloxy group, arylthio group, arylalkyl group, arylalkyloxy group, arylalkylthio group, substituted amino group, substituted silyl group, mono-valent heterocyclic group, hetero aryloxy group, hetero arylthio group, arylalkenyl group or arylethynyl group. In formula (9), $Ar^5$ and $A^2$ are connected to mutually adjacent atoms on $Ar^4$ ring and $Ar^4$ and $A^2$ are connected to mutually adjacent atoms on $Ar^5$ ring.

$X^{18}$, $X^{19}$, $X^{20}$, $X^{21}$ and $X^{22}$ each independently represent a halogen atom, alkylsulfonate group, arylsulfonate group, arylalkylsulfonate group, boric ester group group, —B(OH)$_2$, methyl monohalide group, sulfonium methyl group, phosphonium methyl group, phosphonate methyl group, cyanomethyl group, formyl group, vinyl group, hydroxyl group, alkyloxy group, acyloxy group, substituted silyloxy group, amino group or nitro group, and at least one of $X^{18}$, $X^{19}$ and $X^{20}$ in formula (9), at least one of $X^{18}$, $X^{21}$ and $X^{22}$ in formula (10) and at least one of $X^{18}$, $X^{19}$, $X^{21}$ and $X^{22}$ in formula (11) represent a halogen atom, alkylsulfonate group, arylsulfonate group, arylalkylsulfonate group, boric ester group group, —B(OH)$_2$, methyl monohalide group, sulfonium methyl group, phosphonium methyl group, phosphonate methyl group, cyanomethyl group, formyl group or vinyl group).

Also, the present invention provides a compound of the following formula (15):

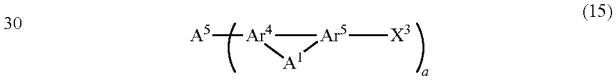

(15)

(wherein, $Ar^4$, $Ar^5$, $A^1$ and $X^3$ represent the same meaning as described above. $A^5$ represents a boron atom, aluminum atom, gallium atom, silicon atom, germanium atom, nitrogen atom, phosphorus atom, arsenic atom, a-valent aromatic hydrocarbon group, a-valent heterocyclic group or a-valent group having a metal complex structure. a represents 3 or 4. A plurality of $Ar^4$s, $Ar^5$s, $A^1$s and $X^{10}$s may be mutually the same or different).

BEST MODES FOR CARRYING OUT THE INVENTION

In the compounds of the above formulae (1) and (2), $Ar^1$ and $Ar^3$ each independently represent a tetra-valent aromatic hydrocarbon group or a tetra-valent heterocyclic group. $Ar^2$ represents a tri-valent aromatic hydrocarbon group or a tri-valent heterocyclic group, $Ar^1$, $Ar^2$ and $Ar^3$ may have a substituent, and when $Ar^1$ and $Ar^2$ have a substituent, these may be connected to form a ring and when $Ar^1$ and $Ar^3$ have a substituent, these may be connected to form a ring.

The trivalent aromatic hydrocarbon group and tetravalent aromatic hydrocarbon group mean groups in which 3 and 4 hydrogens are removed respectively from aromatic hydrocarbon compounds, and usually have 6 to 60 carbon atoms, preferably 6 to 20 carbon atoms. They may carry a substituent on the aromatic hydrocarbon groups, but the number of carbon atoms of the substituent is not counted as the number of carbon atoms of the aromatic hydrocarbon group. Examples of the substituent include an alkyl group, alkyloxy group, alkylthio group, aryl group, aryloxy group, arylthio group, arylalkyl group, arylalkyloxy group, arylalkylthio group, acyl group, acyloxy group, amide group, acid imide group, imine residue, amino group, substituted amino group, substituted silyl group, substituted silyloxy group, substituted silylthio group, substituted silylamino group, monovalent heterocyclic group, hetero aryloxy group, hetero arylthio group, arylalkenyl group, arylethynyl group, carboxyl group, alkyloxy carbonyl group, aryloxy carbonyl group, arylalkyloxy carbonyl group, hetero aryloxy carbonyl group, cyano group, etc.

As the aromatic hydrocarbon compounds, following compounds are exemplified.

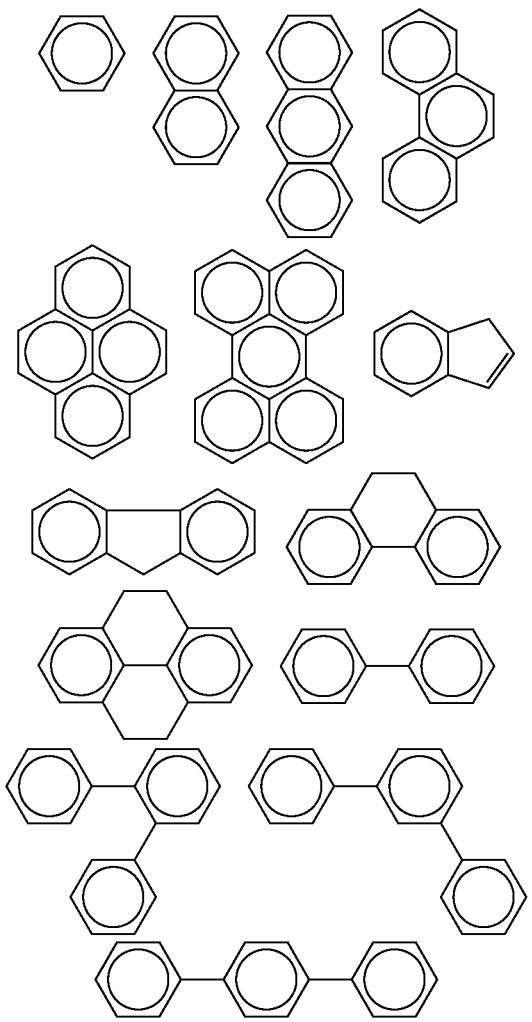

The trivalent heterocyclic group and tetravalent heterocyclic group mean groups in which 3 and 4 hydrogens are removed respectively from heterocyclic compounds, and usually have 3 to 60 carbon atoms, preferably 3 to 20 carbon atoms. They may carry a substituent on the aromatic hydrocarbon groups, but the number of carbon atoms of the substituent is not counted as the number of carbon atoms of the heterocyclic group. Examples of the substituent include an alkyl group, alkyloxy group, alkylthio group, aryl group, aryloxy group, arylthio group, arylalkyl group, arylalkyloxy group, arylalkylthio group, acyl group, acyloxy group, amide group, acid imide group, imine residue, amino group, substituted amino group, substituted silyl group, substituted silyloxy group, substituted silylthio group, substituted silylamino group, monovalent heterocyclic group, hetero aryloxy group, hetero arylthio group, arylalkenyl group, arylethynyl group, carboxyl group, alkyloxy carbonyl group, aryloxy carbonyl group, arylalkyloxy carbonyl group, hetero aryloxy carbonyl group, cyano group, etc. As the heterocyclic compounds, following compound are exemplified.

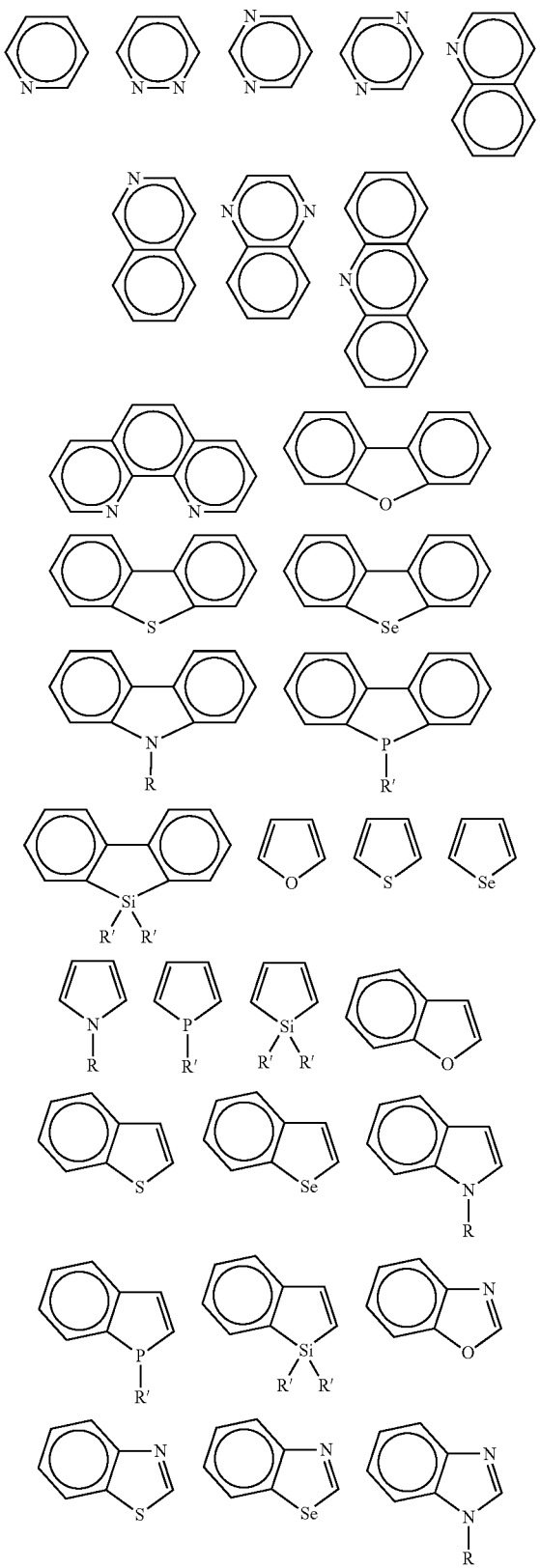

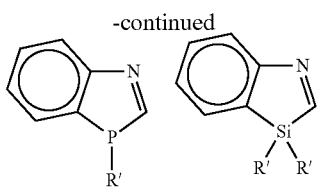

Wherein, R each independently represent a hydrogen atom, alkyl group, aryl group, arylalkyl group, substituted silyl group, acyl group, or monovalent heterocyclic group. R' each independently represent a hydrogen atom, halogen atom, alkyl group, alkyloxy group, alkylthio group, aryl group, aryloxy group, arylthio group, arylalkyl group, arylalkyloxy group, arylalkylthio group, acyloxy group, substituted amino group, amide group, arylalkenyl group, arylalkynyl group, monovalent heterocyclic group, hetero aryloxy group, hetero arylthio group, or cyano group.

In the substituents which $Ar^1$, $Ar^2$ and $Ar^3$ may have, the alkyl group may be any of linear, branched or cyclic, and may have a substituent. The number of carbon atoms is usually about 1 to 20, and specific examples thereof include methyl group, ethyl group, propyl group, i-propyl group, butyl group, i-butyl group, t-butyl group, pentyl group, hexyl group, cyclohexyl group, heptyl group, octyl group, 2-ethylhexyl group, nonyl group, decyl group, 3,7-dimethyloctyl group, lauryl group, trifluoromethyl group, pentafluoroethyl group, perfluorobutyl group, perfluorohexyl group, perfluorooctyl group, etc.

The alkyloxy group may be any of linear, branched or cyclic, and may have a substituent. The number of carbon atoms is usually about 1 to 20, and specific examples thereof include methoxy group, ethoxy group, propyloxy group, i-propyloxy group, butoxy group, i-butoxy group, t-butoxy group, pentyloxy group, hexyloxy group, cyclohexyloxy group, heptyloxy group, octyloxy group, 2-ethylhexyloxy group, nonyloxy group, decyloxy group, 3,7-dimethyl octyloxy group, It exemplifies lauryloxy group, trifluoromethoxy group, pentafluoroethoxy group, perfluorobutoxy group, perfluorohexyl group, perfluoro octyl group, methoxymethyloxy group, 2-methoxy ethyloxy group, etc.

The alkylthio group may be any of linear, branched or cyclic, and may have a substituent. The number of carbon atoms is usually about 1 to 20, and specific examples thereof include methylthio group, ethylthio group, propylthio group, i-propylthio group, butylthio group, i-butylthio group, t-butylthio group, pentylthio group, hexylthio group, the cyclo hexylthio group, heptylthio group, octylthio group, 2-ethylhexylthio group, nonylthio group, decylthio group, 3,7-dimethyl octylthio group, laurylthio group, trifluoromethylthio group, etc.

The aryl group may have a substituent. The number of carbon atoms is usually about 3 to 60, and specific examples thereof include phenyl group, and $C_1$-$C_{12}$ alkoxyphenyl group ($C_1$-$C_{12}$ represents the number of carbon atoms 1-12. Hereafter the same), $C_1$-$C_{12}$ alkyl phenyl group, 1-naphtyl group, 2-naphtyl group, pentafluoro phenyl group, pyridyl group, pyridazinyl group, pyrimidyl group, pyrazyl group, triazyl group, etc.

The aryloxy group may have a substituent on the aromatic ring. The number of carbon atoms is usually about 3 to 60, and specific examples thereof include phenoxy group, $C_1$-$C_{12}$ alkoxy phenoxy group, $C_1$-$C_{12}$ alkylphenoxy group, 1-naphtyloxy group, 2-naphtyloxy group, pentafluorophenyloxy group, pyridyloxy group, pyridazinyloxy group, pyrimidyloxy group, pyrazyloxy group, triazyloxy group, etc.

The arylthio group may have a substituent on the aromatic ring. The number of carbon atoms is usually about 3 to 60, and specific examples thereof include phenylthio group, $C_1$-$C_{12}$ alkoxyphenylthio 2-naphthylthio group, pentafluoro phenylthio group, pyridylthio group, pyridazinylthio group, pyrimidylthio group, pyrazylthio group, triazylthio group, etc.

The arylalkyl group may have a substituent, the number of carbon atoms is usually about 7 to 60, and specific examples thereof include phenyl-$C_1$-$C_{12}$ alkyl group, $C_1$-$C_{12}$ alkoxyphenyl-$C_1$-$C_{12}$ alkyl group, $C_1$-$C_{12}$ alkylphenyl-$C_1$-$C_{12}$ alkyl group, 1-naphtyl-$C_1$-$C_{12}$ alkyl group, 2-naphtyl-$C_1$-$C_{12}$ alkyl group, etc.

The arylalkyloxy group may have a substituent, the number of carbon atoms is usually about 7 to 60, and specific examples thereof include phenyl-$C_1$-$C_{12}$ alkoxy group, $C_1$-$C_{12}$ alkoxyphenyl-$C_1$-$C_{12}$ alkoxy group, $C_1$-$C_{12}$ alkylphenyl-$C_1$-$C_{12}$ alkoxy group, 1-naphtyl-$C_1$-$C_{12}$ alkoxy group, 2-naphtyl-$C_1$-$C_{12}$ alkoxy group, etc.

The arylalkylthio group may have a substituent, the number of carbon atoms is usually about 7 to 60, and specific examples thereof include phenyl-$C_1$-$C_{12}$ alkylthio group, $C_1$-$C_{12}$ alkoxy phenyl-$C_1$-$C_{12}$ alkylthio group, $C_1$-$C_{12}$ alkylphenyl-$C_1$-$C_{12}$ alkylthio group, 1-naphtyl-$C_1$-$C_{12}$ alkylthio group, 2-naphtyl-$C_1$-$C_{12}$ alkylthio group, etc.

The acyl group has usually about 2 to 20 carbon atoms, and specific examples thereof include acetyl group, propionyl group, butyryl group, isobutyryl group, pivaloyl group, benzoyl group, trifluoroacetyl group, pentafluorobenzoyl group, etc.

The acyloxy group has usually about 2 to 20 carbon atoms, and specific examples thereof include acetoxy group, propionyloxy group, butyryloxy group, isobutyryloxy group, pivaloyloxy group, benzoyloxy group, trifluoro acetyloxy group, pentafluorobenzoyloxy group, etc.

The amide group has usually about 2 to 20 carbon atoms, and specific examples thereof include formamide group, acetamide group, propioamide group, butyroamide group, benzamide group, trifluoroacetamide group, pentafluoro benzamide group, diformamide group, diacetoamide group, dipropioamide group, dibutyroamide group, dibenzamide group, ditrifluoro acetamide group, dipentafluorobenzamide group, etc.

Examples of the acid imide group include residual groups in which a hydrogen atom connected with nitrogen atom is removed, and have usually about 2 to 60 carbon atoms, preferably 2 to 48 carbon atoms. As the concrete examples of acid imide group, the following groups are exemplified.

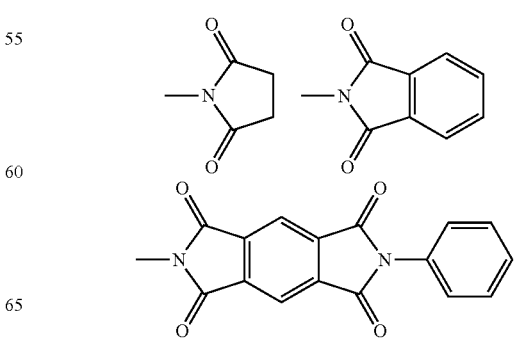

-continued

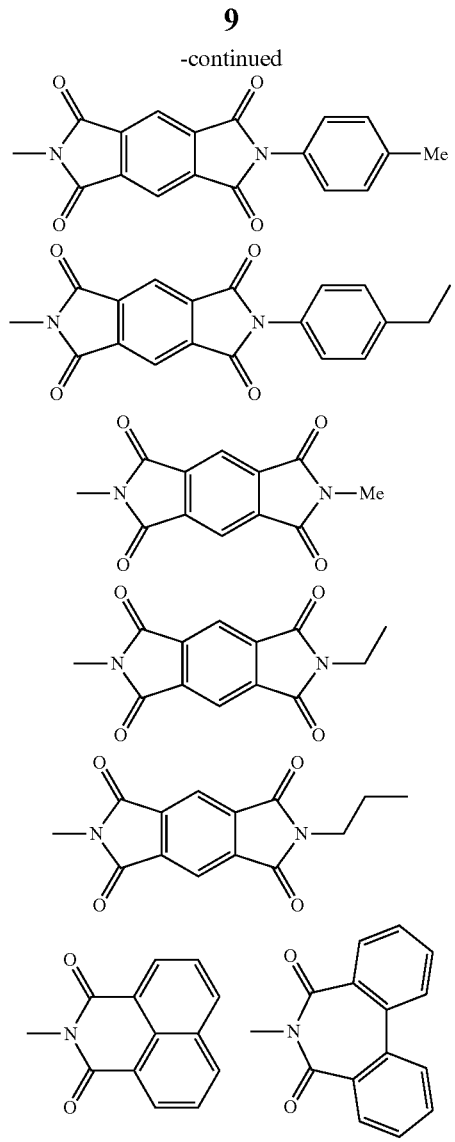

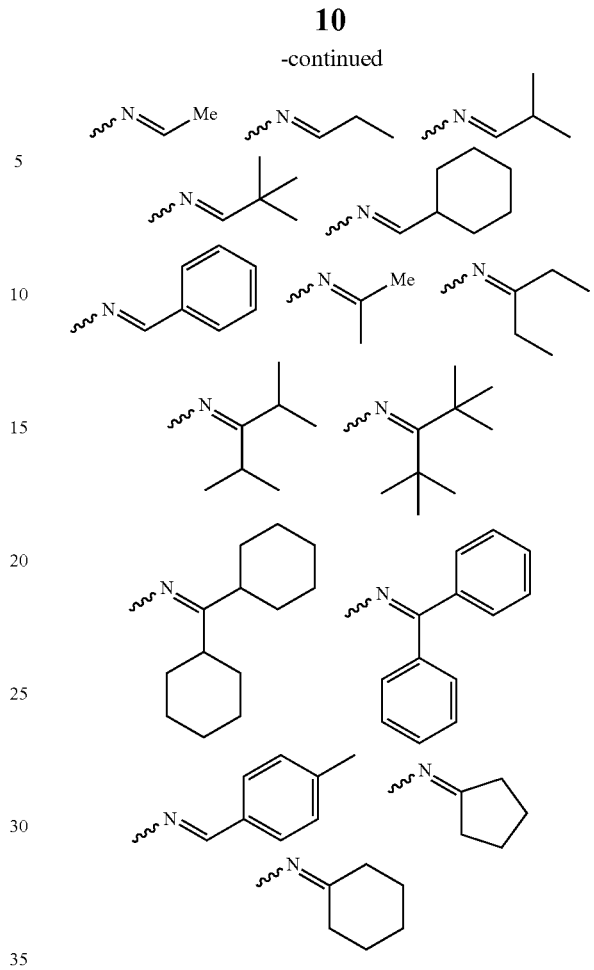

Imine residue is a residue in which a hydrogen atom is removed from an imine compound (an organic compound having —N═C— is in the molecule. Examples thereof include aldimine, ketimine, and compounds whose hydrogen atom on N is substituted with an alkyl group etc.), and usually has about 2 to 20 carbon atoms, preferably 2 to 18 carbon atoms. As the concrete examples, groups represented by below structural formulas are exemplified.

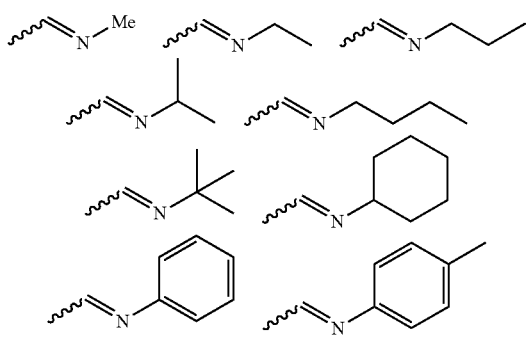

The substituted amino group includes an amino group substituted by 1 or 2 groups selected from an alkyl group, aryl group, arylalkyl group, or monovalent heterocyclic group. Said alkyl group, aryl group, arylalkyl group, or monovalent heterocyclic group may have a substituent.

The number of carbon atoms is usually about 1 to 40, and specific examples thereof include methylamino group, dimethylamino group, ethylamino group, diethylamino group, propylamino group, dipropylamino group, isopropylamino group, diisopropylamino group, butylamino group, isobutylamino group, t-butylamino group, pentylamino group, hexylamino group, cyclohexylamino group, heptylamino group, octylamino group, 2-ethylhexylamino group, nonylamino group, decylamino group, 3,7-dimethyloctylamino group, laurylamino group, cyclopentylamino group, dicyclo pentylamino group, cyclohexylamino group, dicyclohexylamino group, pyrrolidyl group, piperidyl group, ditrifluoromethylamino group, phenylamino group, diphenylamino group, $C_1$-$C_{12}$ alkoxy phenylamino group, di($C_1$-$C_{12}$ alkoxyphenyl)amino group, di($C_1$-$C_{12}$ alkylphenyl)amino group, 1-naphtylamino group, 2-naphtylamino group, pentafluorophenylamino group, pyridylamino group, pyridazinylamino group, pyrimidylamino group, pyrazylamino group, triazylamino group, phenyl-$C_1$-$C_{12}$ alkylamino group, $C_1$-$C_{12}$ alkoxyphenyl-$C_1$-$C_{12}$ alkylamino group, $C_1$-$C_{12}$ alkylphenyl-$C_1$-$C_{12}$ alkylamino group, di($C_1$-$C_{12}$ alkoxy phenyl-$C_1$-$C_{12}$ alkyl)amino group, di($C_1$-$C_{12}$ alkylphenyl-$C_1$-$C_{12}$ alkyl)amino group, 1-naphtyl-$C_1$-$C_{12}$ alkylamino group, 2-naphtyl-$C_1$-$C_{12}$ alkylamino group, etc.

The substituted silyl group includes a silyl group substituted by 1, 2 or 3 groups selected from an alkyl group, aryl group, arylalkyl group, or monovalent heterocyclic group. The number of carbon atoms is usually about 1 to 60, and preferably 3 to 30. Said alkyl group, aryl group, arylalkyl group, or monovalent heterocyclic group may have a substituent.

Examples thereof include trimethylsilyl group, triethylsilyl group, tri-n-propylsilyl group, tri-i-propylsilyl group, t-butylsilyl dimethylsilyl group, triphenylsilyl group, tri-p-xylylsilyl group, tri benzylsilyl group, diphenylmethylsilyl group, t-butyldiphenylsilyl group, dimethylphenylsilyl group, etc.

Examples of the substituted silyloxy group includes a silyloxy group ($H_3SiO$—) substituted by 1, 2 or 3 groups selected from an alkyl group, aryl group, arylalkyl group, or monovalent heterocyclic group. The number of carbon atoms is usually about 1 to 60, and preferably 3 to 30. Said alkyl group, aryl group, arylalkyl group, or monovalent heterocyclic group may have a substituent.

Examples of the substituted silyloxy groups include trimethylsilyloxy group, triethylsilyloxy group, tri-n-propylsilyloxy group, tri-i-propylsilyloxy group, t-butylsilyl dimethylsilyloxy group, triphenylsilyloxy group, tri-p-xylylsilyloxy group, tri benzylsilyloxy group, diphenyl methylsilyloxy group, t-butyl diphenylsilyloxy group, dimethylphenylsilyloxy group, etc.

Examples of the substituted silylthio group includes a silylthio group ($H^3SiS$—) substituted by 1, 2 or 3 groups selected from an alkyl group, aryl group, arylalkyl group, or monovalent heterocyclic group. The number of carbon atoms is usually about 1 to 60, and preferably 3 to 30. Said alkyl group, aryl group, arylalkyl group, or monovalent heterocyclic group may have a substituent.

Examples of the substituted silylthio groups include trimethylsilylthio group, triethylsilylthio group, tri-n-propylsilylthio group, tri-i-propylsilylthio group, t-butylsilyl dimethylsilylthio group, triphenylsilylthio group, tri-p-xylylsilylthio group, tribenzylsilylthio group, diphenylmethylsilylthio group, t-butyldiphenylsilylthio group, dimethylphenylsilylthio group, etc.

As the substituted silylamino group, exemplifeid is a silylamino group ($H_3SiNH$— or $(H_3Si)_2N$—) which is substituted by 1 to 6 groups selected from an alkyl group, aryl group, arylalkyl group, or monovalent heterocyclic group. The number of carbon atoms is usually about 1 to 120, and preferably 3 to 60. Said alkyl group, aryl group, arylalkyl group, or monovalent heterocyclic group may have a substituent.

Examples of the substituted silylamino include trimethylsilylamino group, triethylsilylamino group, tri-n-propylsilylamino group, tri-i-propylsilylamino group, t-butylsilyl dimethylsilylamino group, triphenylsilylamino group, tri-p-xylylsilylamino group, tribenzylsilylamino group, diphenyl methylsilylamino group, t-butyl diphenylsilylamino group, Dimethylphenylsilylamino group, di(trimethylsilyl)amino group, di(triethylsilyl)amino group, di(tri-n-propylsilyl)amino group, di(tri-i-propylsilyl)amino group, di(t-butylsilyldimethylsilyl)amino group, di(triphenylsilyl)amino group, di(tri-p-xylylsilyl)amino group, di(tribenzylsilyl)amino group, di(diphenyl methylsilyl)amino group, di(t-butyldiphenylsilyl)amino group, di(dimethylphenylsilyl)amino group, etc.

The monovalent heterocyclic group is an atomic group in which a hydrogen atom is removed from a heterocyclic compound, the number of carbon atoms is usually about 4 to 60, and specific examples thereof include thienyl group, $C_1$-$C_{12}$ alkylthienyl group, pyroryl group, furyl group, pyridyl group, $C_1$-$C_{12}$ alkyl pyridyl group, imidazolylgroup, pyrazolylgroup, triazolylgroup, oxazolylgroup, thiazole group, thiadiazole group, etc.

The hetero aryloxy group is a group in which one hydrogen atom of a heterocyclic compound is replaced by an oxygen atom, and represented by $Q^1$-O—. $Q^1$ represents a monovalent heterocyclic group. The number of carbon atoms is usually about 2 to 60, and concrete examples thereof include a thienyloxy group, $C_1$-$C_{12}$ alkylthienyloxy group, pyroryloxy group, furyl oxy group, pyridyloxy group, $C_1$-$C_{12}$ alkylpyridyloxy group, imidazolyloxy group, pyrazolyloxy group, triazolyloxy group, oxazolyloxy group, thiazoleoxy group, thiadiazoleoxy group, etc.

The hetero arylthio group is a group in which one hydrogen atom of a heterocyclic compound is replaced by an sulfur atom, and represented by $Q^2$-S—. $Q^2$ represents a monovalent heterocyclic group. The number of carbon atoms is usually about 2 to 60, and concrete examples thereof include thienyl-mercapto group, $C_1$-$C_{12}$ alkyl thienyl-mercapto group, pyroryl mercapto group, furyl mercapto group, pyridyl mercapto group, $C_1$-$C_{12}$ alkyl pyridyl mercapto group, imidazolyl mercapto group, pyrazolyl mercapto group, triazolyl mercapto group, oxazolyl mercapto group, thiazole mercapto group, thiadiazole mercapto group, etc.

The hetero aryloxycarbonyl group is a group in which one hydrogen atom of a heterocyclic compound is replaced by an oxy carbonyl group, and represented by $Q^3$-O(C=O)—. $Q^3$ represents a monovalent heterocyclic group. The number of carbon atoms is usually about 2 to 60, and concrete examples thereof include thienyloxy carbonyl group, $C_1$-$C_{12}$ alkyl thienyloxy carbonyl group, pyroryloxy carbonyl group, furyloxy carbonyl group, pyridyloxy carbonyl group, $C_1$-$C_{12}$ alkyl pyridyloxy carbonyl group, imidazolyloxy carbonyl group, pyrazolyloxy carbonyl group, triazolyloxy carbonyl group, oxazolyloxy carbonyl group, thiazoleoxy carbonyl group, thiadiazoleoxy carbonyl group, etc.

As the aryl group in arylalkenyl group and arylethynyl group, examples of the groups in the above aryl group are exemplified. The number of carbon atoms of the alkenyl group in arylalkenyl group is usually about 2 to 20, and examples thereof include a vinyl group, 1-propyrenyl group, 2-propyrenyl group, 3-propyrenyl group, butenyl group, pentenyl group, hexenyl group, heptenyl group, octenyl group, cyclohexenyl group, 1,3-butadienyl group, etc.

$A^1$ in formula (1) and (2) represents —$Z^1$—, —$Z^2$—$Z^3$— or —$Z^4$=$Z^5$—. $Z^1$, $Z^2$ and $Z^3$ each independently represents O, S, C(=O), S(=O), $SO_2$, $C(R^2)(R^1)$, $Si(R^3)(R^4)$, $N(R^5)$, $B(R^6)$, $P(R^7)$, or $P(=O)(R^8)$. $Z^4$ and $Z^5$ each independently represent N, B, P, $C(R^9)$, or $Si(R^{10})$. (Wherein, $R^1$, $R^2$, $R^3$, $R^4$, $R^5$, $R^6$, $R^7$, $R^8$, $R^9$, and $R^{10}$ each independently represent a hydrogen atom, halogen atom, alkyl group, alkyloxy group, alkylthio group, aryl group, aryloxy group, arylthio group, arylalkyl group, arylalkyloxy group, arylalkylthio group, acyl group, acyloxy group, amide group, acid imide group, imine residue, amino group, substituted amino group, substituted silyl group, substituted silyloxy group, substituted silylthio group, substituted silylamino group, monovalent heterocyclic group, hetero aryloxy group, hetero arylthio group, arylalkenyl group, arylethynyl group, carboxyl group, alkyloxy carbonyl group, aryloxy carbonyl group, arylalkyloxy carbonyl group, hetero aryloxy carbonyl group, or cyano group. $R^1$, and $R^2$, and $R^3$ and $R^4$ may be connected mutually to form a ring.)

The definition and concrete examples of the halogen atom, alkyl group, alkyloxy group, alkylthio group, aryl group, aryloxy group, arylthio group, arylalkyl group, arylalkyloxy group, arylalkylthio group, acyl group, acyloxy group, amide group, acid imide group, imine residue, substituted amino group, substituted silyl group, substituted silyloxy group, substituted silylthio group, substituted silylamino group, monovalent heterocyclic group, hetero aryloxy group, hetero arylthio group, arylalkenyl group and arylethynyl group in $R^1$, $R^2$, $R^3$, $R^4$, $R^5$, $R^6$, $R^7$, $R^8$, $R^9$ and $R^{10}$ are the same as those of the above.

In formula (1), $Ar^2$ and $A^1$ bond to mutually adjacent atoms of $Ar^1$ ring, and $Ar^1$ and $A^1$ bond to mutually adjacent atoms of $Ar^2$ ring. In formula (2), $Ar^3$ and $A^1$ bond to mutually adjacent atoms of $Ar^1$ ring, and $Ar^1$ and $A^1$ bond to mutually adjacent atoms of $Ar^3$ ring.

As —$Z^1$— in $A^1$, following groups are specifically exemplified.

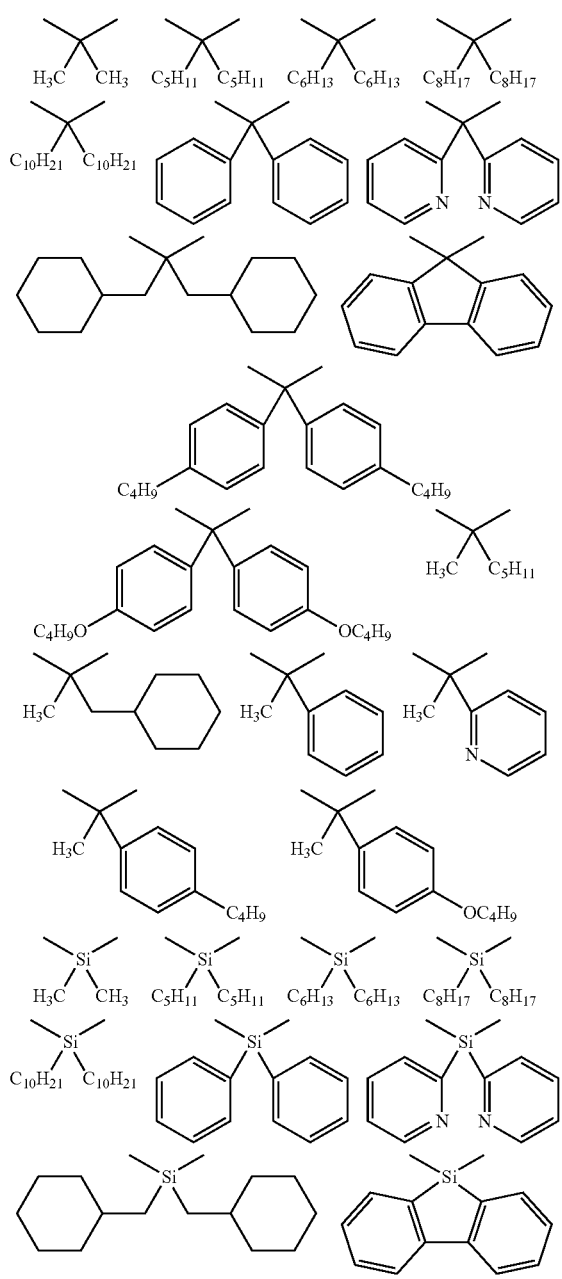

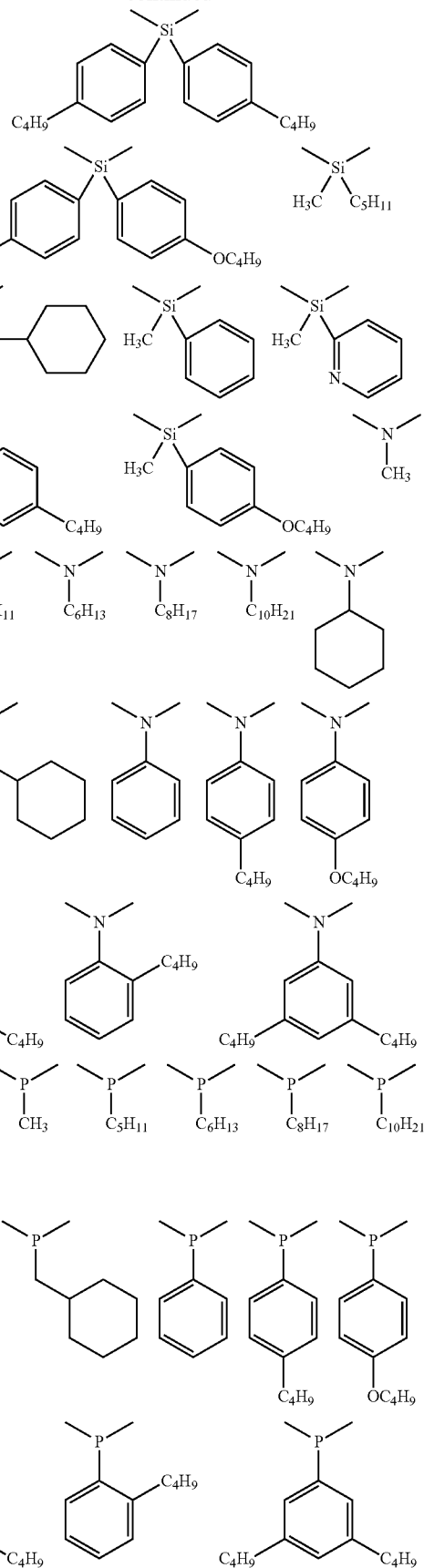

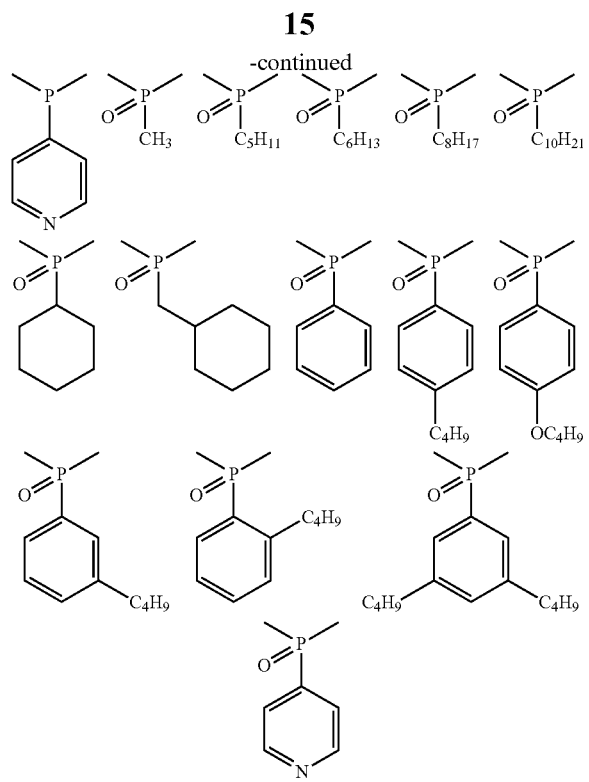
As —Z²—Z³— in A¹, groups of the below (16), (17), and (18) are exemplified.
(16)
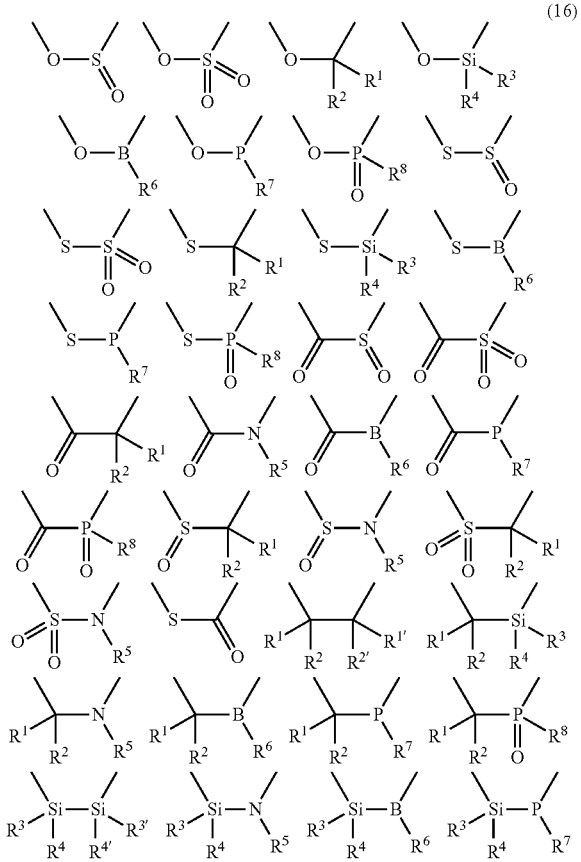
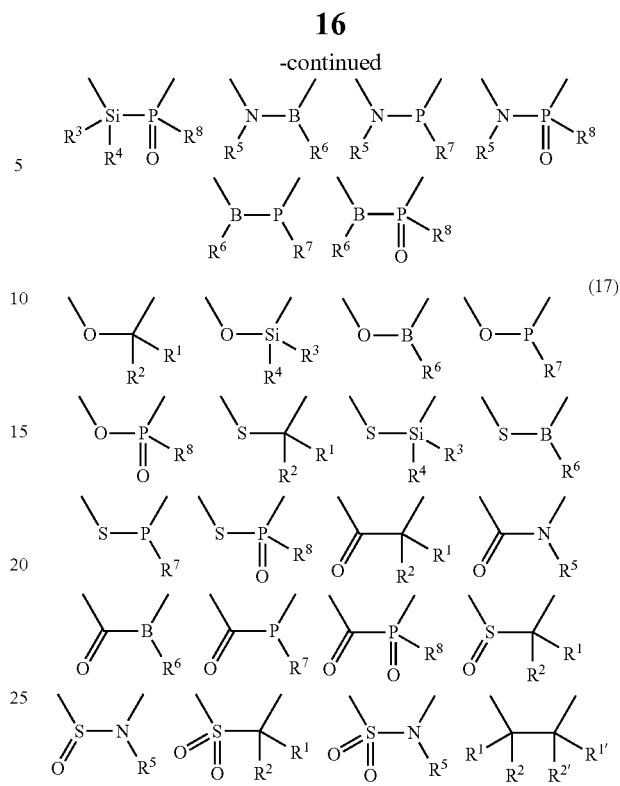
(17)
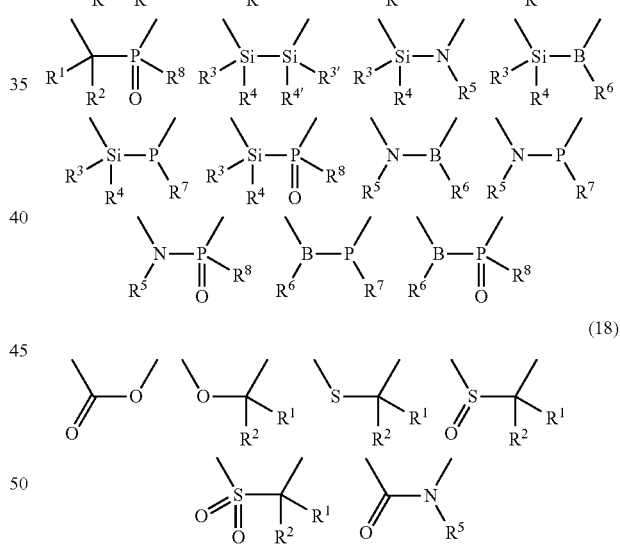
(18)
As —Z⁴=Z⁵— in A¹, groups of the below (19) and (20) are exemplified.
(19)
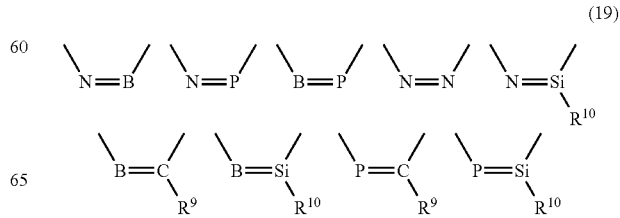

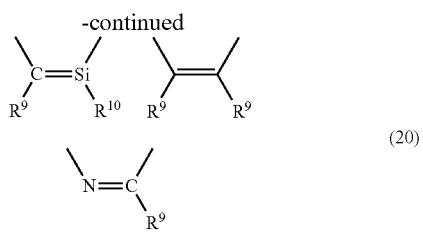

(20)

In formula (1) and (2), $X^1$, $X^2$, $X^3$ and $X^4$ each independently represent a halogen atom, alkylsulfonate group, arylsulfonate group, arylalkylsulfonate group, boric ester group, —B(OH)$_2$, monohalogenated-methyl group, sulfonium-methyl group, phosphonium-methyl group, phosphonate-methyl group, cyano methyl group, formyl group, vinyl group, hydroxyl group, alkyloxy group, acyloxy group, substituted silyloxy group, amino group, or nitro group. At least one of $X^1$, $X^2$ and $X^3$ in formula (1) is selected from a halogen atom, alkylsulfonate group, arylsulfonate group, arylalkylsulfonate group, boric ester group, —B(OH)$_2$, monohalogenated-methyl group, sulfonium-methyl group, phosphonium-methyl group, phosphonate-methyl group, cyanomethyl group, formyl group, or vinyl group. At least one of $X^1$, $X^2$, $X^3$, and $X^4$ in formula (2) is selected from a halogen atom, alkylsulfonate group, arylsulfonate group, arylalkylsulfonate group, boric ester group, —B(OH)$_2$, monohalogenated-methyl group, sulfonium-methyl group, phosphonium-methyl group, phosphonate-methyl group, cyano methyl group, formyl group, or vinyl group.

As the halogen atom, fluorine, chlorine, bromine and iodine are exemplified, and chlorine, bromine and iodine are preferable.

Examples of the alkylsulfonate group include a methane sulfonate group, ethane sulfonate group, trifluoromethane sulfonate group, etc., examples of the arylsulfonate group include a benzene sulfonate group, p-toluene sulfonate group, etc., and examples of the arylalkylsulfonate group include a benzyl sulfonate group, etc.

As boric ester group, the groups represented by the below formulae are exemplified.

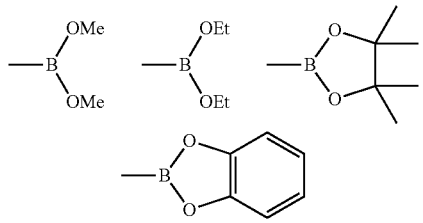

As the monohalogenated-methyl group, chloromethyl group, bromomethyl group, and iodomethyl group are exemplified.

As the sulfonium-methyl group, the groups represented by the below formulae are exemplified.

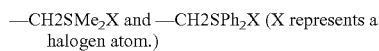
—CH2SMe$_2$X and —CH2SPh$_2$X (X represents a halogen atom.)

As the phosphonium-methyl group, the groups represented by the below formulae are exemplified.

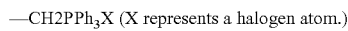
—CH2PPh$_3$X (X represents a halogen atom.)

As the phosphonate-methyl group, the groups represented by the below formulae are exemplified.

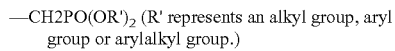
—CH2PO(OR')$_2$ (R' represents an alkyl group, aryl group or arylalkyl group.)

When the compound of the above formula (1) or (2) has a condensation-reactive functional group and a condensation-reactive functional group precursor, the condensation-reactive functional group precursor can be converted into a functional group after performing a condensation reaction, and regio-selective substituent introduction and a polymerization reaction can be conducted by further performing a condensation reaction.

The condensation-reactive functional group includes a halogen atom, alkylsulfonate group, arylsulfonate group, arylalkylsulfonate group, boric ester group, —B(OH)$_2$, methyl monohalide group, sulfonium methyl group, phosphonium methyl group, phosphonate methyl group, cyanomethyl group, formyl group and vinyl group, and the condensation-reactive functional group precursor indicates a functional group which can be converted into a condensation-reactive functional group by performing functional group conversion, and specifically listed are a hydroxyl group, alkyloxy group, acyloxy group, substituted silyloxy group, amino group and nitro group.

As the method of converting a condensation-reactive functional group precursor into a condensation-reactive functional group, when the condensation-reactive functional group precursor is a hydroxyl group, it can be converted into an alkylsulfonate group by reacting with an alkylsulfonic anhydride or alkylsulfonyl chloride in the presence of a base. In a like manner, it can be converted into an arylsulfonate or arylalkylsulfonate group by using the corresponding sulfonic anhydride or sulfonyl chloride.

When the condensation-reactive functional group precursor is an alkyloxy group, it can be converted into a hydroxyl group using boron tribromide and the like, then, converted into an alkylsulfonate group, arylsulfonate group or arylalkylsulfonate group using the above method.

When the condensation-reactive functional group precursor is an acyloxy group, it can be converted into a hydroxyl group by hydrolysis under basic conditions or by reaction with a reducing agent, then, converted into an alkylsulfonate group, arylsulfonate group or arylalkylsulfonate group using the above method.

When the condensation-reactive functional group precursor is a substituted silyloxy group, it can be converted into a hydroxyl group by hydrolysis under acidic conditions, hydrolysis under basic conditions or by reaction with a fluoride ion, then, converted into an alkylsulfonate group, arylsulfonate group or arylalkylsulfonate group using the above method.

When the condensation-reactive functional group precursor is an amino group, it can be converted into a halogen atom by Sandmeyer reaction.

When the condensation-reactive functional group precursor is a nitro group, it can be converted into an amino group by reacting with a reducing agent, then, converted into a halogen atom using the above method.

When the compound of the above formula (1) or (2) has a condensation-reactive functional group and a condensation-reactive functional group precursor, it is preferable that $A^1$ is O, C(R$^1$)(R$^2$), N(R$^5$) or B(R$^6$) in view of emission strength when the compound is made into a polymer.

It is also preferable that $Z^2$ and $Z^3$ in —$Z^2$—$Z^3$— are mutually different or represented by —$Z^4$=$Z^5$— in view of emission strength when the compound is made into a polymer. Specifically, groups exemplified by the above formula (16), (17), (18), (19) or (20) are listed.

Particularly, it is more preferable that $A^1$ represents O—C(=O), O—C(R$^1$)(R$^2$), S—C(R$^1$)(R$^2$), S(=O)—C(R$^1$)(R$^2$), $SO_2$—$C(R^1)(R^2)$, $N(R^5)$—$C(=O)$ or $N=C(R^9)$. Specifically, groups exemplified by the above formula (18) or (20) are listed.

It is preferable that all of $X^1$, $X^2$ and $X^3$ in formula (1) are selected from a halogen atom, alkylsulfonate group, arylsulfonate group, arylalkylsulfonate group, boric ester group, —$B(OH)_2$, methyl monohalide group, sulfonium methyl group, phosphonium methyl group, phosphonate methyl group, cyanomethyl group, formyl group and vinyl group, and that all of $X^1$, $X^2$, $X^3$ and $X^4$ in formula (2) are selected from a halogen atom, alkylsulfonate group, arylsulfonate group, arylalkylsulfonate group, boric ester group, —$B(OH)_2$, methyl monohalide group, sulfonium methyl group, phosphonium methyl group, phosphonate methyl group, cyanomethyl group, formyl group and vinyl group, since then a branched polymer is obtained by directly performing polymerization.

Particularly, it is preferable that at least one of $X^1$, $X^2$ and $X^3$ in formula (1) is a functional group different from the other functional groups and that at least one of $X^1$, $X^2$, $X^3$ and $X^4$ in formula (2) is a functional group different from the other functional groups since then the reaction site of the condensation reaction can be controlled.

Particularly, it is preferable that at least one of $X^1$, $X^2$ and $X^3$ is a halogen atom and at least one of $X^1$, $X^2$ and $X^3$ is a sulfonate group. Here, the sulfonate group indicates an alkylsulfonate group, arylsulfonate group or arylalkylsulfonate group.

It is preferable that $A^1$ is O, S, S(=O) or $SO_2$ in view of emission strength when the compound is made into a polymer and it is preferable that $A^1$ is $C(R^1)(R^2)$, $Si(R^3)(R^4)$, $N(R^5)$, $B(R^6)$, $P(R^7)$ or $P(=O)(R^8)$ in view of electric charge transportability when the compound is made into a polymer Further, —$Z^2$=$Z^3$— or —$Z^4$=$Z^5$— is also preferable in view of emission strength when the compound is made into a polymer. Specifically, groups exemplified by the above formula (16), (17), (18), (19) or (20) are listed.

Particularly, it is more preferable that $A^1$ represents O—C(=O), O—$C(R^1)(R^2)$, S—$C(R^1)(R^2)$, S(=O)—$C(R^1)(R^2)$, $SO_2$—$C(R^1)(R^2)$, $N(R^5)$—$C(=O)$ or $N=C(R^9)$. Specifically, groups exemplified by the above formula (18) or (20) are listed.

As the compound of formula (1), compounds of the following formulae (21) and (22) are exemplified.

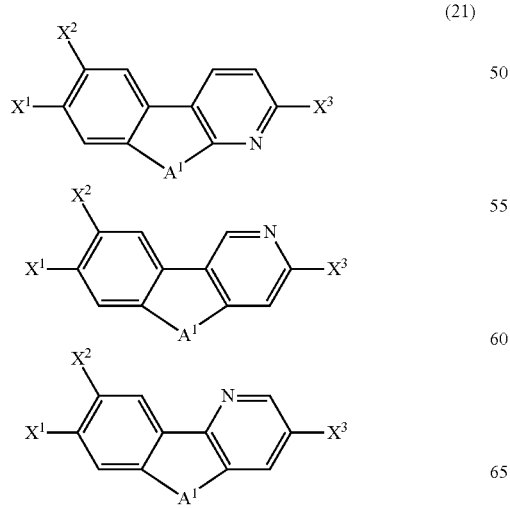

(21)

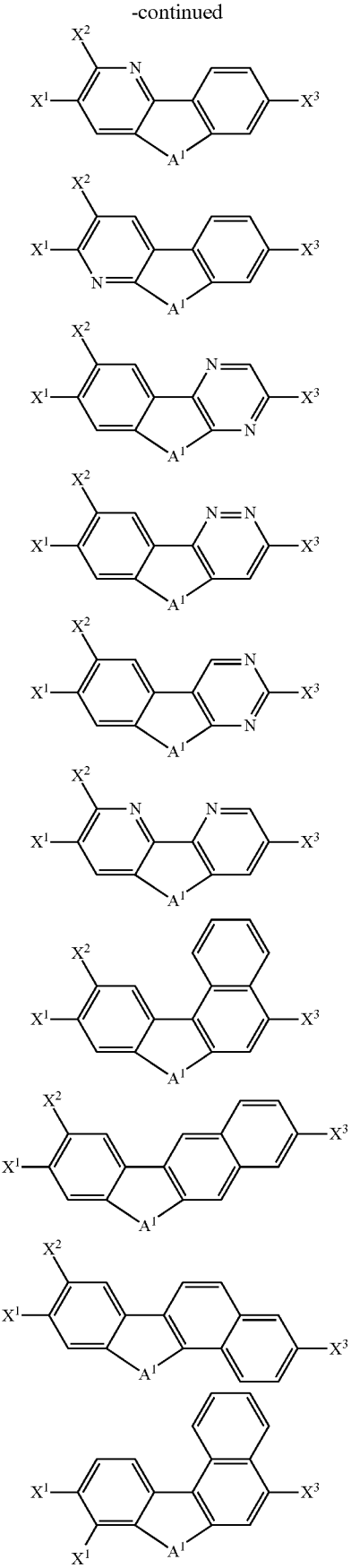

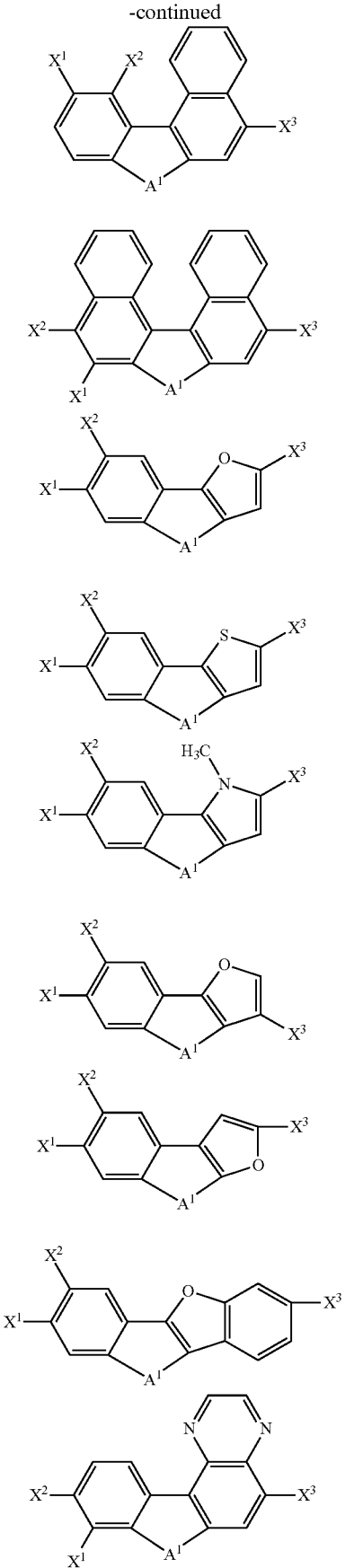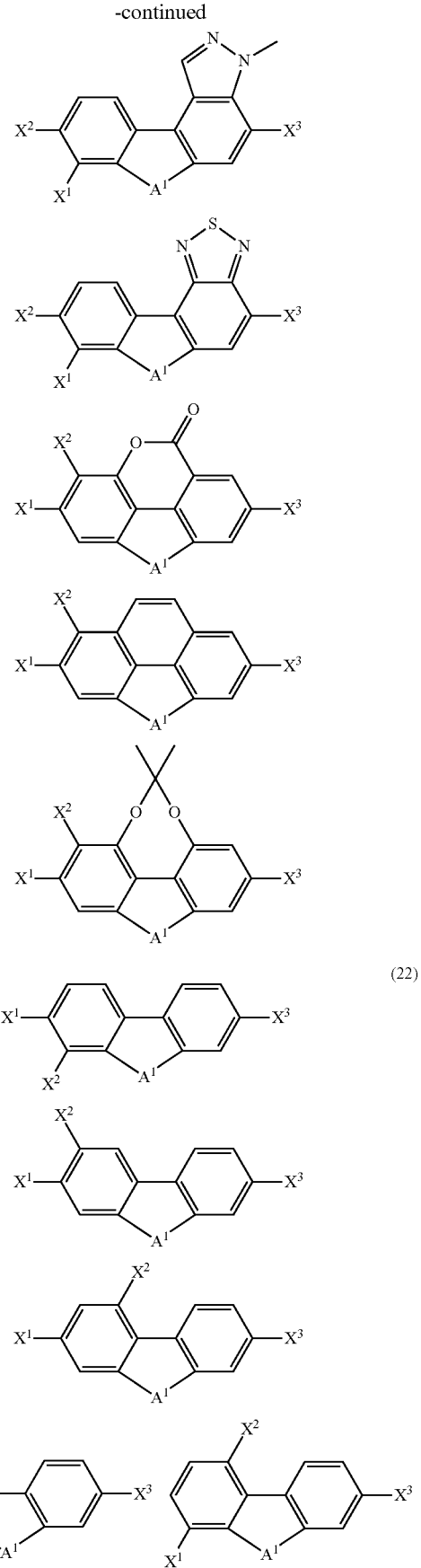

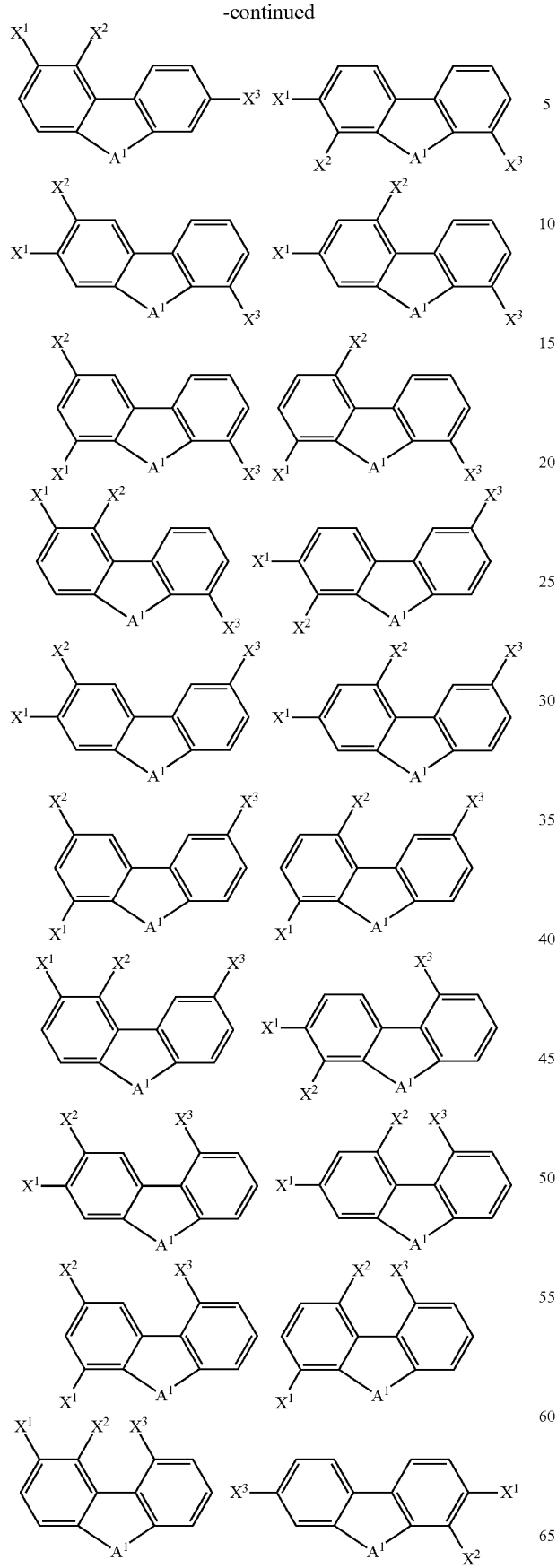
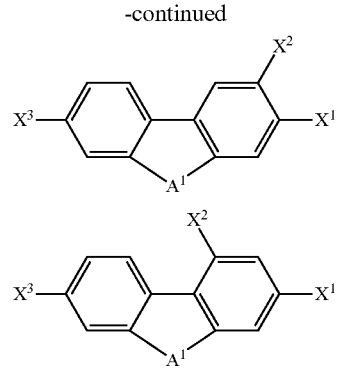
As the compounds represented by formula (2), compounds of the below (23) and (24) are exemplified.
(23)
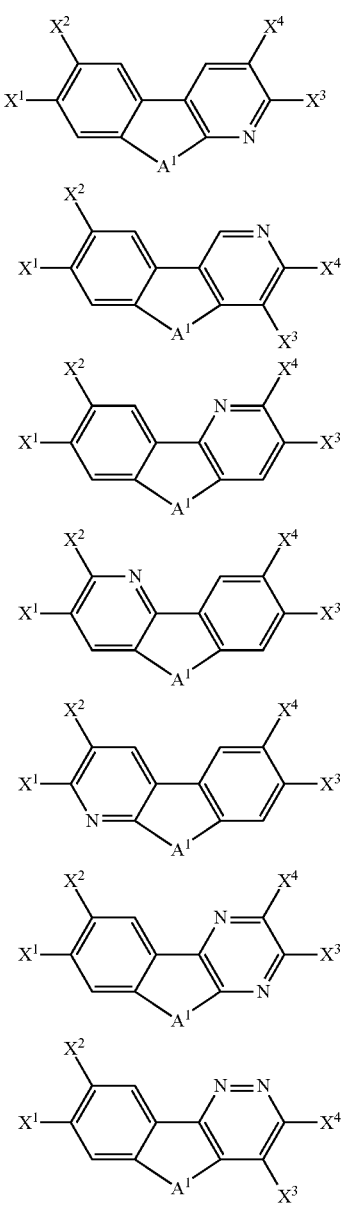

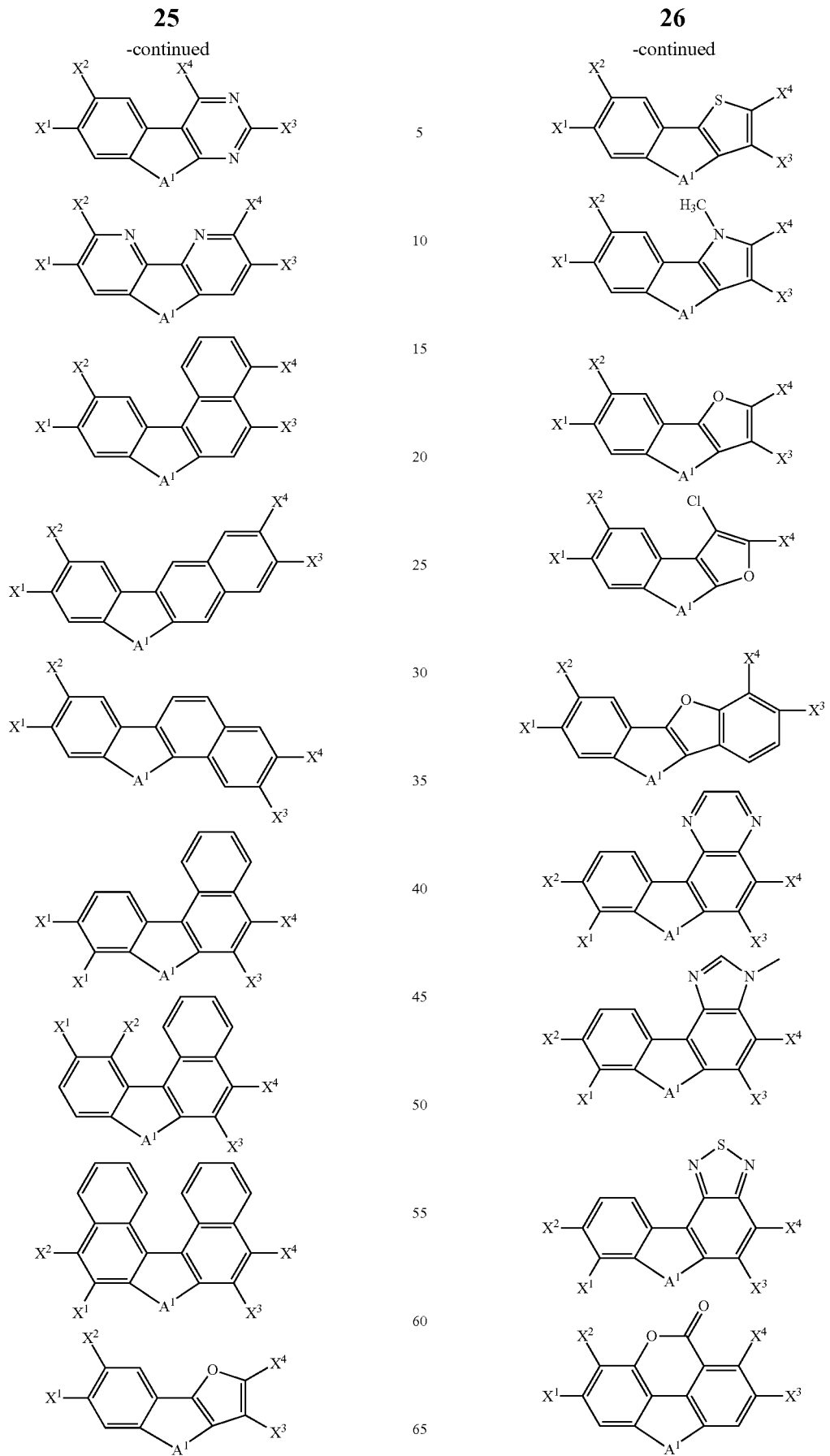

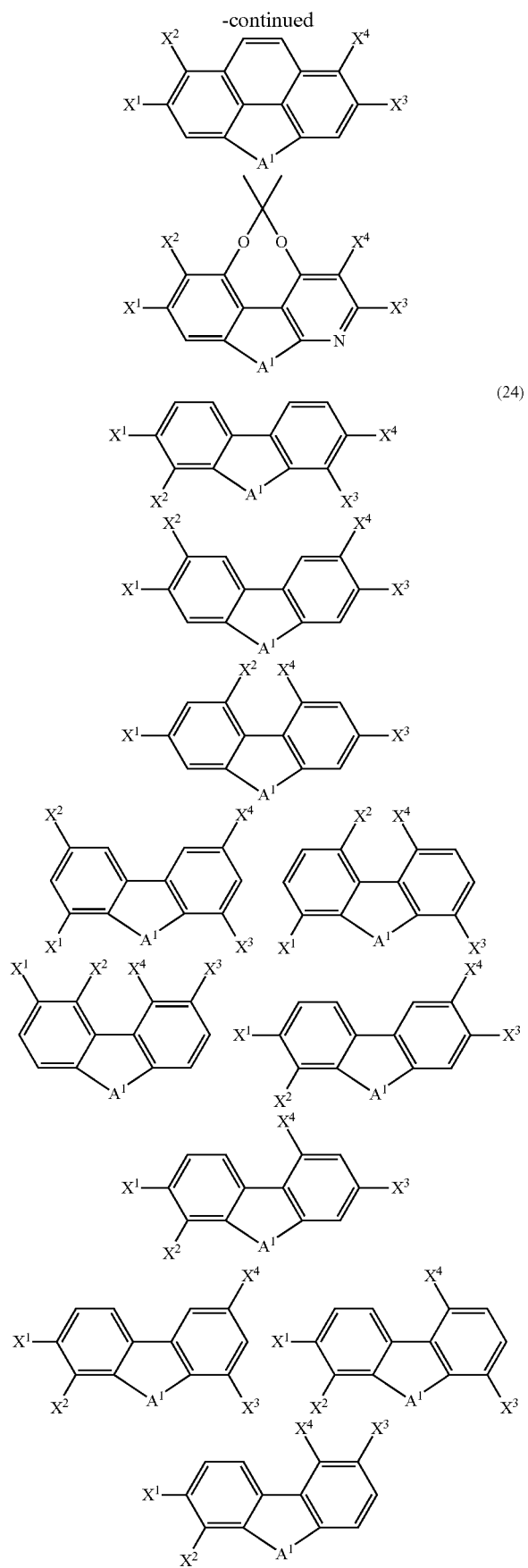

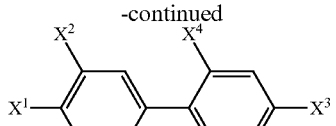
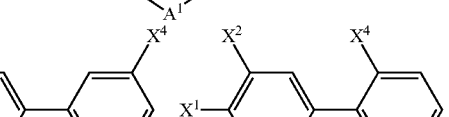
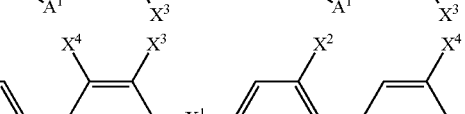
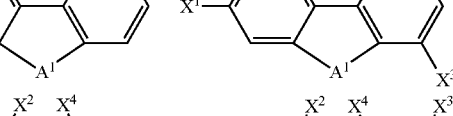
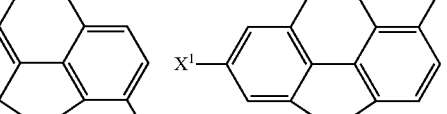
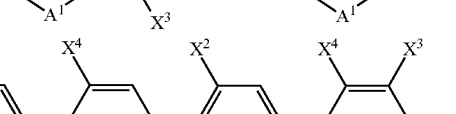
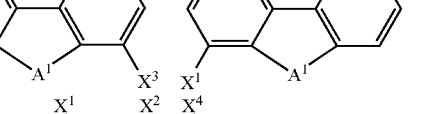
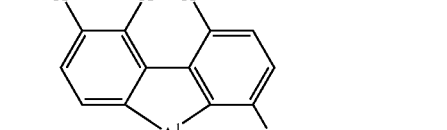

Among them, preferable is a case where $Ar^1$ and $Ar^2$ in the above formula (1) are aromatic hydrocarbons, or $Ar^1$ and $Ar^3$ in the above formula (2) are aromatic hydrocarbons, in view of the stability of the compound.

Especially preferable is a case represented by the below formula (I-1) or (2-1), in view of the stability of the compound.

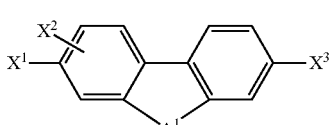

(1-1)

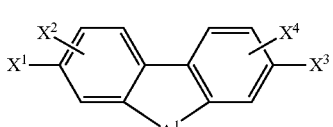

(2-1)

Wherein, $A^1$, $X^1$, $X^2$, $X^3$, and $X^4$ are the same as those of the above. Substituents may be carried on the benzene ring, and the substituents may be mutually connected to form a ring. Examples of the substituent include an alkyl group, alkyloxy group, alkylthio group, aryl group, aryloxy group, arylthio group, arylalkyl group, arylalkyloxy group, arylalkylthio group, acyl group, acyloxy group, amide group, acid imide group, imine residue, amino group, substituted amino group, substituted silyl group, substituted silyloxy group, substituted silylthio group, substituted silylamino group, monovalent heterocyclic group, hetero aryloxy group, hetero arylthio group, arylalkenyl group, arylethynyl group, carboxyl group, alkyloxy carbonyl group, aryloxy carbonyl group, arylalkyloxy carbonyl group, hetero aryloxy carbonyl group, and cyano group.

Synthetic method of the compound represented by (1) or (2) will be described.

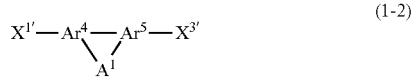

(1-2)

Compounds represented by the above formula (1) or (2) can be manufactured by a method of halogenation of the compounds represented by the above formula (1-2). $X^{1'}$ and $X^{3'}$ each independently represent a halogen atom, alkylsulfonate group, arylsulfonate group, arylalkylsulfonate group, boric ester group, —B(OH)$_2$, monohalogenated-methyl group, sulfonium-methyl group, phosphonium-methyl group, phosphonate-methyl group, cyano methyl group, formyl group, or vinyl group; or a functional group convertible into a halogen atom, alkylsulfonate group, arylsulfonate group, arylalkylsulfonate group, boric ester group, —B(OH)$_2$, monohalogenated-methyl group, sulfonium-methyl group, phosphonium-methyl group, phosphonate-methyl group, cyano methyl group, formyl group, or vinyl group. Among them, it is preferable that $X^{1'}$ and $X^{3'}$ are electron-donating groups.

A synthetic method is exemplified below.

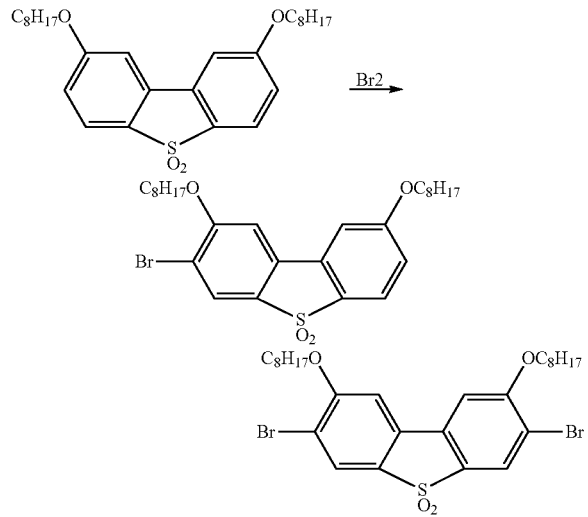

Next, compounds represented by formula (5) or (6) are described.

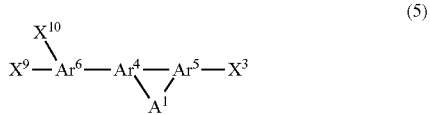

(5)

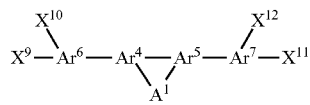

(6)

Wherein, $A^1$ and $X^3$ represent the same meaning as described above, $Ar^4$, $Ar^5$, $Ar^6$, and $Ar^7$ each independently represent a trivalent aromatic hydrocarbon group or a trivalent trivalent heterocyclic group, said $Ar^4$, $Ar^5$, $Ar^6$ and $Ar^7$ may have substituents, and when $Ar^4$ and $Ar^5$ have substituents, they may be connected to form a ring.

The definition and concrete example of the substituent which may be carried on the trivalent aromatic hydrocarbon group, trivalent heterocyclic group, $Ar^4$, $Ar^5$, $Ar^6$ and $Ar^7$ are the same as the definition and concrete examples in formula (1) and (2).

$X^9$, $X^{10}$, $X^{11}$ and $X^{12}$ each independently represent a halogen atom, alkylsulfonate group, arylsulfonate group, arylalkylsulfonate group, boric ester group, —B(OH)$_2$, monohalogenated-methyl group, sulfonium-methyl group, phosphonium-methyl group, phosphonate-methyl group, cyano methyl group, formyl group, vinyl group, hydroxyl group, alkyloxy group, acyloxy group, substituted silyloxy group, amino group, or nitro group. At least one of $X^9$, $X^{10}$ and $X^3$ in formula (5) is selected from a halogen atom, alkylsulfonate group, arylsulfonate group, arylalkylsulfonate group, boric ester group, —B(OH)$_2$, monohalogenated-methyl group, sulfonium-methyl group, phosphonium-methyl group, phosphonate-methyl group, cyano methyl group, formyl group, and vinyl group. At least one of $X^9$, $X^{10}$, $X^{11}$ and $X^{12}$ in formula (6) is selected from a halogen atom, alkylsulfonate group, arylsulfonate group, It is chosen out of arylalkylsulfonate group, boric ester group, —B(OH)$_2$, monohalogenated-methyl group, sulfonium-methyl group, phosphonium-methyl group, phosphonate-methyl group, cyano methyl group, formyl group, and vinyl group.

The definition and concrete example of the halogen atom, alkylsulfonate group, arylsulfonate group, arylalkylsulfonate group, boric ester group, —B(OH)$_2$, monohalogenated-methyl group, sulfonium-methyl group, phosphonium-methyl group, phosphonate-methyl group, alkyloxy group, acyloxy group and substituted silyloxy group in $X^9$, $X^{10}$, $X^{11}$ and $X^{12}$ are the same as the definition and concrete thereof in formula (1) and (2).

When the compounds represented by the above formula (5) or (6) have a condensation reactive functional group and a condensation reactive functional-group precursor, after carrying out a condensation reaction, by condensation reactive functional-group precursor being converted into a functional-group, and further performing a condensation reaction, it becomes possible to perform a regio-selective substituent introduction and a polymerization reaction.

When the compounds represented by the above formula (5) or (6) have a condensation reactive functional group and a condensation reactive functional-group precursor, preferable is the case where $A^1$ is O, S, S(=O), SO$_2$ or Si(R$^3$)(R$^4$), N(R$^5$) in view of the light-emitting strength when this compound is made into a polymer.

The case where it is represented by —Z$^2$—Z$^3$— or —Z$^4$=Z$^5$— is also preferable. Concretely, groups in the above formula (16), (17), (18), (19), or (20) are exemplified.

Among them, preferable is the case where $A^1$ is O—C(=O), O—C(R$^1$)(R$^2$), N(R$^5$)—C(=O), or N=C(R$^9$).

Moreover, preferable are the cases where: all of $X^1$, $X^2$ and $X^3$ in formula (5) are selected from a halogen atom, alkylsulfonate group, arylsulfonate group, arylalkylsulfonate group, boric ester group, —B(OH)$_2$, monohalogenated-methyl group, sulfonium-methyl group, phosphonium-methyl group, phosphonate-methyl group, cyano methyl group, formyl group and vinyl group; and all of $X^1$, $X^2$, $X^3$ and $X^4$ in formula (6) are selected from a halogen atom, alkylsulfonate group, arylsulfonate group, arylalkylsulfonate group, boric ester group, —B(OH)$_2$, monohalogenated-methyl group, sulfonium-methyl group, phosphonium-methyl group, phosphonate-methyl group, cyano methyl group, formyl group, and vinyl group; since it gives a branched polymer by serving it directly to a polymerization.

Among them, preferable are the cases where: at least one of $X^3$, $X^9$ and $X^{19}$ in formula (5) is a different functional group from others; and at least one of $X^9$, $X^{10}$, $X^{11}$, and $X^{12}$ in formula (6) is a different functional group from others; since control of the reaction site of condensation reaction is possible.

Preferable is the case where $A^1$ is O, S, S(=O), SO$_2$, or Si(R$^3$)(R$^4$), N(R$^5$), in view of the light-emitting strength when it is made into a polymer.

Moreover, the case is also preferable, where it is represented by —Z$^2$=Z$^3$— or —Z$^4$=Z$^5$—. Concretely, groups of in the above formula (16), (17), (18), (19), or (20) are exemplified.

Among them, preferable is the case where $A^1$ is O—C(=O), O—C (R$^1$)(R$^2$), N(R$^5$)—C(=O), or N=C(R$^9$).

As the compounds represented by formula (5), compounds represented by the below (25) and (26) are exemplified.

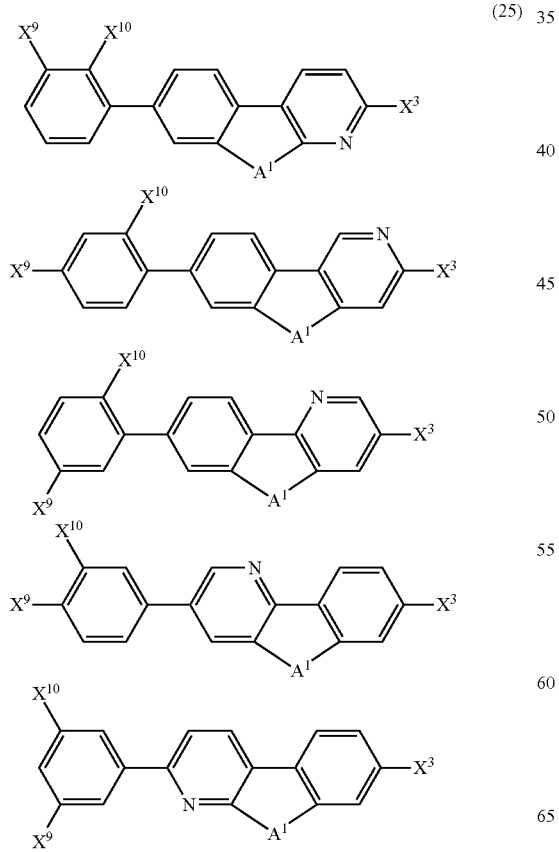

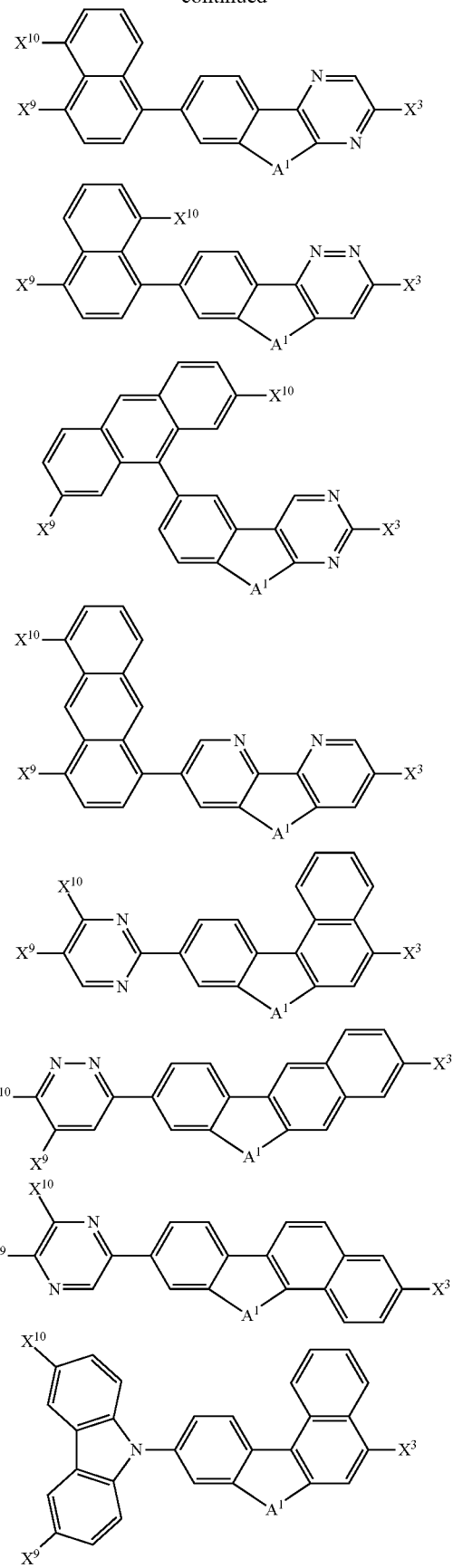

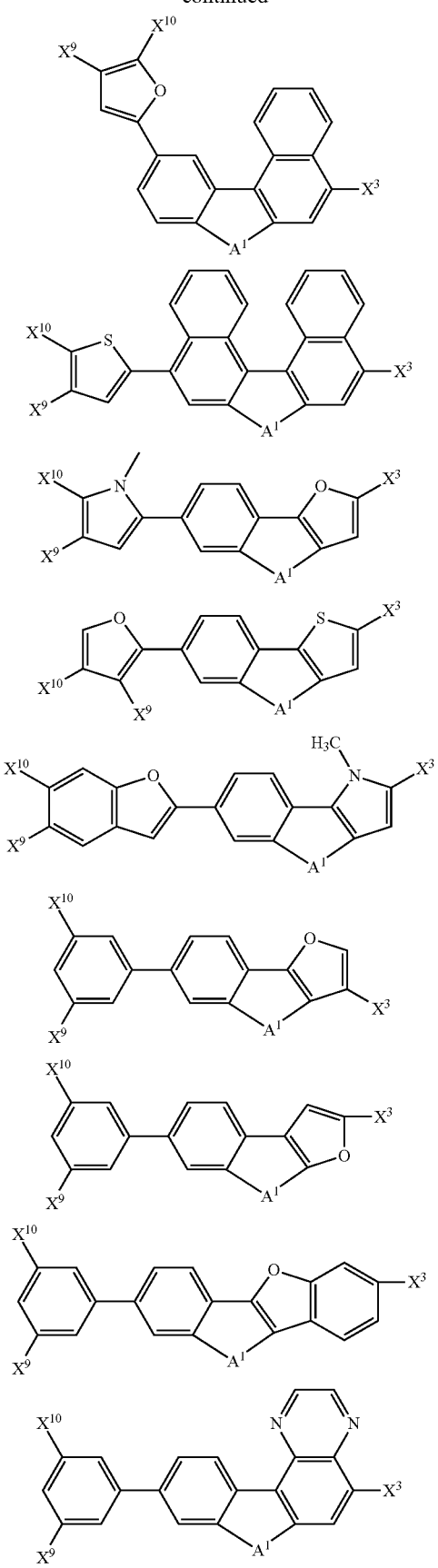
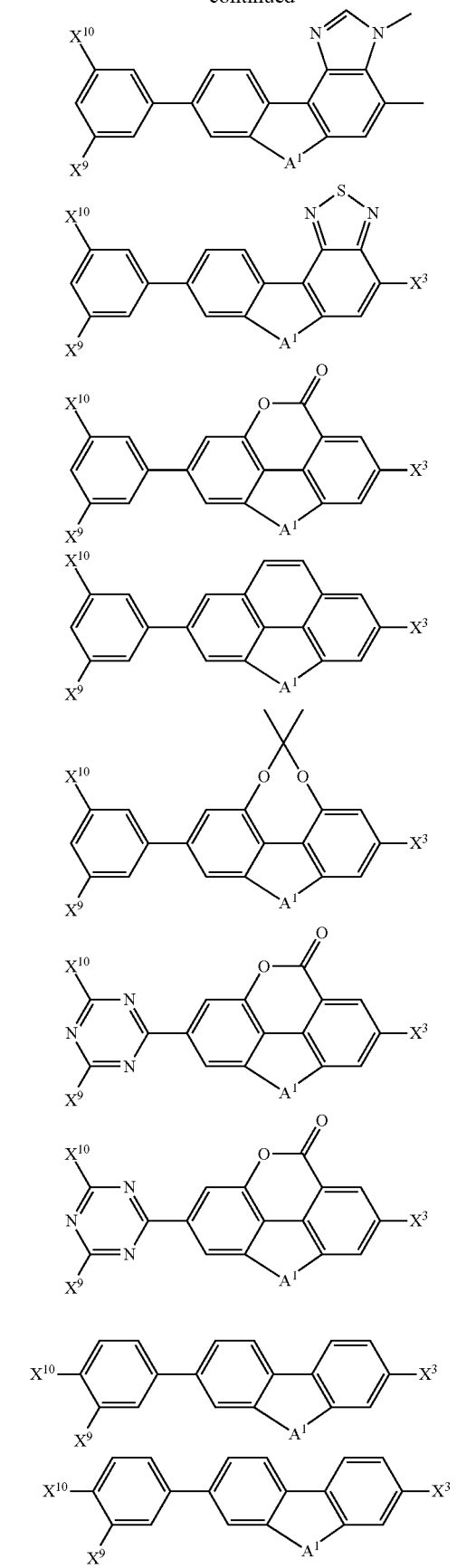
(26)

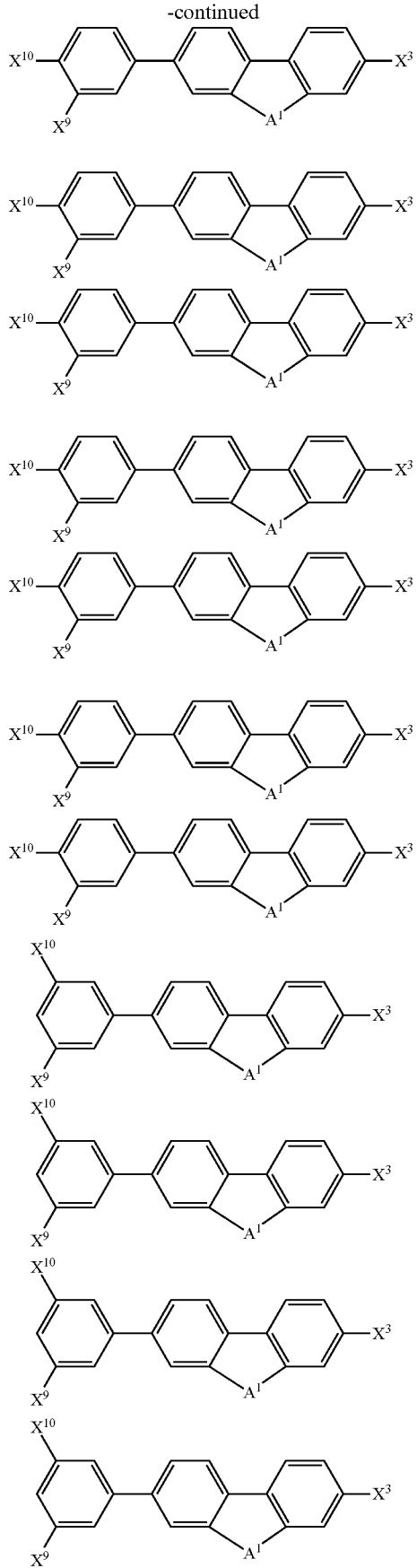
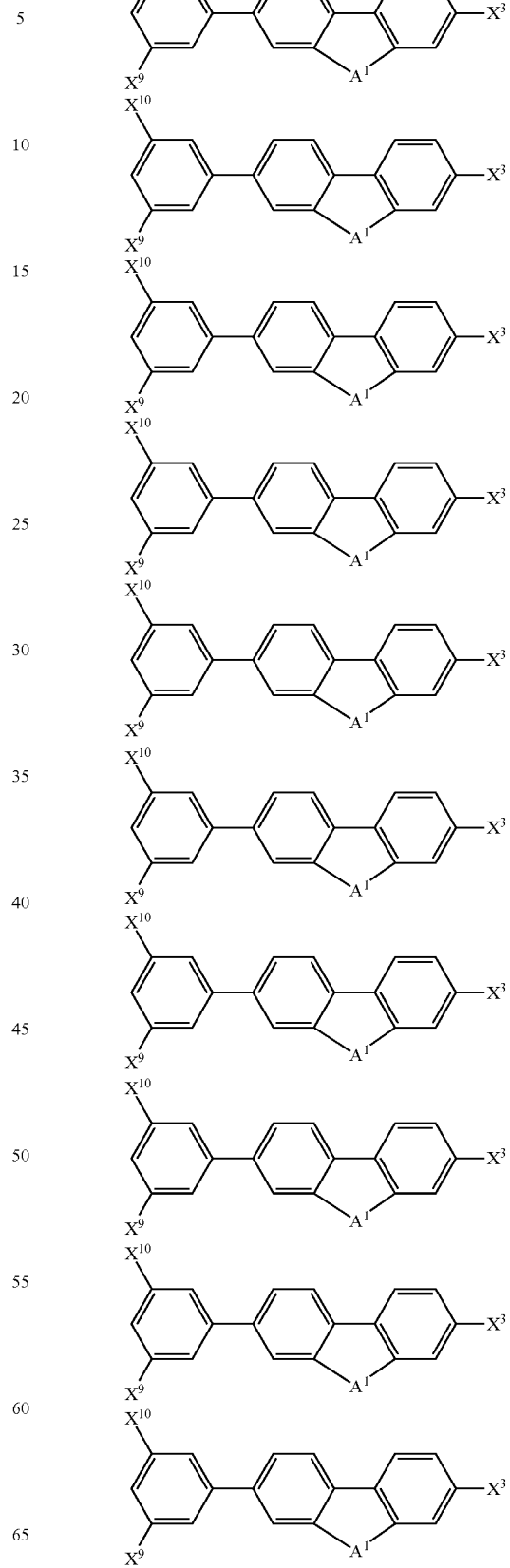

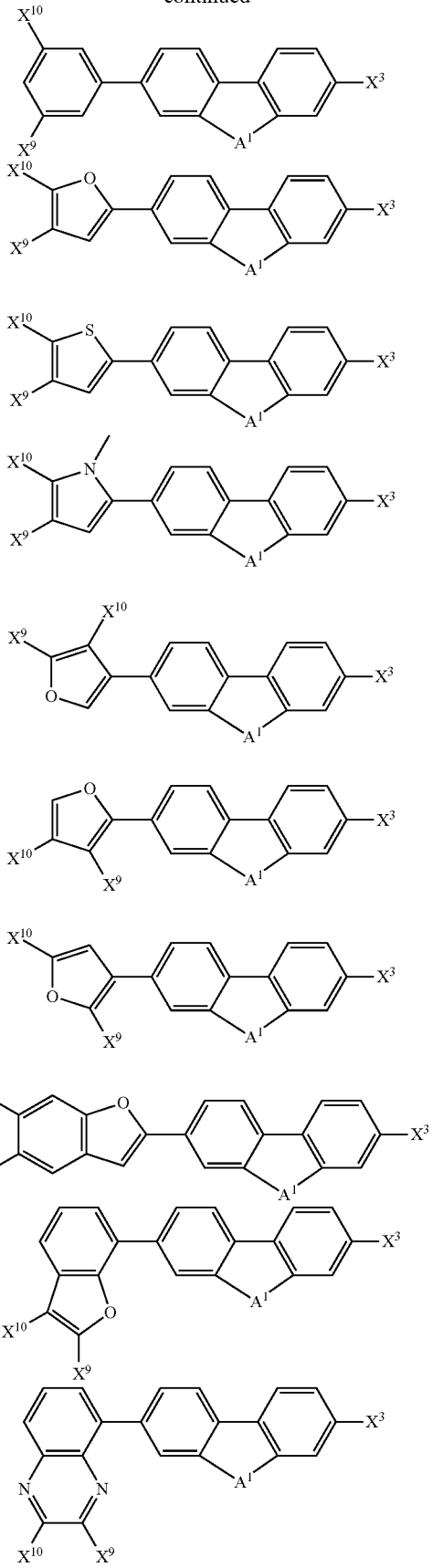
As the compounds represented by formula (6), compounds represented by the below (27) and (28) are exemplified.
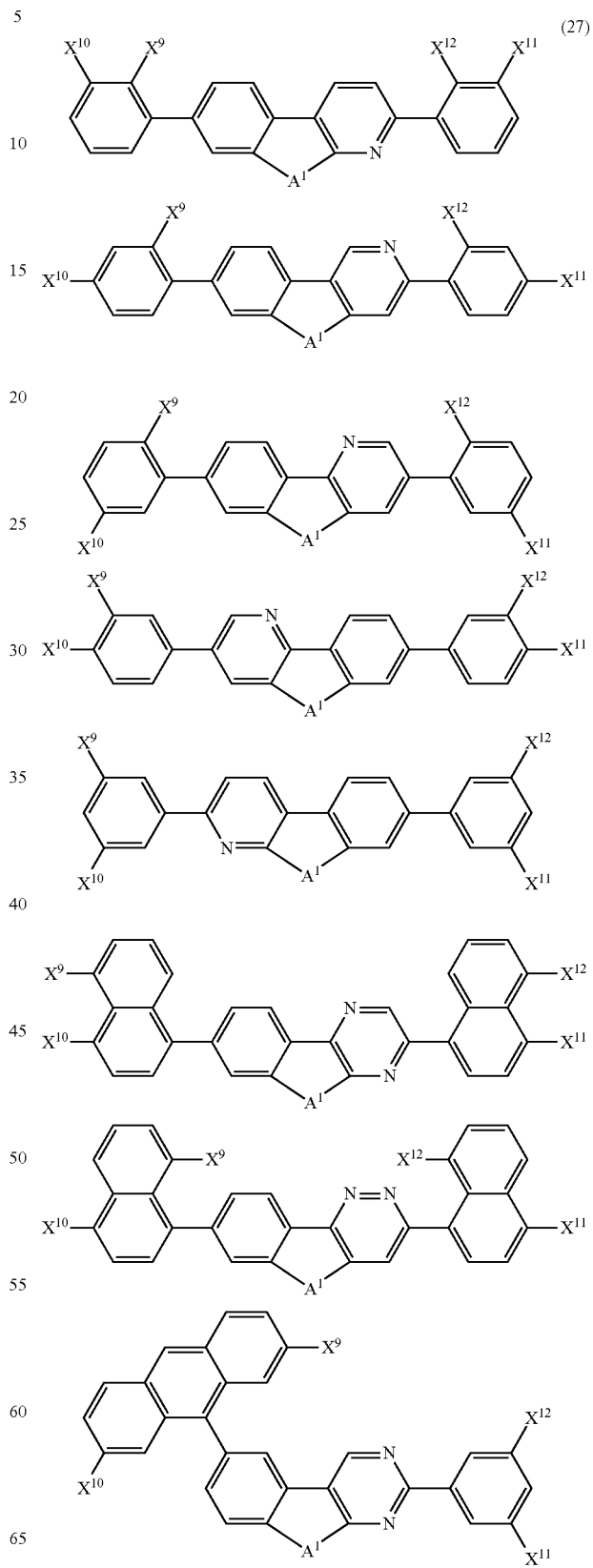

-continued
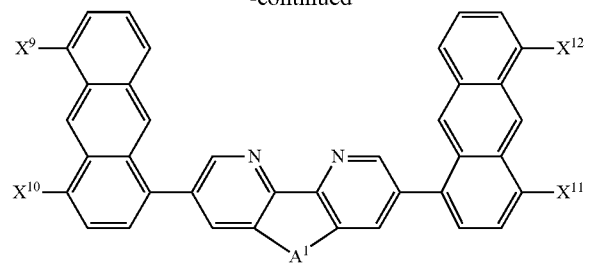
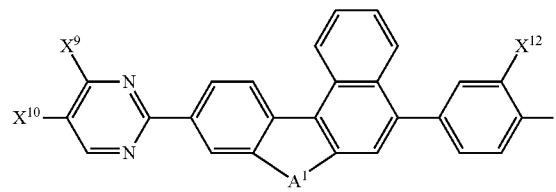
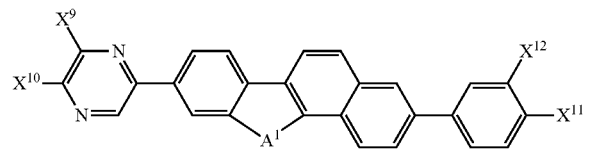
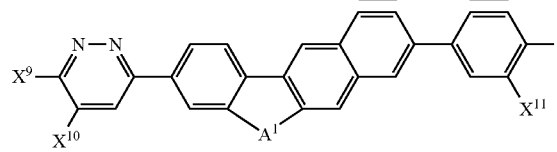
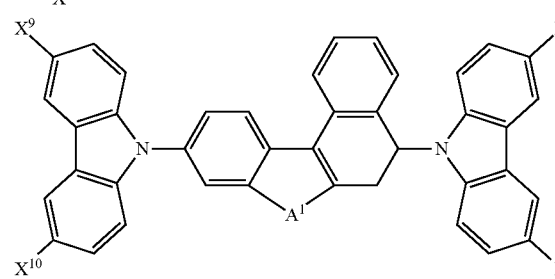
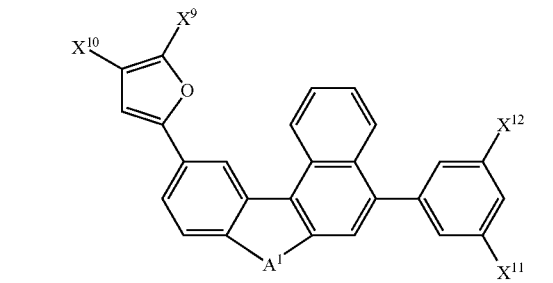
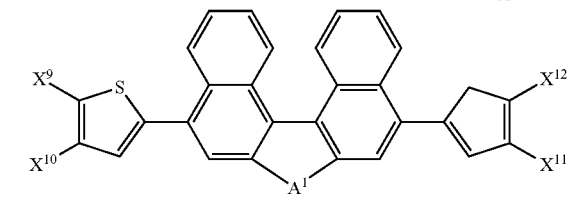
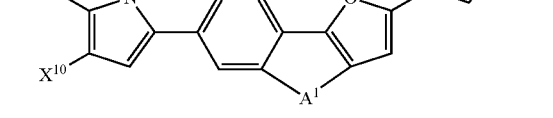
-continued
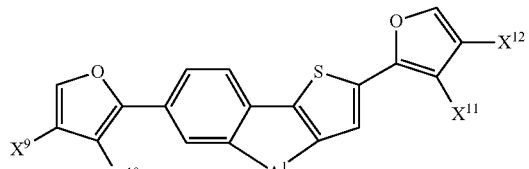
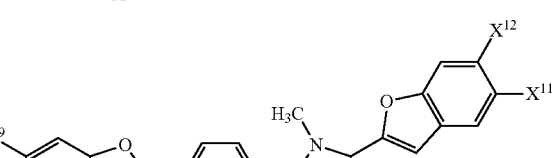
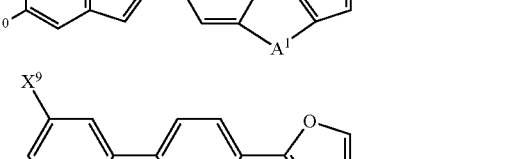
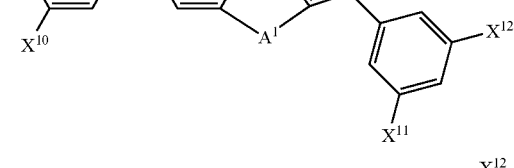
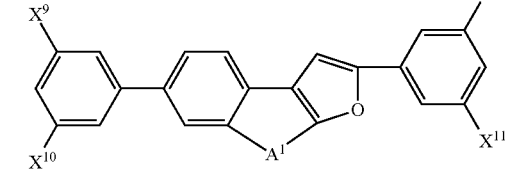
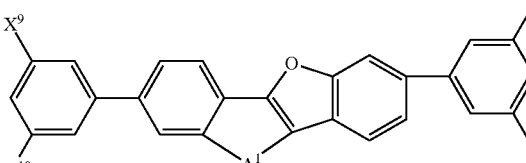
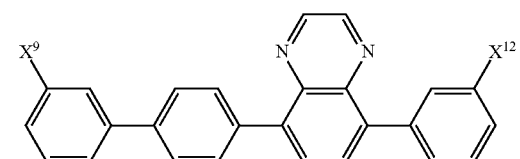
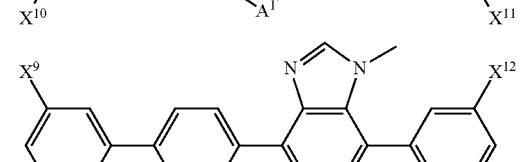
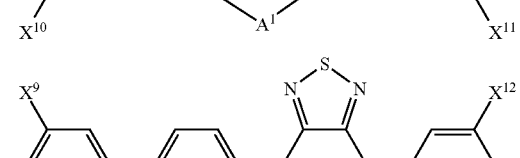
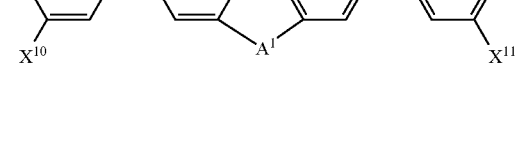

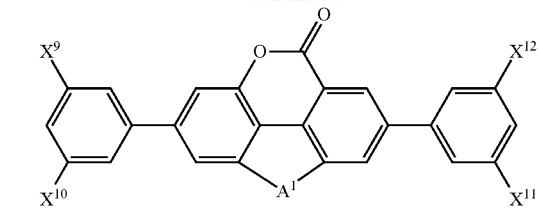
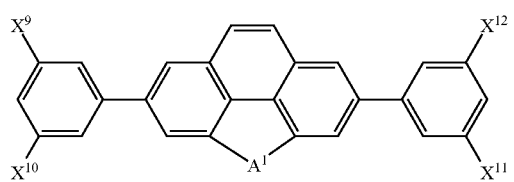
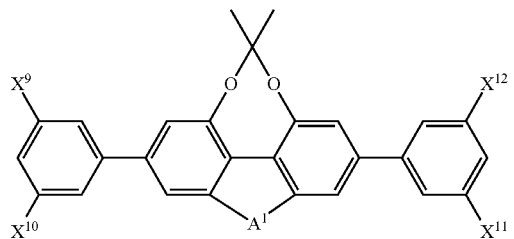
(28)
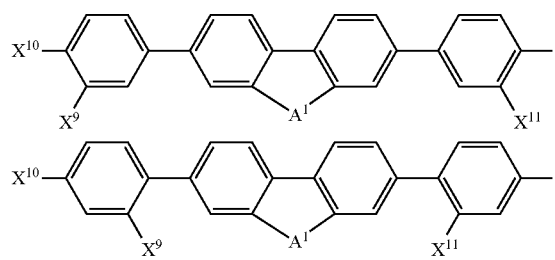
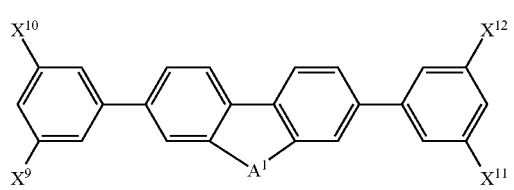
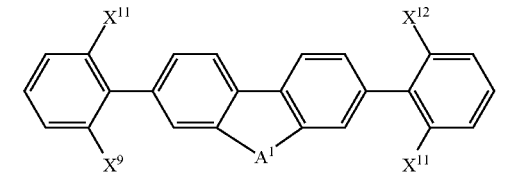
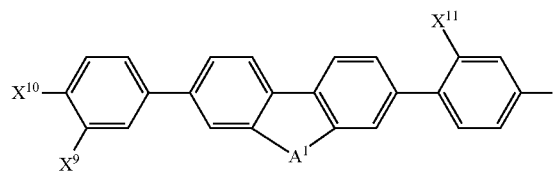
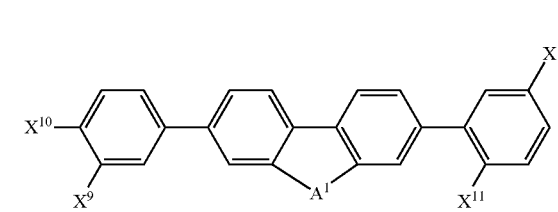
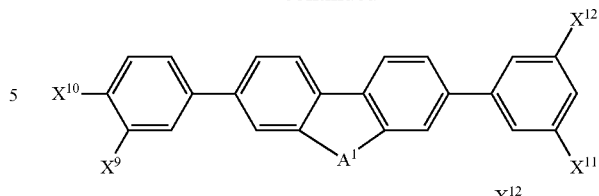
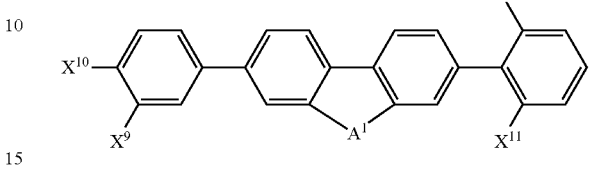
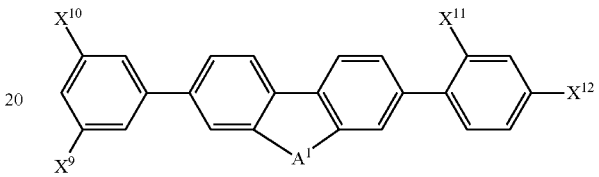
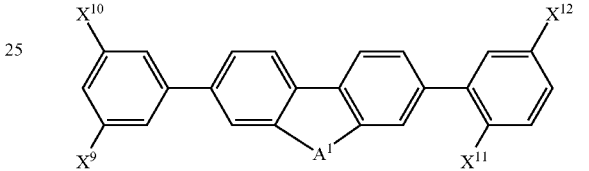
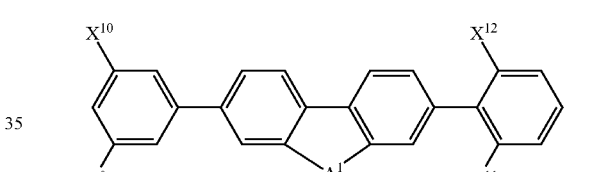
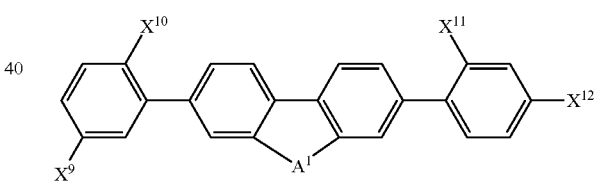
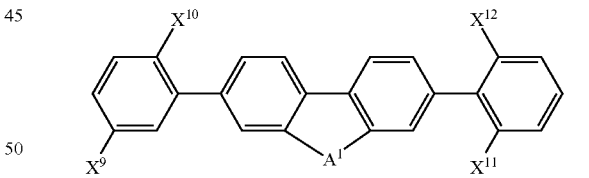
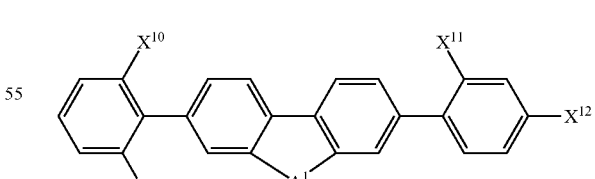
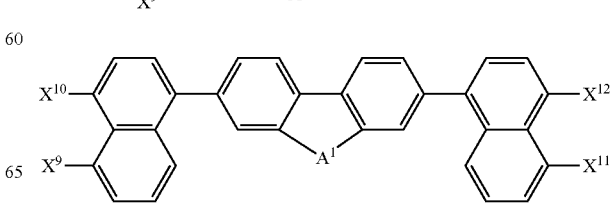

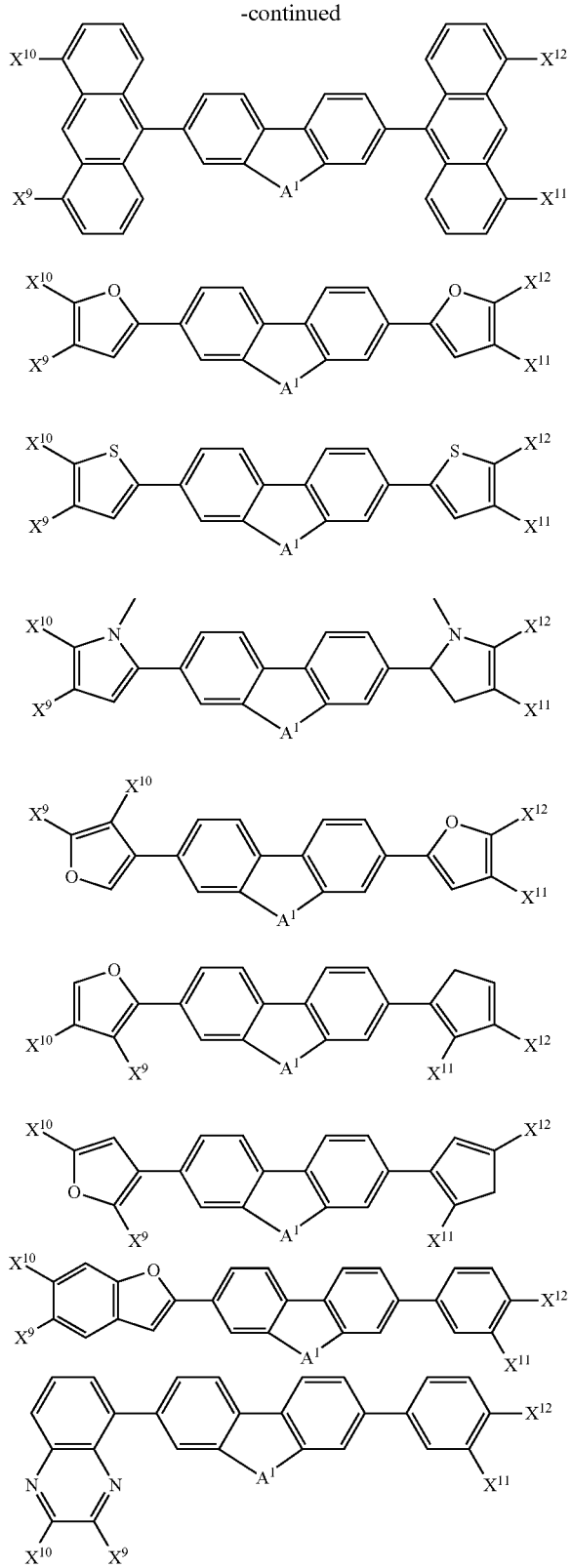

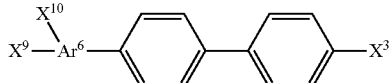

(5-1)

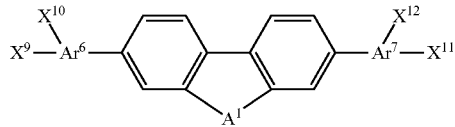

(6-1)

Wherein, $Ar^6$, $Ar^7$, $A^1$, $X^3$, $X^9$, $X^{10}$, $X^{11}$ and $X^{12}$ are the same as those of the above. Substituents may be carried on the benzene ring, and the substituents may be connected mutually to form a ring. Examples of the substituents include an alkyl group, alkyloxy group, alkylthio group, aryl group, aryloxy group, arylthio group, arylalkyl group, arylalkyloxy group, arylalkylthio group, acyl group, acyloxy group, amide group, acid imide group, imine residue, amino group, substituted amino group, substituted silyl group, substituted silyloxy group, substituted silylthio group, substituted silylamino group, monovalent heterocyclic group, hetero aryloxy group, hetero arylthio group, arylalkenyl group, arylethynyl group, carboxyl group, alkyloxy carbonyl group, aryloxy carbonyl group, arylalkyloxy carbonyl group, hetero aryloxy carbonyl group, and cyano group.

Next, compounds represented by formula (5) are described.

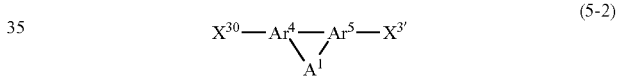

(5-2)

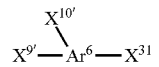

(5-3)

The compound represented by the above formula (5) can be manufactured by a method, wherein a cross-coupling of one equivalent amount of a compound represented by the above formula (5-2) with a compound represented by (5-3) is conducted, then $X^{3'}$, $X^{9'}$ and $X^{10'}$ are respectively converted to $X^3$, $X^9$, and $X^{10}$. Wherein, $A^1$, $Ar^4$, $Ar^5$, and $Ar^6$ represent the same meaning as described above. $X^{3'}$, $X^{9'}$, and $X^{10'}$ each independently represent a halogen atom, alkylsulfonate group, arylsulfonate group, arylalkylsulfonate group, boric ester group, —$B(OH)_2$, monohalogenated-methyl group, sulfonium-methyl group, phosphonium-methyl group, phosphonate-methyl group, cyano methyl group, formyl group, vinyl group, or a functional group which can be converted into a halogen atom, alkylsulfonate group, arylsulfonate group, arylalkylsulfonate group, boric ester group, —$B(OH)_2$, monohalogenated-methyl group, sulfonium-methyl group, phosphonium-methyl group, phosphonate-methyl group, cyano methyl group, formyl group, or vinyl group. $X^{30}$ and $X^{31}$ each independently represent a halogen atom, alkylsulfonate group, arylsulfonate group, arylalkylsulfonate group, trialkyltin group, boric ester group, or —$B(OH)_2$.

As the method of cross-coupling, Suzuki coupling, Grignard coupling, Stille coupling, etc. are exemplified. As the functional groups convertible into $X^9$ and $X^{10}$, for example, exemplified are hydroxyl group, alkyloxy group, acyloxy group, substituted silyloxy group, amino group, or nitro Among them, preferable is the case where $A^4$ and $A^5$ in the above formula (5) or (6) are aromatic hydrocarbons, in view of stability of the compounds.

Especially the case represented by the below formula (5-1) or (6-1), it is preferable in view of stability of the compounds.

group. The method of functional-group conversion is as above. The synthetic method is exemplified below.

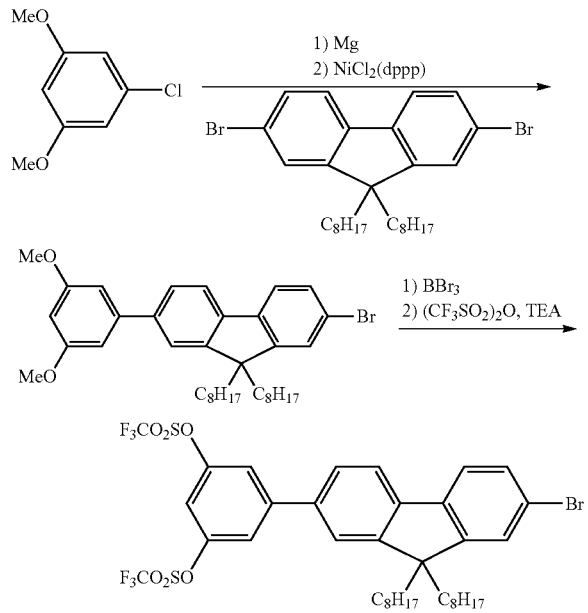

Next, the synthetic method the compound represented by formula (6) is described.

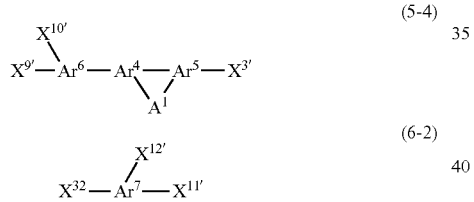

$$X^{9'}\!-\!Ar^6\!-\!Ar^4\!-\!Ar^5\!-\!X^{3'} \quad (5\text{-}4)$$
(with $X^{10'}$ on $Ar^4$, $A^1$ branch)

$$X^{32}\!-\!Ar^7\!-\!X^{11'} \quad (6\text{-}2)$$
(with $X^{12'}$)

The compound represented by the above formula (6) can be manufactured for example by a method, wherein a cross-coupling of a compound represented by the above formula (5-4) with a compound represented by (6-2) is conducted, then $X^{9'}$, $X^{10'}$, $X^{11'}$ and $X^{12'}$ are respectively converted to $X^9$, $X^{10}$, $X^{11}$ and $X^{12}$. As the method of cross-coupling, the same method as described above is exemplified. Moreover, the compound represented by (6) can be manufactured by a method, wherein a compound represented by a compound represented by (5-2) with two equivalents amount of a compound represented by (5-3) is reacted, then $X^{9'}$ and $X^{10'}$ are respectively converted to $X^9$ and $X^{10}$.

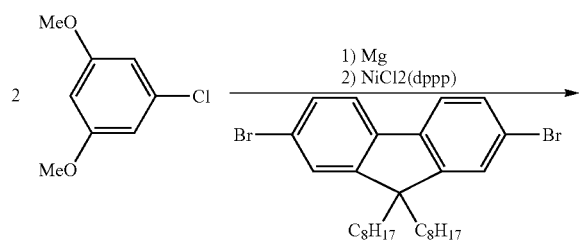

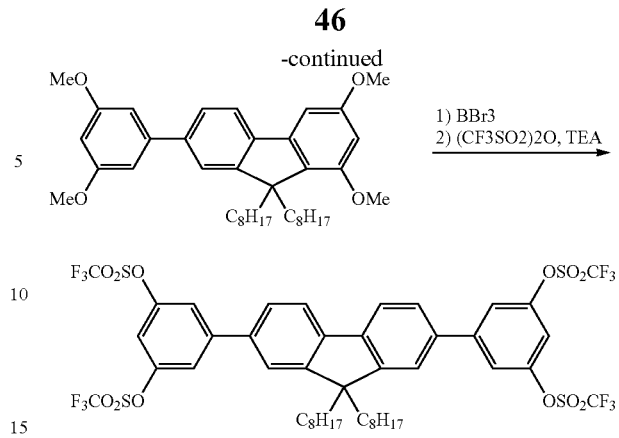

Next, compounds represented by formula (9), (10), or (11) are described.

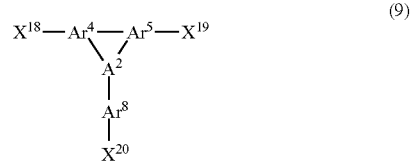
(9)

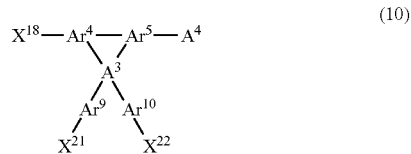
(10)

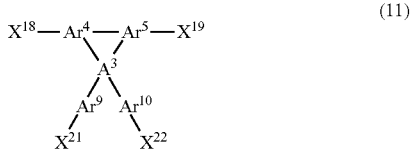
(11)

Wherein, $Ar^4$ and $Ar^5$ represent the same meaning as described above, and $Ar^8$, $Ar^9$ and $Ar^{10}$ each independently represent an arylene group or a divalent heterocyclic group. Said $Ar^4$, $Ar^5$, $Ar^8$, $Ar^9$ and $Ar^{10}$ may have a substituent. When $Ar^4$ and $Ar^5$ have substituents, they may be connected to form a ring, and When $Ar^9$ and $Ar^{10}$ have substituents, they may be connected to form a ring, and moreover, $Ar^8$ and $Ar^{10}$ may be connected directly to form a ring.

The aryl group is an atomic group in which one hydrogen atom is removed from an aromatic hydrocarbon, and the number of carbon atoms is usually 6 to 60, preferably 6 to 20. The aromatic hydrocarbon group may have a substituent, but the number of carbon atoms of the substituent is not counted as the number of carbon atoms of the aromatic hydrocarbon group. As the aromatic hydrocarbon compound and substituent, examples of those represented for the trivalent aromatic hydrocarbon group in the above formula (1).

The divalent heterocyclic group is an atomic group in which two hydrogen atoms are removed from a heterocyclic compound, and the number of carbon atoms is usually 3 to 60, preferably 3 to 20. The heterocyclic group may have a substituent. As the heterocyclic compound and substituent, examples of those represented for the trivalent aromatic hydrocarbon group in the above formula (1).

Wherein, $A^2$ is represented by any one of the below formulas.

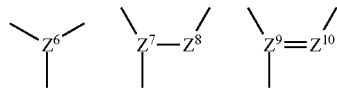

Wherein, $Z^6$ represents B, P, or P(=O). $Z^7$ represents $C(R^9)$, $Si)(R^{10}$, N, B, P or P(=O). $Z^8$ represents O, S, C(=O), S(=O), $SO_2$, $C(R^1)(R^2)$, $Si(R^3)(R^4)$, $N(R^5)$, $B(R^6)$, $P(R^7)$, or P(=O) $(R^8)$. $Z^9$ represents C or Si. $Z^{10}$ represents N, B, P, $C(R^9)$ or $Si(R^{10})$. (Wherein, $R^1$, $R^2$, $R^3$, $R^4$, $R^5$, $R^6$, $R^7$, $R^8$, $R^9$ and $R^{10}$ represent the same meaning as described above.)

$A^3$ is represented by any one of the below formulas.

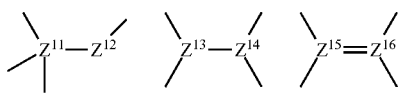

Wherein, $Z^{11}$ represents C or Si. $Z^{12}$ represents O, S, C(=O), S(=O), $SO_2$, $C(R^1)(R^2)$, $Si(R^3)(R^4)$, $N(R^5)$, $B(R^6)$, $P(R^7)$ or P(=O) $(R^8)$. $Z^{13}$ and $Z^{14}$ each independently represent $C(R^9)$, $Si(R^{10})$, B, N, P or P(=O). $Z^{15}$ and $Z^{16}$ each independently represent C or Si. (Wherein, $R^1$, $R^2$, $R^3$, $R^4$, $R^5$, $R^6$, $R^7$, $R^8$, $R^9$ and $R^{10}$ represent the same meaning as described above.)

$A^4$ represents a hydrogen atom, alkyl group, alkyloxy group, alkylthio group, aryl group, aryloxy group, arylthio group, arylalkyl group, arylalkyloxy group, arylalkylthio group, substituted amino group, substituted silyl group, monovalent heterocyclic group, hetero aryloxy group, hetero arylthio group, arylalkenyl group or arylethynyl group. However, in formula (9), $Ar^5$ and $A^2$ are connected to mutually adjacent atoms of $Ar^4$ ring, and $Ar^4$ and $A^2$ are connected to mutually adjacent atoms of $Ar^5$ ring.

Wherein, $X^{18}$, $X^{19}$, $X^{20}$, $X^{21}$ and $X^{22}$ each independently represent a halogen atom, alkylsulfonate group, arylsulfonate group, arylalkylsulfonate group, boric ester group, —B(OH)$_2$, monohalogenated-methyl group, sulfonium-methyl group, phosphonium-methyl group, phosphonate-methyl group, Cyano methyl group, formyl group, vinyl group, hydroxyl group, alkyloxy group, acyloxy group, substituted silyloxy group, amino group, or nitro group. At least one of $X^{18}$, $X^{19}$ and $X^{20}$ in formula (9) is selected from a halogen atom, alkylsulfonate group, arylsulfonate group, arylalkylsulfonate group, boric ester group, —B(OH)$_2$, monohalogenated-methyl group, sulfonium-methyl group, phosphonium-methyl group, phosphonate-methyl group, cyano methyl group, formyl group and vinyl group. At least one of $X^{18}$, $X^{21}$ and $X^{22}$ in formula (10) is selected from a halogen atom, alkylsulfonate group, arylsulfonate group, arylalkylsulfonate group, boric ester group, —B(OH)$_2$, monohalogenated-methyl group, sulfonium-methyl group, phosphonium-methyl group, phosphonate-methyl group, cyano methyl group, formyl group and vinyl group, At least one of $X^{18}$, $X^{19}$, $X^{21}$ and $X^{22}$ in formula (11) is selected from a halogen atom, alkylsulfonate group, arylsulfonate group, arylalkylsulfonate group, boric ester group, —B(OH)$_2$, monohalogenated-methyl group, sulfonium-methyl group, phosphonium-methyl group, phosphonate-methyl group, cyano methyl group, formyl group and vinyl group.

As the group represented by $A^2$, groups shown below are specifically exemplified.

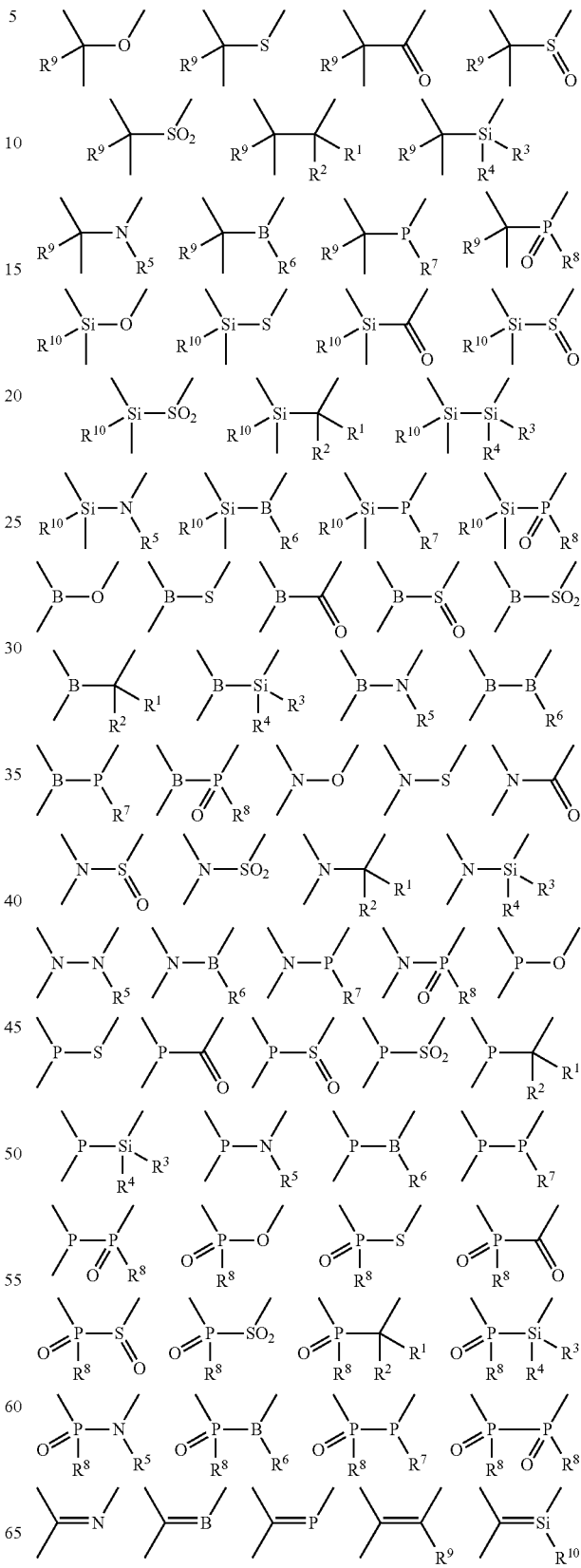

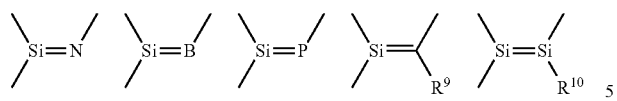

As the group represented by $A^3$, groups shown below are specifically exemplified.

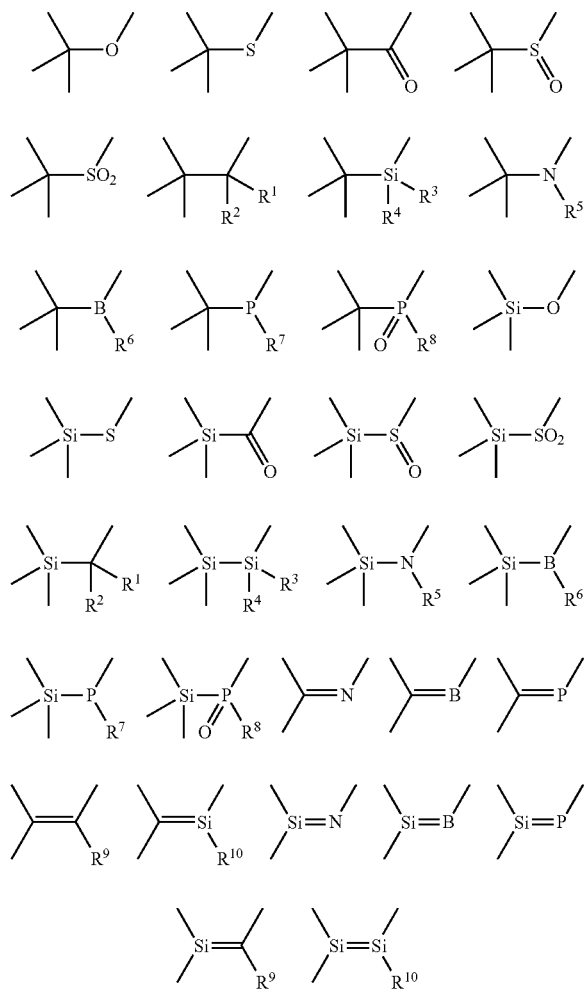

When the compounds represented by the above formula (9), (10) or (11) have a condensation reactive functional group and a condensation reactive functional-group precursor, after carrying out a condensation reaction, by condensation reactive functional-group precursor being converted into a functional-group, and further performing a condensation reaction, it becomes possible to perform a regio-selective substituent introduction and a polymerization reaction.

When the compounds represented by the above formula (9), (10) or (11) have a condensation reactive functional group and a condensation reactive functional-group precursor, preferable is the case where $A^2$ is B, P, or P(=O) in view of the light-emitting strength when this compound is made into a polymer.

The case where $A^2$ is represented by the below formulas is also preferable.

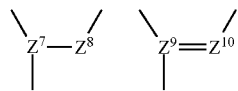

Wherein, $Z^7$, $Z^8$, $Z^9$ and $Z^{10}$ represent the same meaning as described above.

As for the compounds represented by the above formula (10) or (11), preferable is the case where $A^3$ is a tetravalent group shown below, in view of the light-emitting strength when it is made into a polymer.

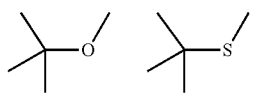

Moreover, preferable are the cases where: all of $X^{18}$, $X^{19}$ and $X^{20}$ in formula (9) are selected from a halogen atom, alkylsulfonate group, arylsulfonate group, arylalkylsulfonate group, boric ester group, —B(OH)$_2$, monohalogenated-methyl group, sulfonium-methyl group, phosphonium-methyl group, phosphonate-methyl group, cyano methyl group, formyl group and vinyl group; and all of $X^{18}$, $X^{21}$ and $X^{22}$ in formula (10) are selected from a halogen atom, alkylsulfonate group, arylsulfonate group, arylalkylsulfonate group, boric ester group, —B(OH)$_2$, monohalogenated-methyl group, sulfonium-methyl group, phosphonium-methyl group, phosphonate-methyl group, cyano methyl group, formyl group, and vinyl group; and all of $X^{18}$, $X^{19}$, $X^{21}$ and $X^{22}$ in formula (11) are selected from a halogen atom, alkylsulfonate group, arylsulfonate group, arylalkylsulfonate group, boric ester group, —B(OH)$_2$, monohalogenated-methyl group, sulfonium-methyl group, phosphonium-methyl group, phosphonate-methyl group, cyano methyl group, formyl group, and vinyl group; since it gives a branched polymer by serving it directly to a polymerization.

Among them, preferable are the cases where: at least one of $X^{18}$, $X^{19}$ and $X^{20}$ in formula (9) is a different functional group from others; at least one of $X^{18}$, $X^{21}$ and $X^{22}$ in formula (10) is a different functional group from others; and at least one of $X^{18}$, $X^{19}$, $X^{21}$ and $X^{22}$ in formula (11) is a different functional group from others; since control of the reaction site of condensation reaction is possible.

Preferable is the case where $A^2$ is B, P, or P(=O), in view of the light-emitting strength when it is made into a polymer.

Moreover, the case where $A^2$ is represented by the below formulas, is preferable.

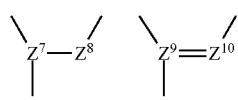

Wherein, $Z^7$, $Z^8$, $Z^9$, and $Z^{10}$ represent the same meaning as described above.

As for the compounds represented by the above formula (10) or (11), preferable is the case where $A^3$ is a tetravalent group shown below, in view of the light-emitting strength when it is made into a polymer.

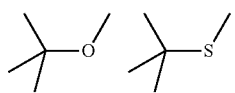
As the compounds represented by formula (9), groups shown by the below (29) and (30) are exemplified.
(29)
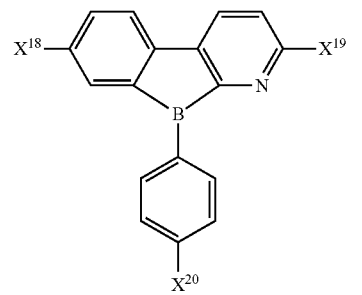
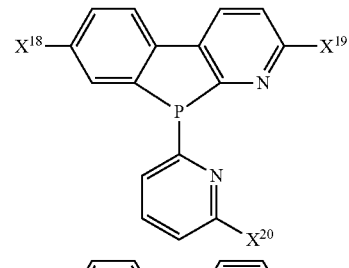
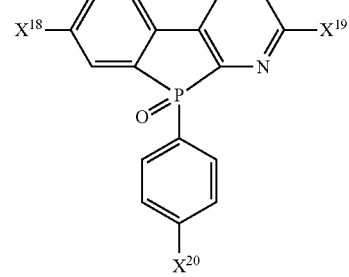
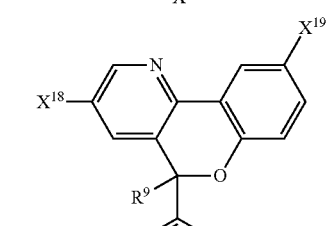
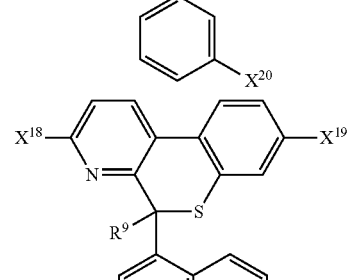
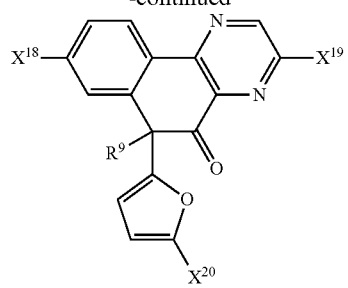
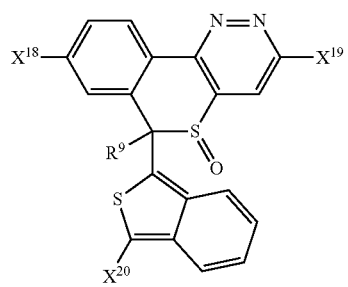
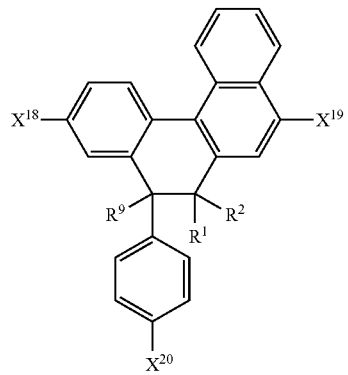
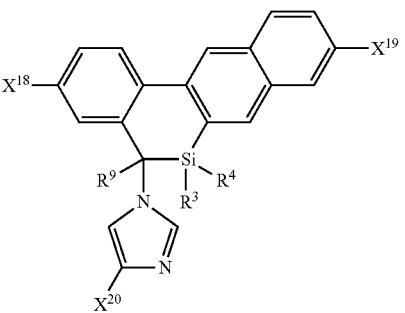
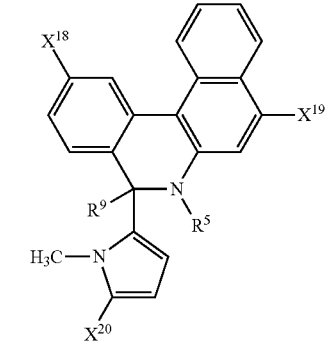

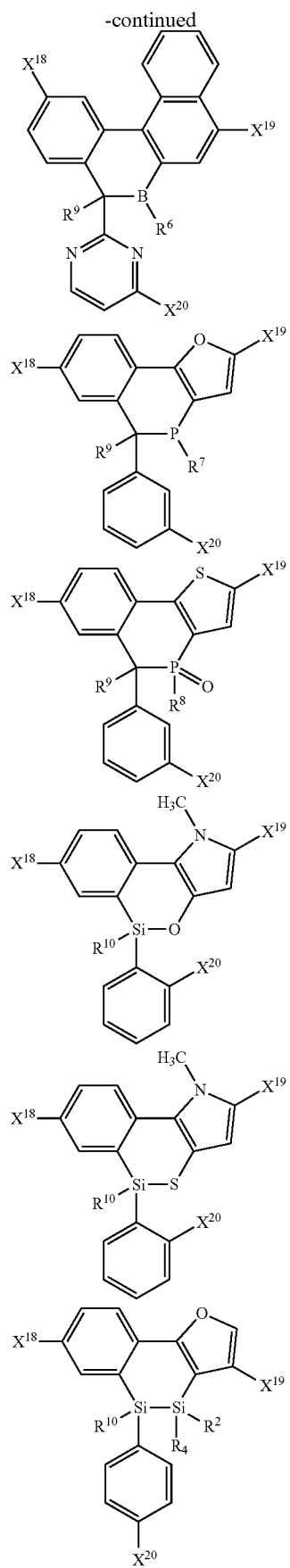
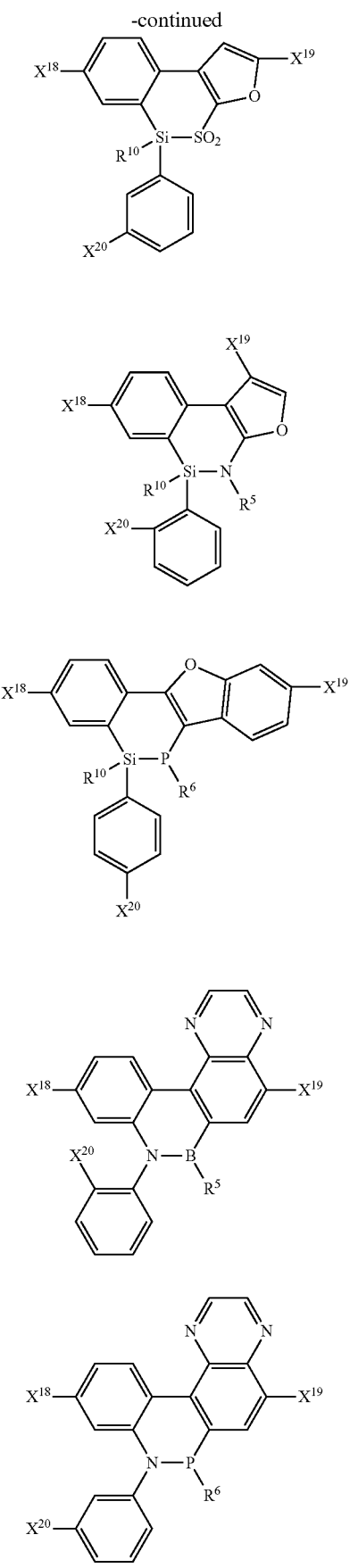

-continued
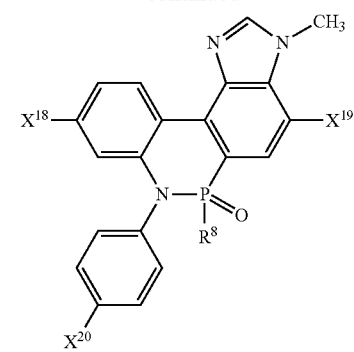
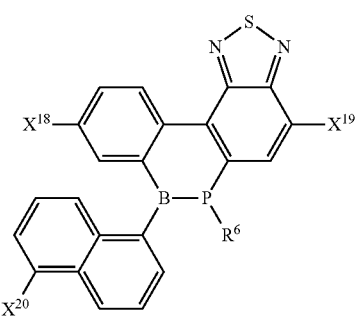
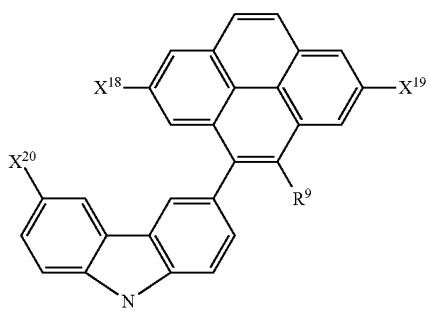
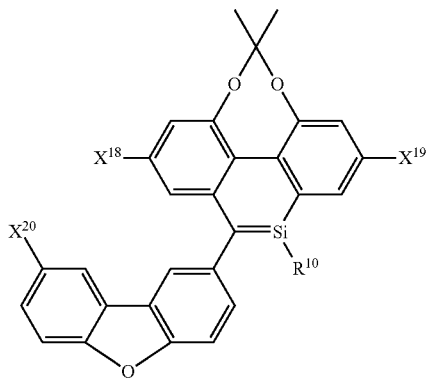
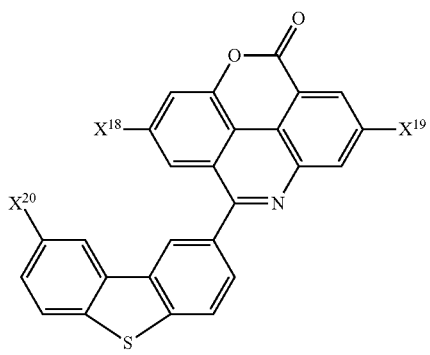
-continued
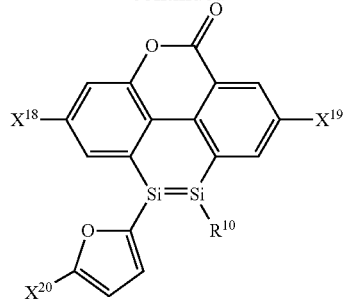
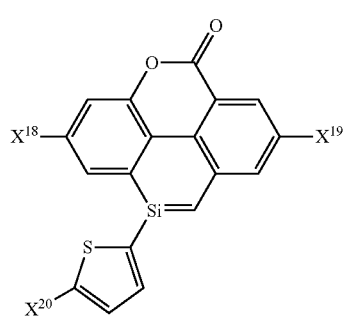
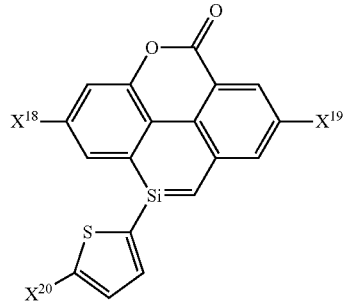
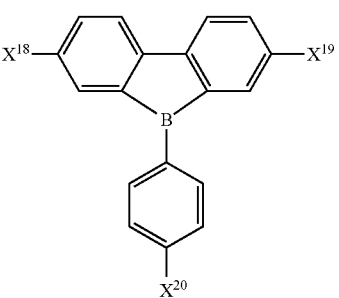
(30)
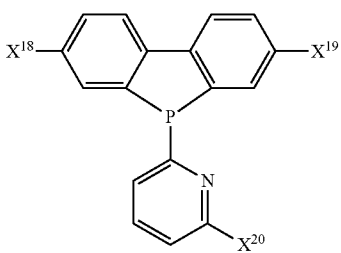

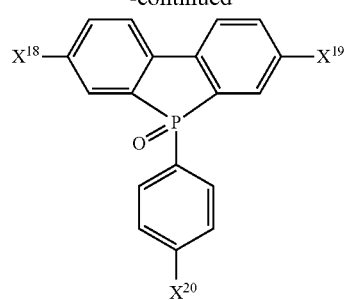
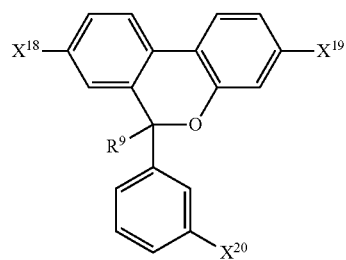
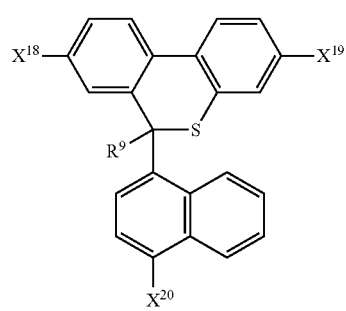
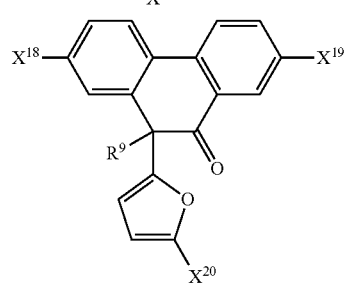
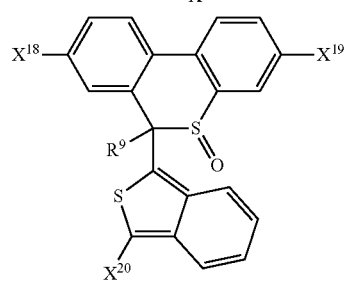
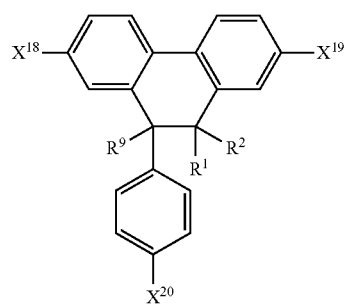
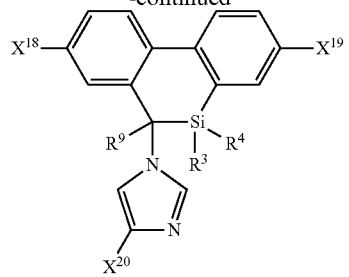
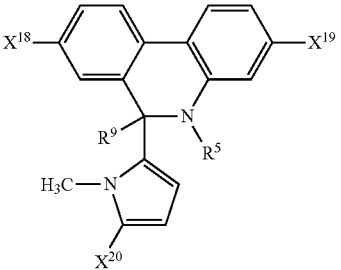
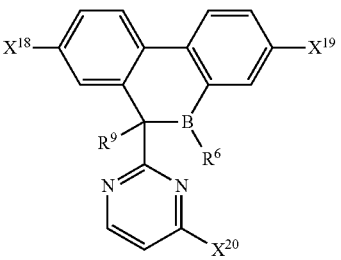
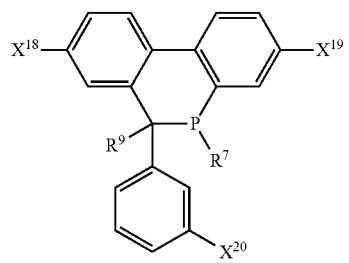
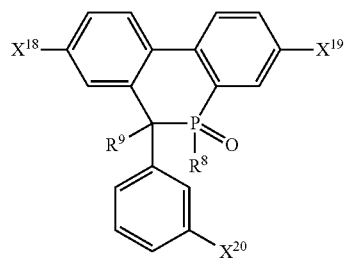
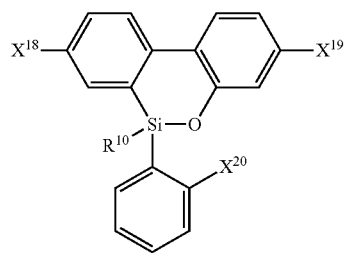

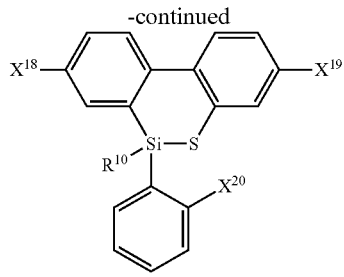
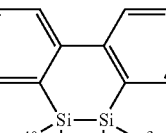
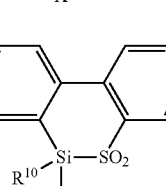
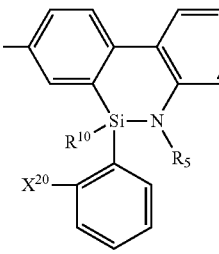
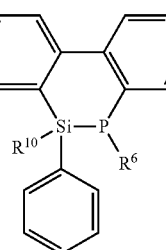
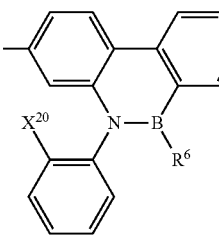
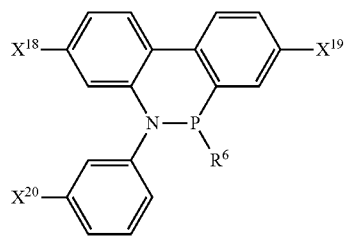
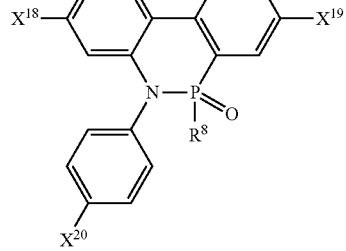
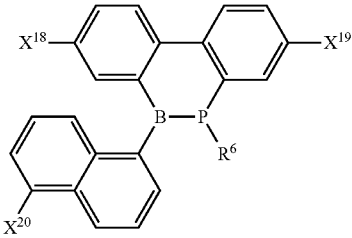
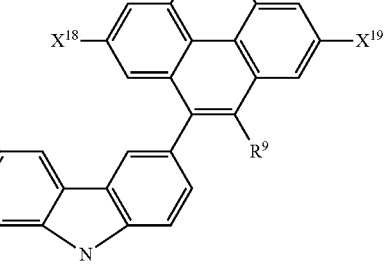
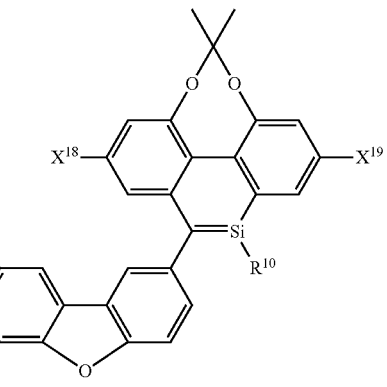

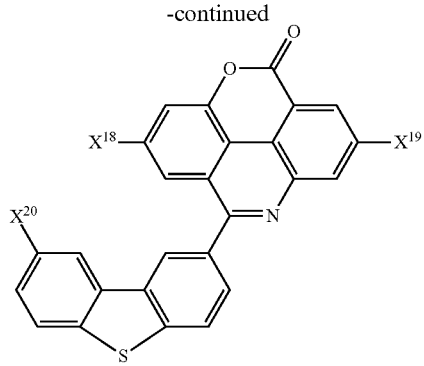
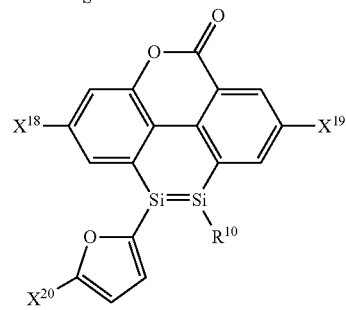
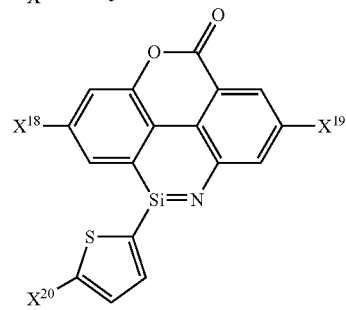
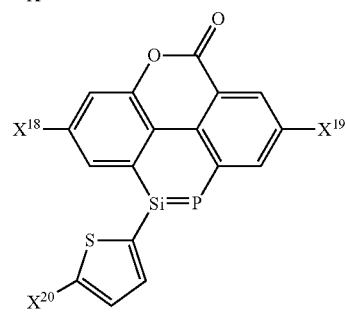
As the compounds represented by formula (10), groups shown by the below (31) and (32) are exemplified.
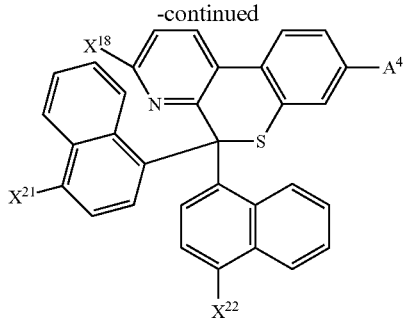
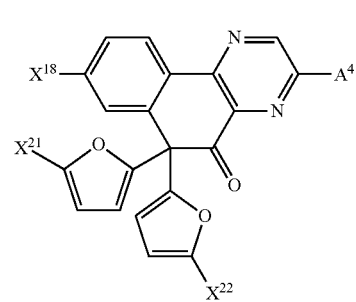
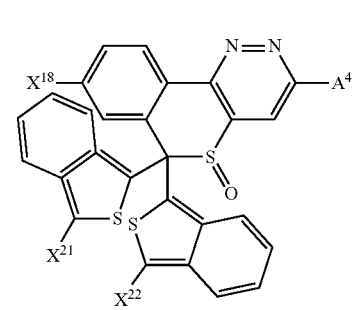
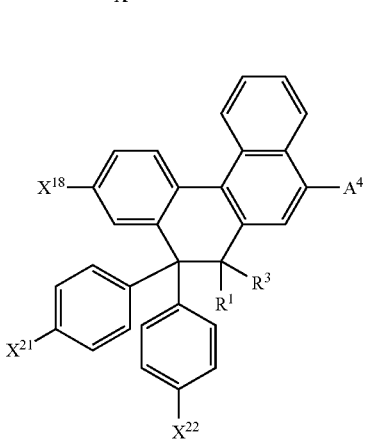
(31)
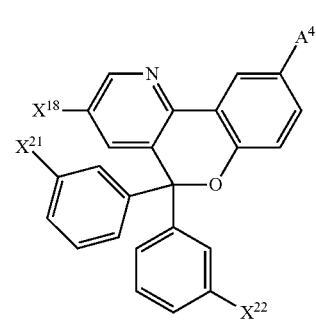
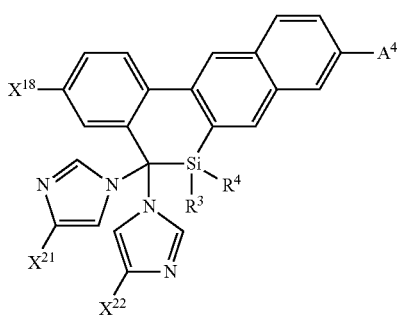

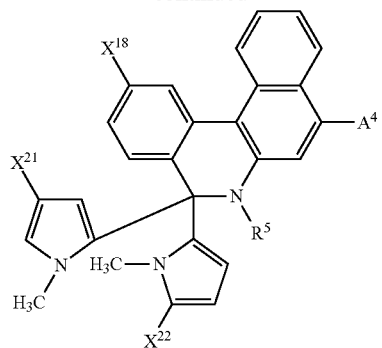
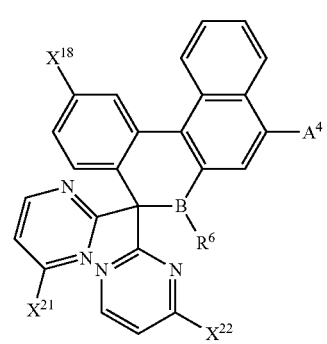
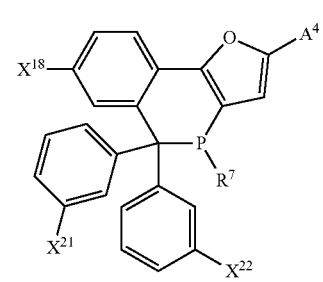
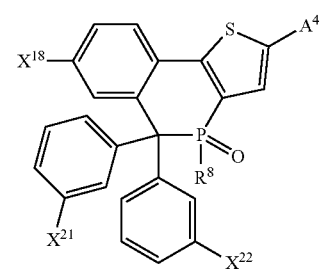
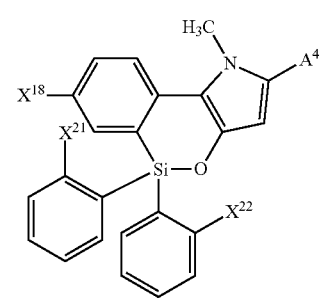
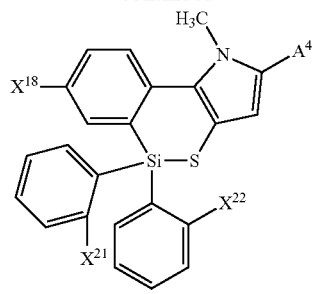
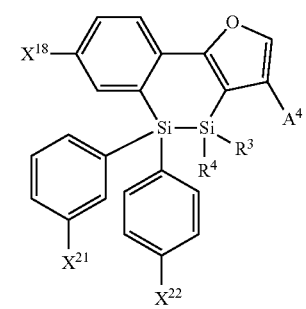
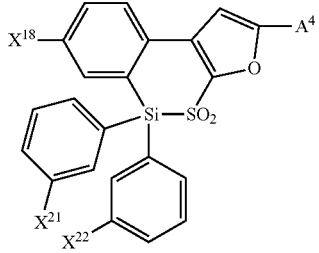
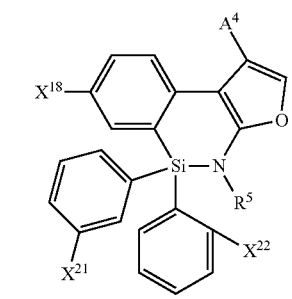
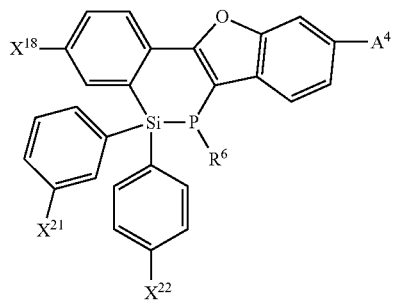

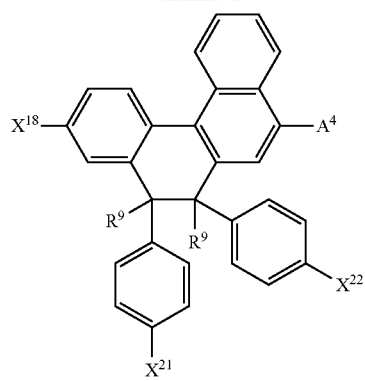
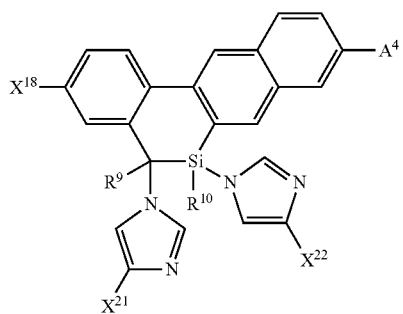
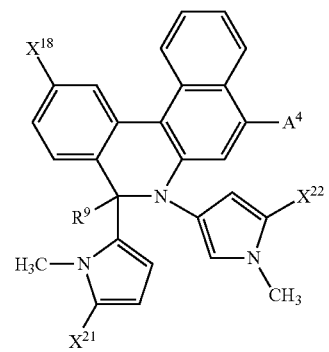
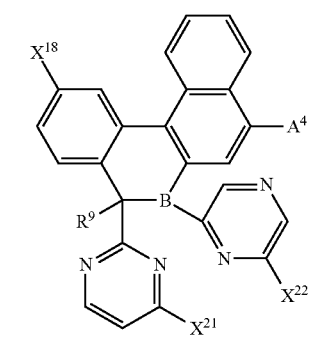
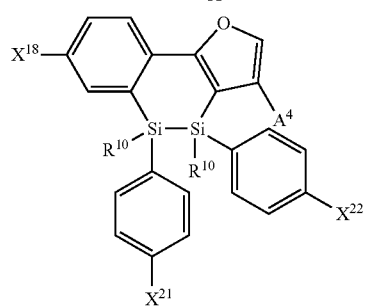
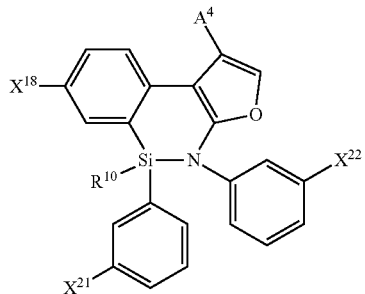
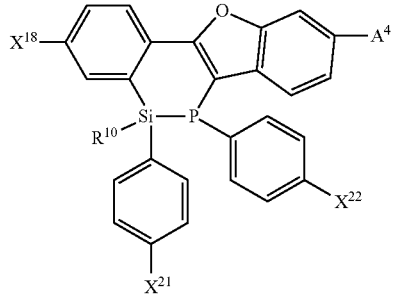
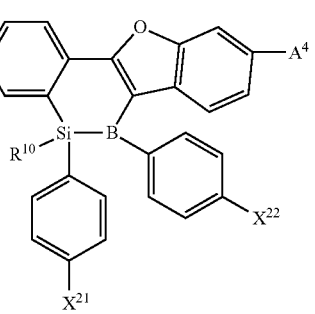
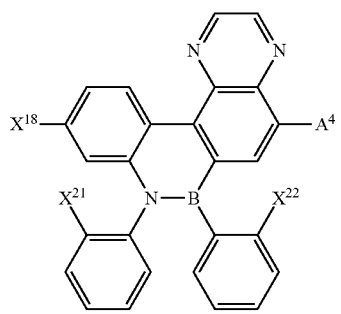
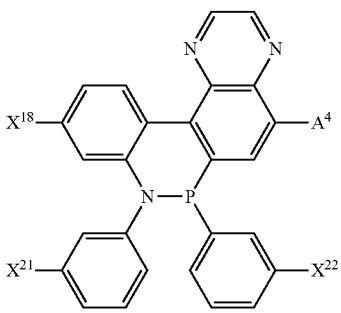

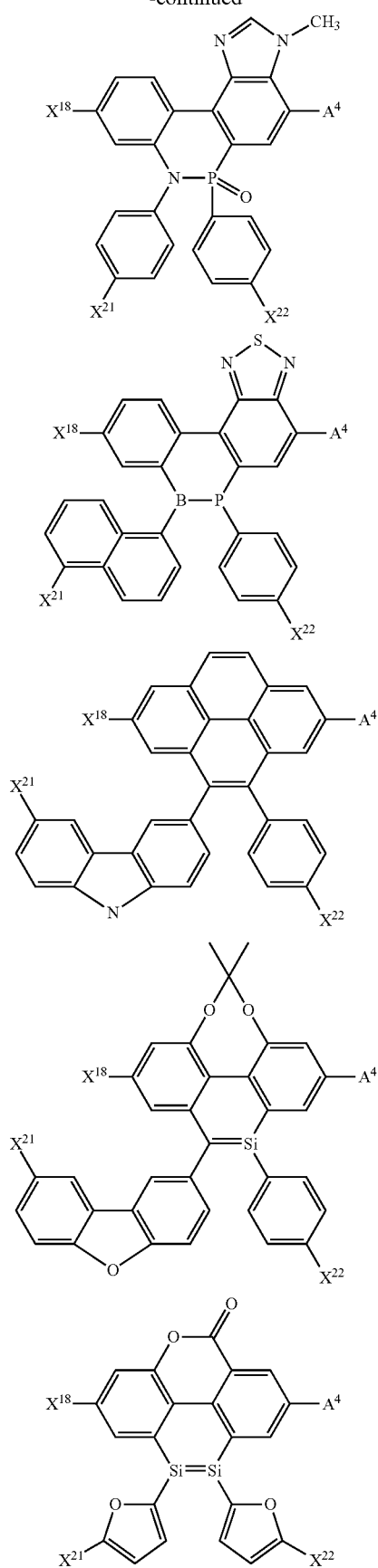
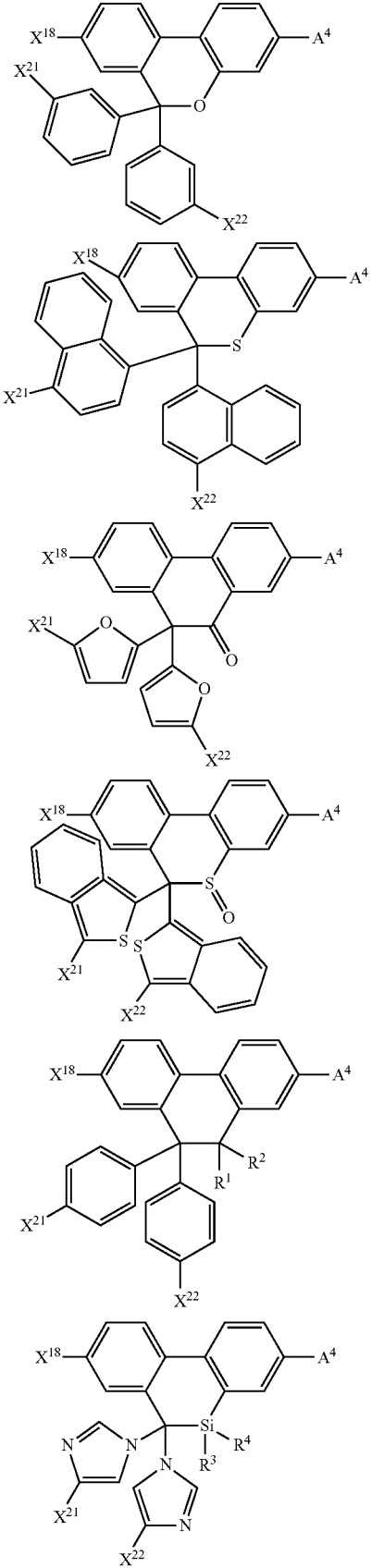

-continued
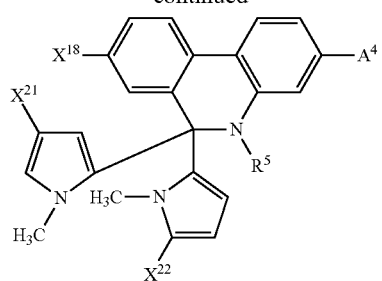
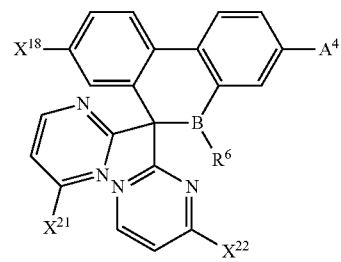
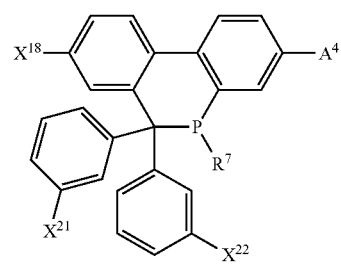
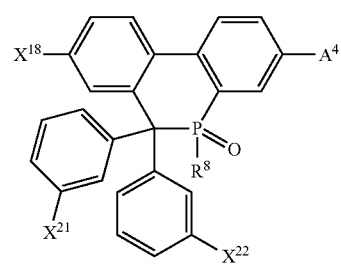
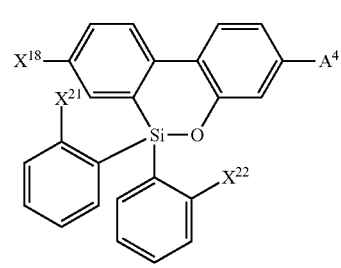
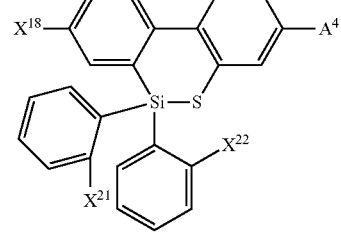
-continued
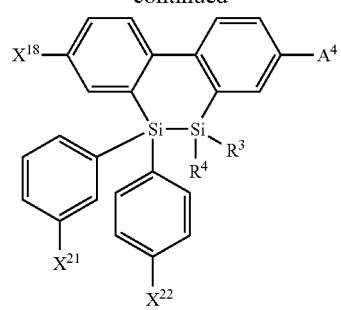
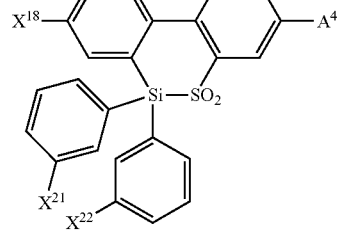
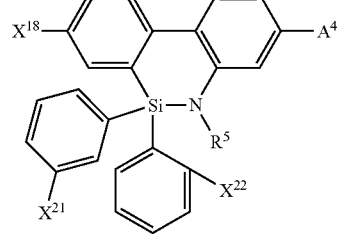
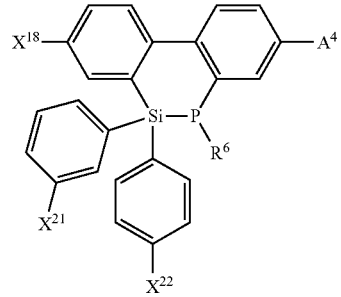
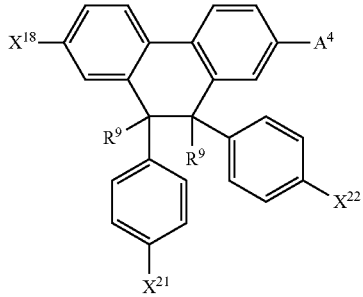
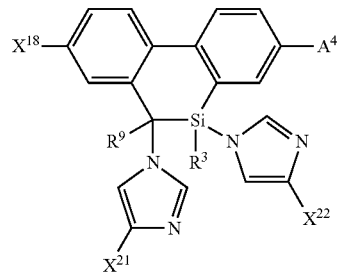

-continued
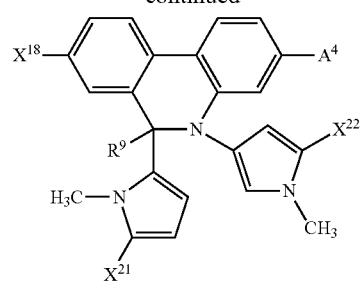
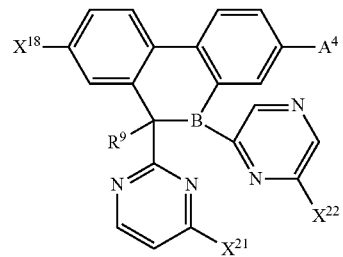
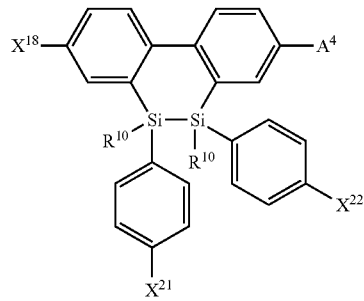
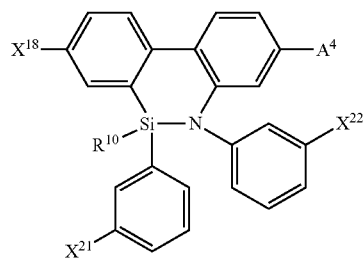
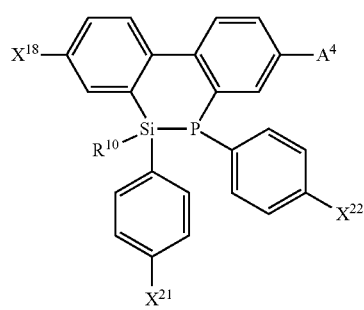
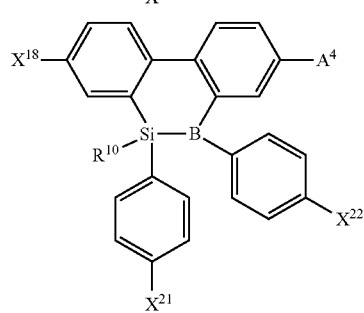
-continued
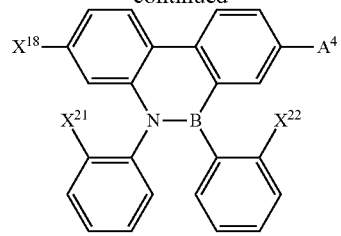
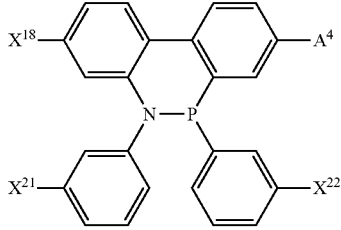
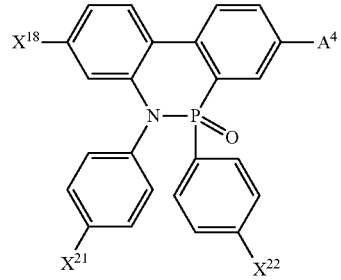
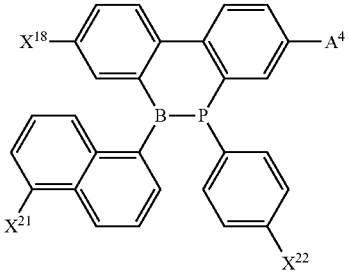
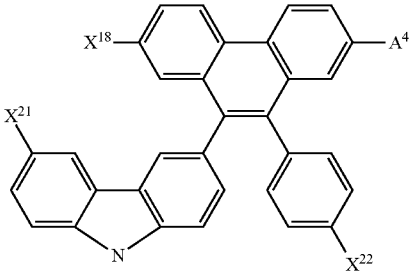
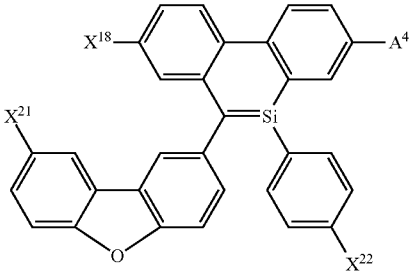

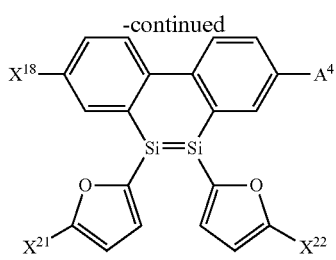
As the compounds represented by formula (11), groups shown by the below (33) and (34) are exemplified.
(33)
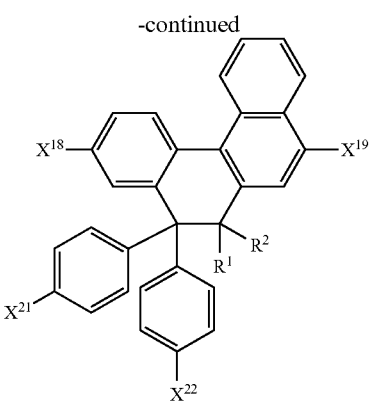
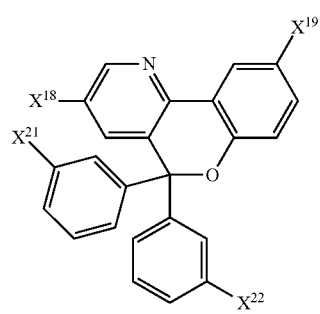
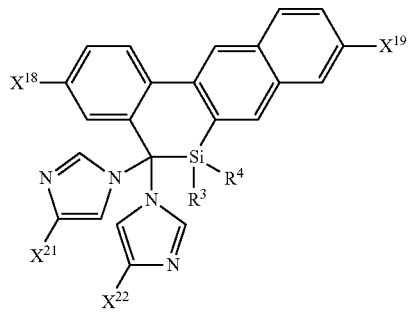
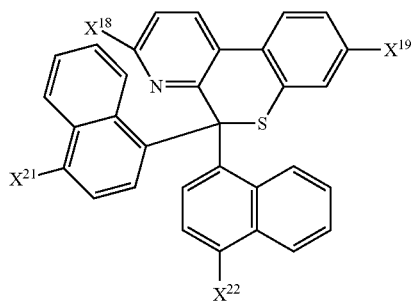
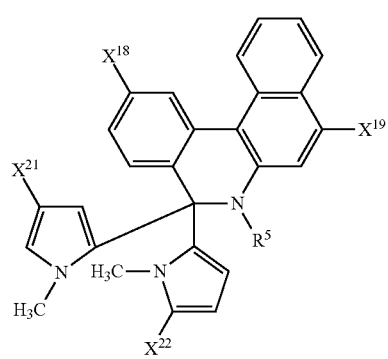
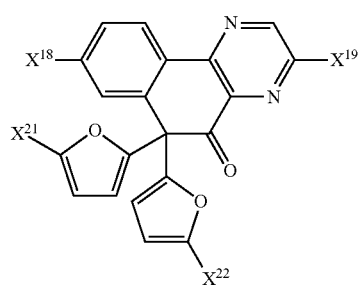
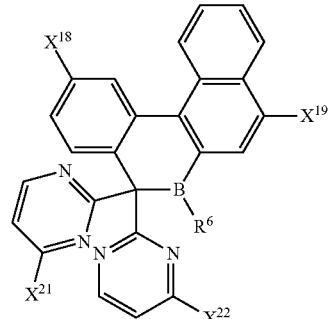
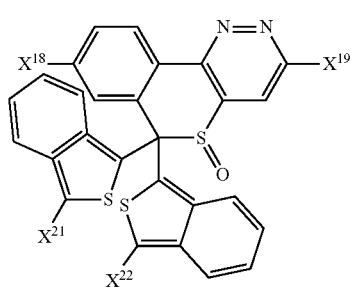
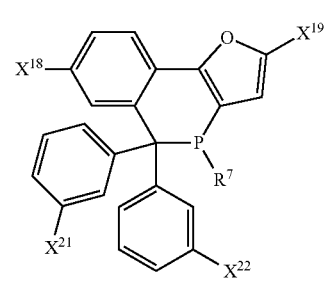

-continued
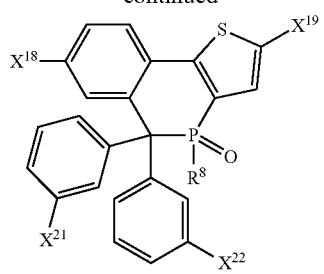
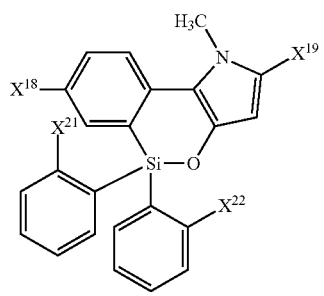
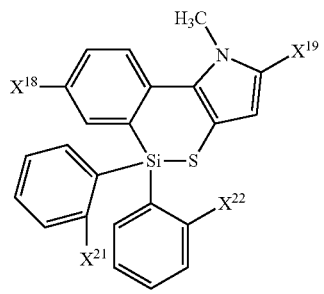
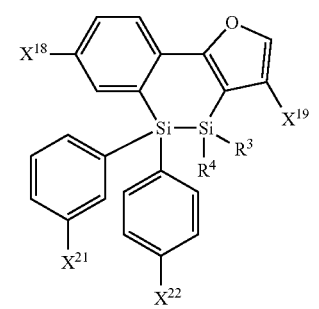
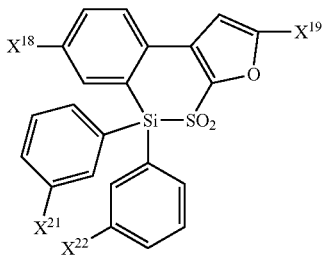
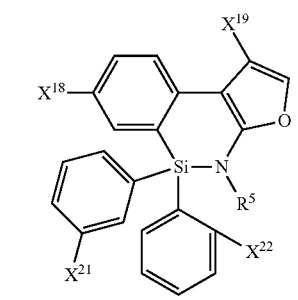
-continued
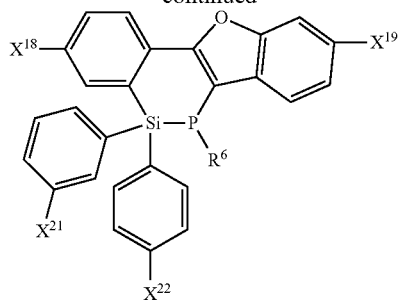
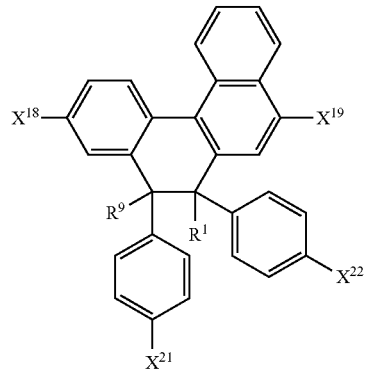
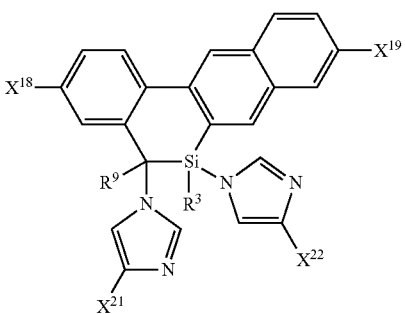
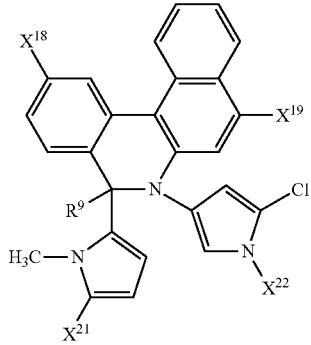
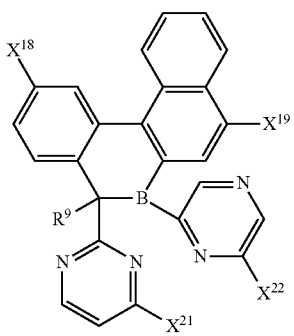

77
-continued
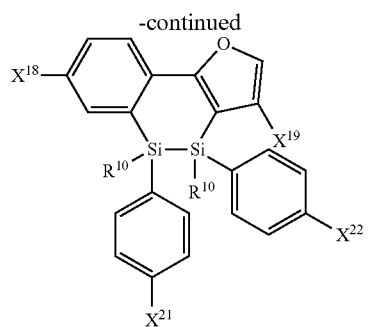
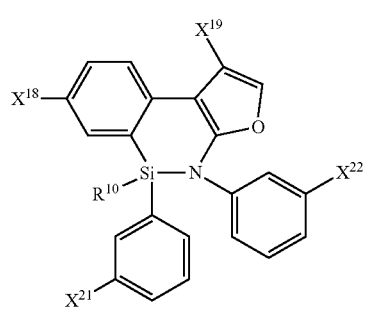
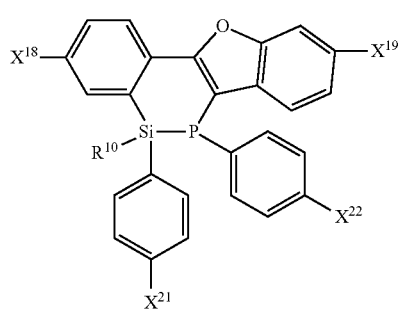
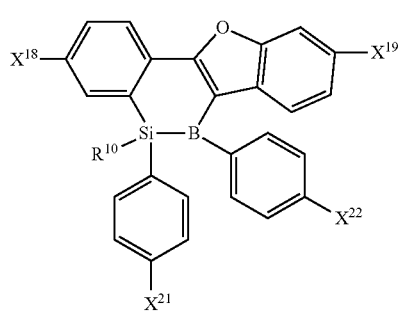
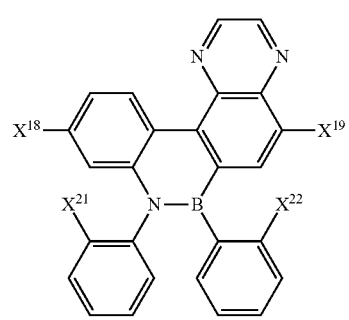
78
-continued
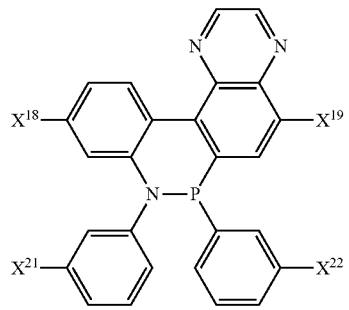
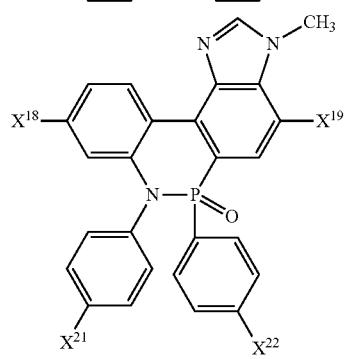
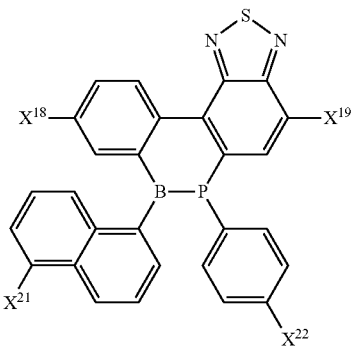
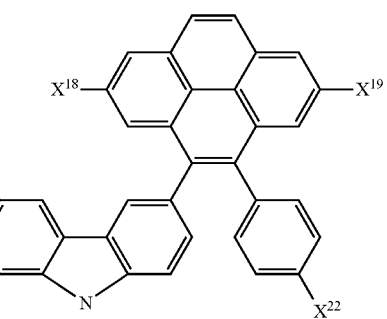
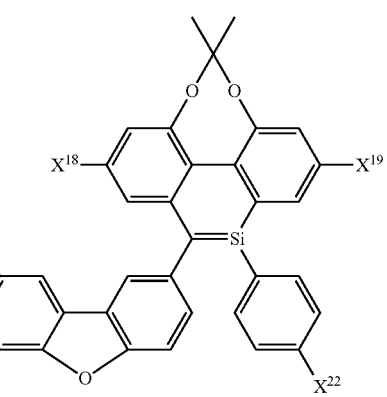

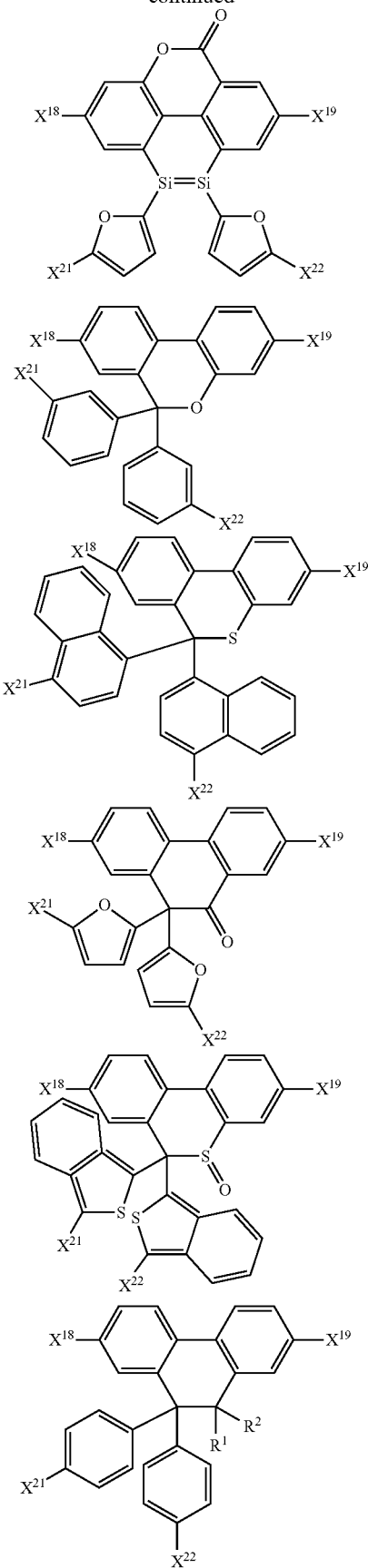
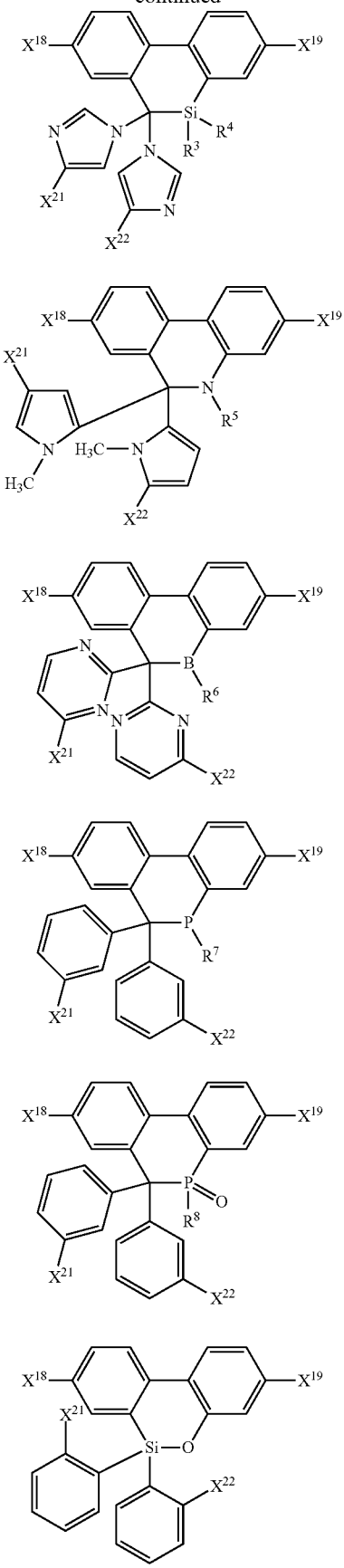

-continued
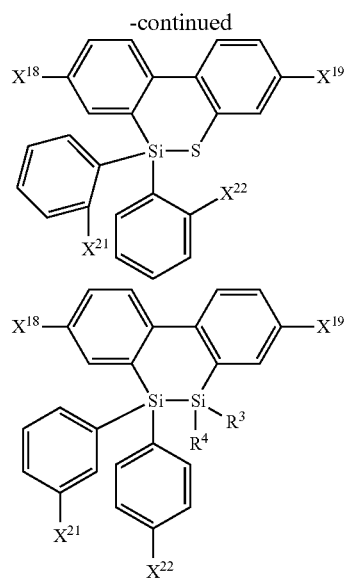
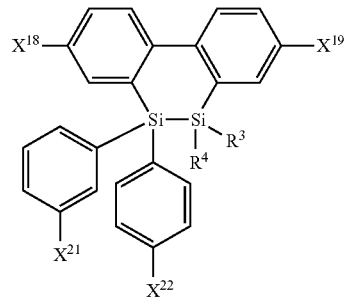
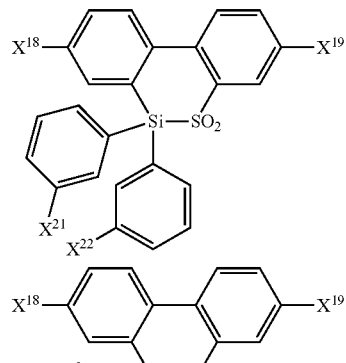
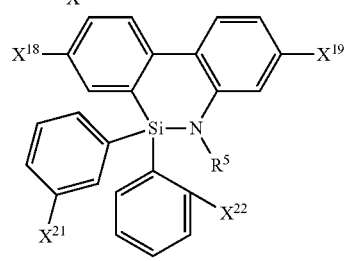
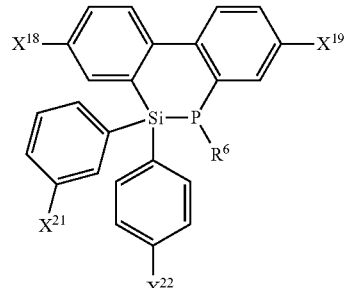
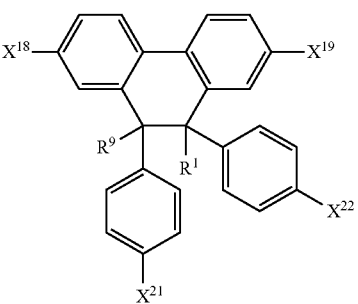
-continued
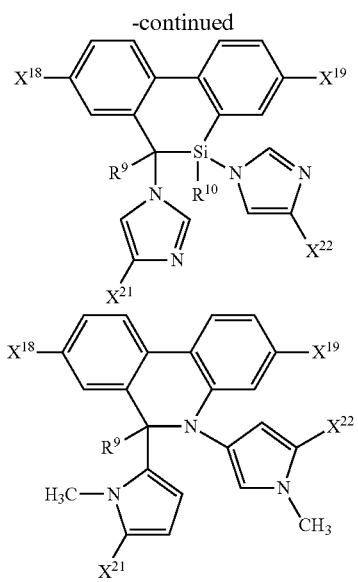
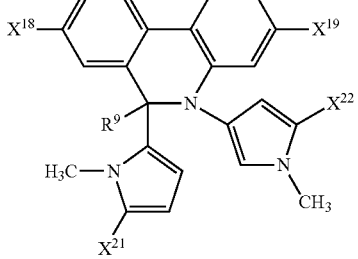
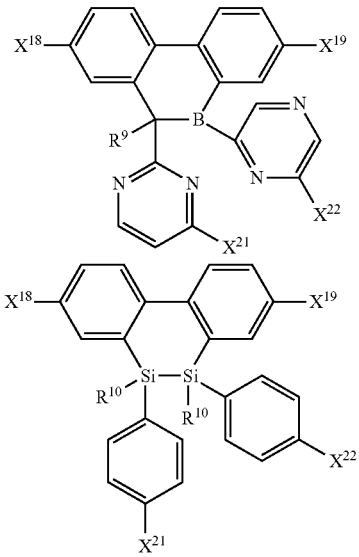
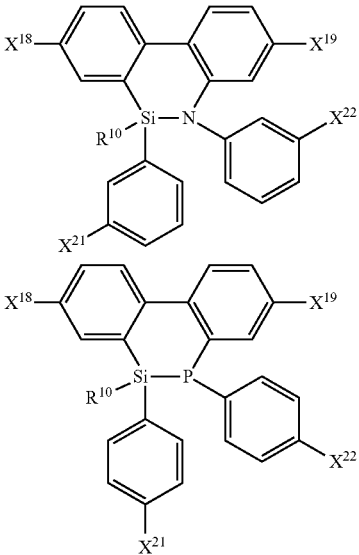

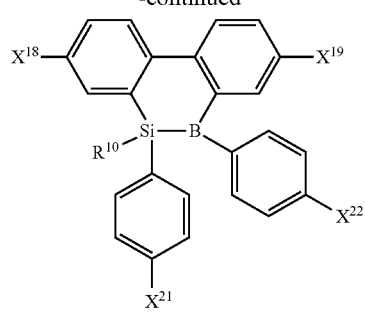
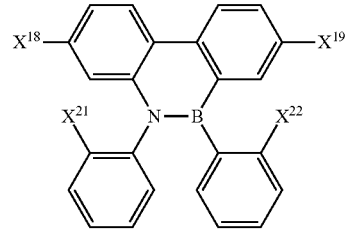
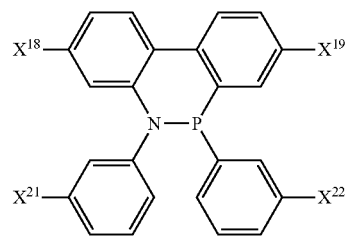
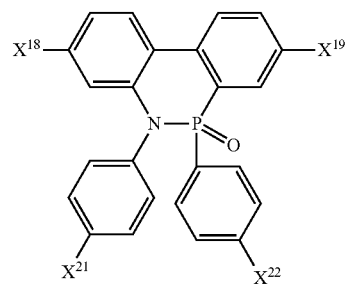
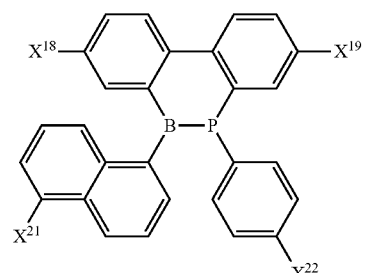
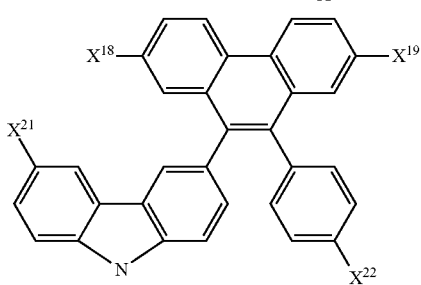

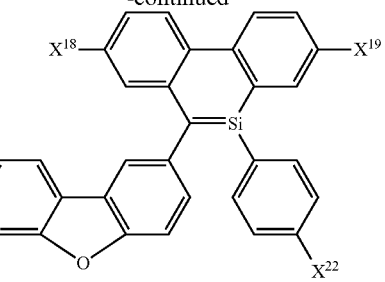

Among them, preferable is the case where $A^4$ and $A^5$ in the above formula (9), (10) or (11), are aromatic hydrocarbons, in view of stability of the compounds.

Especially the case represented by the below formula (9-1), (10-1) or (11-1), it is preferable in view of stability of the compounds.

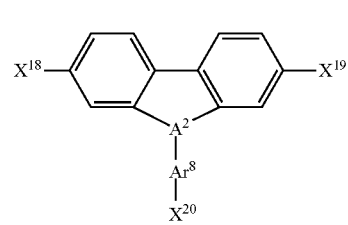

(9-1)

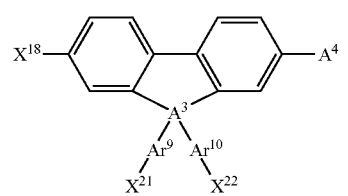

(10-1)

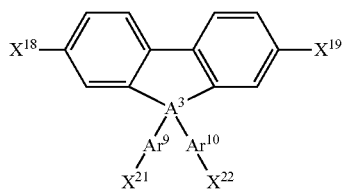

(11-1)

Wherein, $Ar^8, Ar^9, Ar^{10}, A^2, A^3, A^4, X^{18}, X^{19}, X^{20}, A^{21}$ and $X^{22}$ are the same as those of the above. Substituents may be carried on the benzene ring, and the substituents may be connected mutually to form a ring. Examples of the substituent include an alkyl group, alkyloxy group, alkylthio group, aryl group, aryloxy group, arylthio group, arylalkyl group, arylalkyloxy group, arylalkylthio group, acyl group, acyloxy group, amide group, acid imide group, imine residue, amino group, substituted amino group, substituted silyl group, substituted silyloxy group, substituted silylthio group, substituted silylamino group, monovalent heterocyclic group, hetero aryloxy group, hetero arylthio group, arylalkenyl group, arylethynyl group, carboxyl group, alkyloxy carbonyl group, aryloxy carbonyl group, arylalkyloxy carbonyl group, hetero aryloxy carbonyl group, and cyano group.

Next, manufacture method of the compound represented by the above formula (9), (10) or (11) is described.

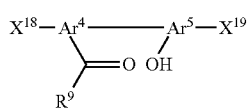
(9-2)

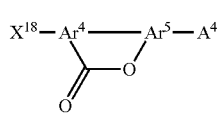
(10-2)

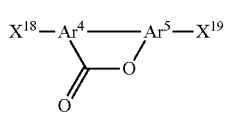
(11-2)

Compounds represented by the above formula (9), (10) or (11), can be produced by reacting, for example, corresponding organolithium reagent or Grignard reagent with the above formula (9-2), (10-1) or (11-2), and then reacting in existence of an acid catalyst. The manufacture method is exemplified below.

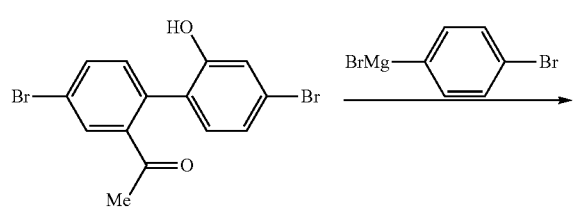

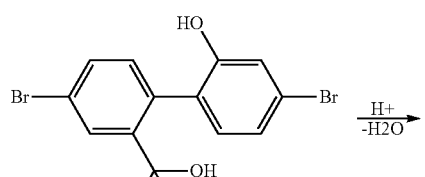

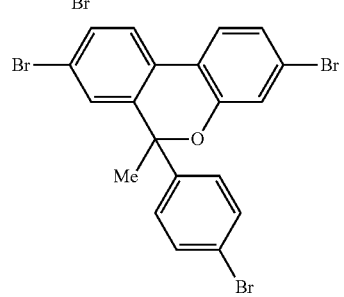

-continued

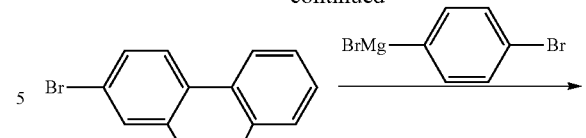

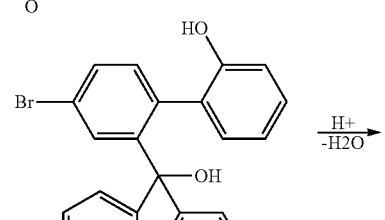

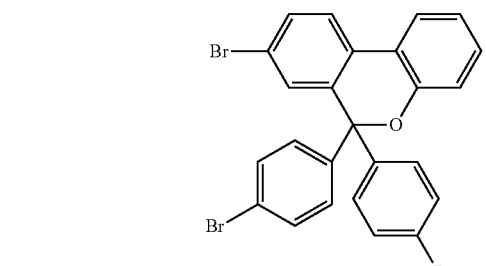

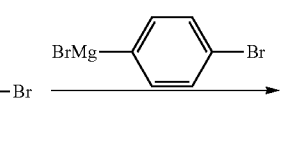

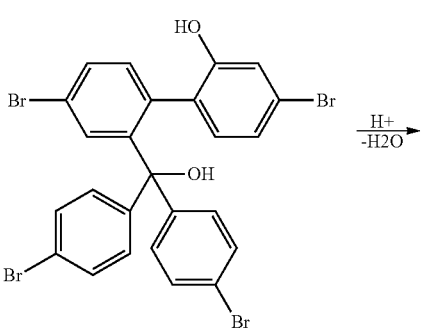

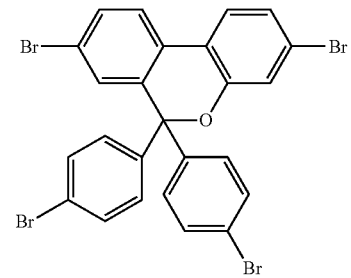

Next, the compounds of formula (15) are described.

  (15)

(wherein, $Ar^4$, $Ar^y$, $A^1$ and $X^3$ represent the same meaning as described above. $A^5$ represents a boron atom, aluminum atom, gallium atom, silicon atom, germanium atom, nitrogen atom, phosphorus atom, arsenic atom, a-valent aromatic hydrocarbon group, a-valent heterocyclic group or a-valent group having a metal complex structure. a represents 3 or 4. A plurality of $Ar^4$s, $Ar^5$s, $A^1$s and $X^{10}$s may be mutually the same or different.

The definitions and specific examples of the a-valent aromatic hydrocarbon group, a-valent heterocyclic group are the same as the definitions and specific examples of the above tri-valent aromatic hydrocarbon group, tetra-valent aromatic hydrocarbon group, tri-valent heterocyclic group and tetra-valent heterocyclic group.

The a-valent group having a metal complex structure is a remaining a-valent group obtained by removing hydrogen atoms of a number of a from an organic ligand of a metal complex having an organic ligand. The number of carbon atoms of the organic ligand is usually about 4 to 60, and for example, 8-quinolynol and derivatives thereof, benzoquinolynol and derivatives thereof, 2-phenyl-pyridine and derivatives thereof, 2-phenyl-benzothiazole and derivatives thereof, 2-phenyl-benzoxazole and derivatives thereof, porphylin and derivatives thereof are mentioned.

Examples of a center metal of the complex include aluminum, zinc, beryllium, iridium, platinum, gold, europium, terbium and the like.

The metal complex having an organic ligand includes metal complexes, triplet light emitting complexes and the like known as fluorescent materials and phosphorescent materials of lower molecular weight. As the a-valent group having a metal complex structure, groups exemplified below are specifically listed. The a-valent group having a metal complex structure may carry a substituent, and the number of carbon atoms of a heterocyclic group does not include the number of carbon atoms of the substituent. The substituent includes alkyl group, alkyloxy group, alkylthio group, aryl group, aryloxy group, arylthio group, arylalkyl group, arylalkyloxy group, arylalkylthio group, acyl group, acyloxy group, amide group, acid imide group, imine residue, amino group, substituted amino group, substituted silyl group, substituted silyloxy group, substituted silylthio group, substituted silylamino group, mono-valent heterocyclic group, heteroaryloxy group, heteroarylthio group, arylalkenyl group, arylethynyl group, carboxyl group, alkyloxycarbonyl group, aryloxycarbonyl group, arylalkyloxycarbonyl group, heteroaryloxycarbonyl group or cyano group.

The definitions and specific examples of these substituents are the same as described above.

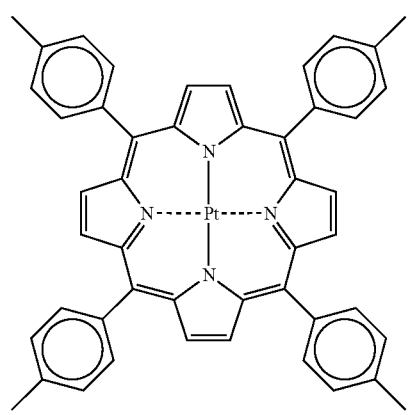

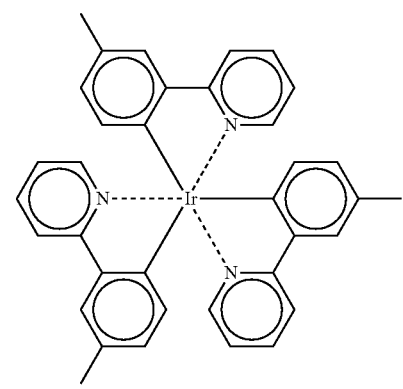

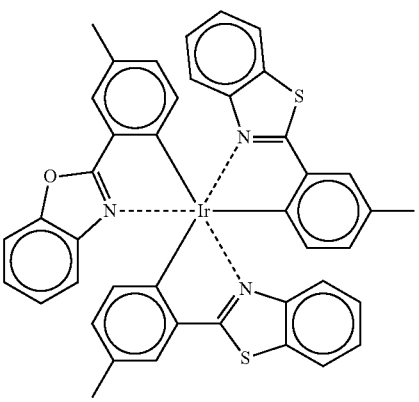

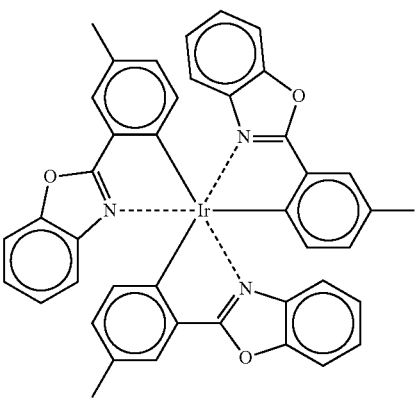

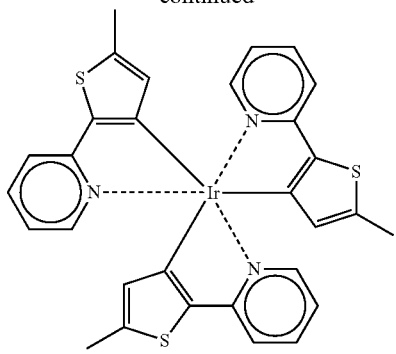
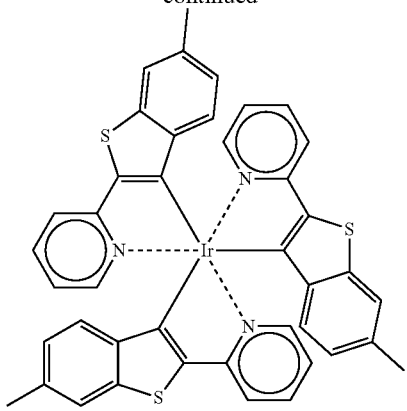
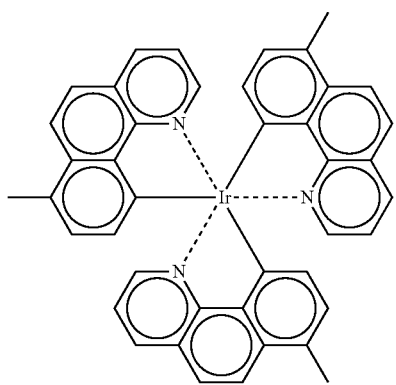
It is preferable that $A^1$ represents O, S, S(=O), SO$_2$, Si(R$^3$)(R$^4$), N(R$^5$), B(R$^6$), P(R$^7$), P(=O)(R$^8$), O—C(=O)—, O—C(R$^1$)(R$^2$)—, N(R$^5$)—C(=O)— or —N=C(R$^9$)— in view of emission strength when the compound is made into a polymer.
As the compound of formula (15), compounds exemplified in the following formulae (35) and (36) are mentioned.
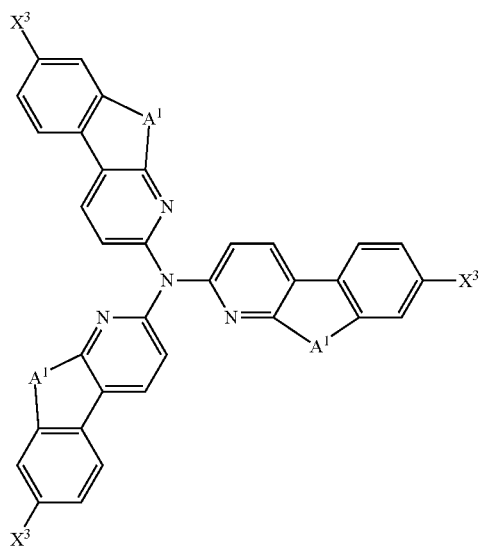
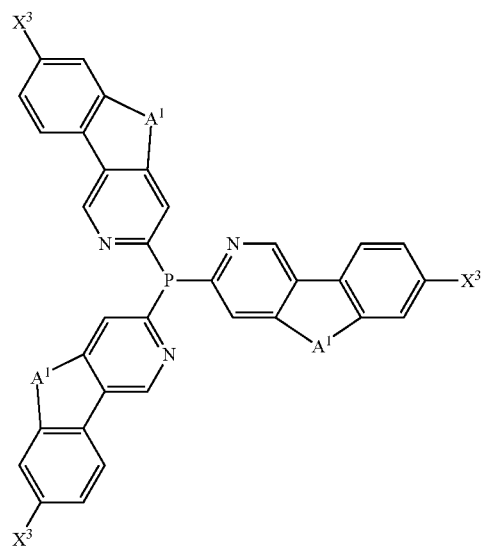

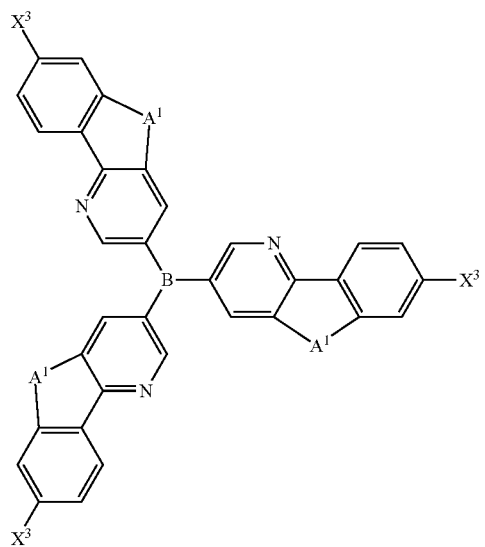
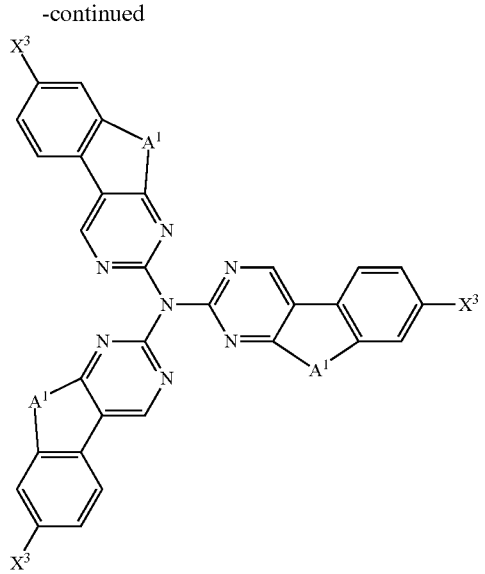
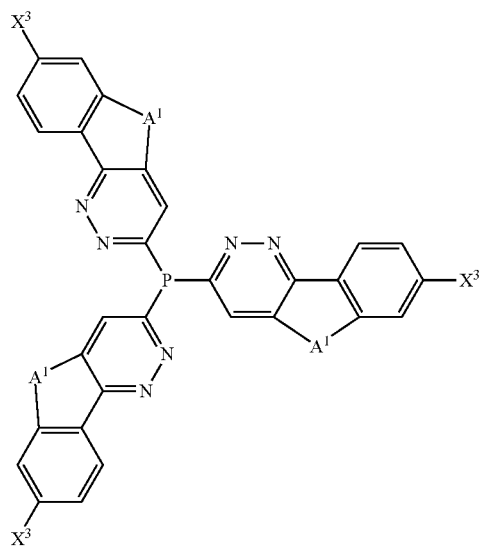
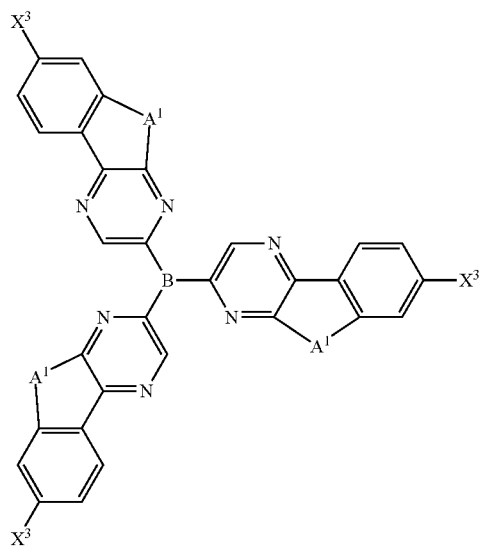
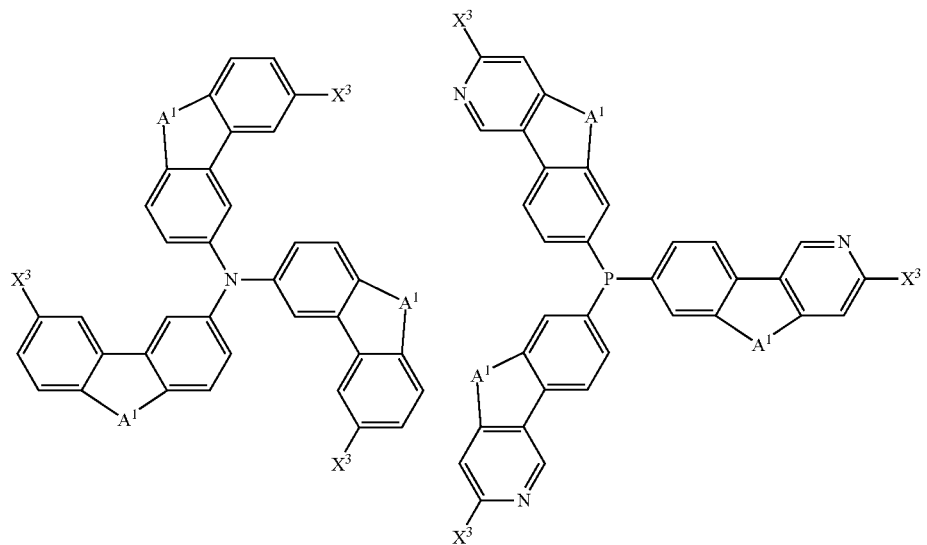

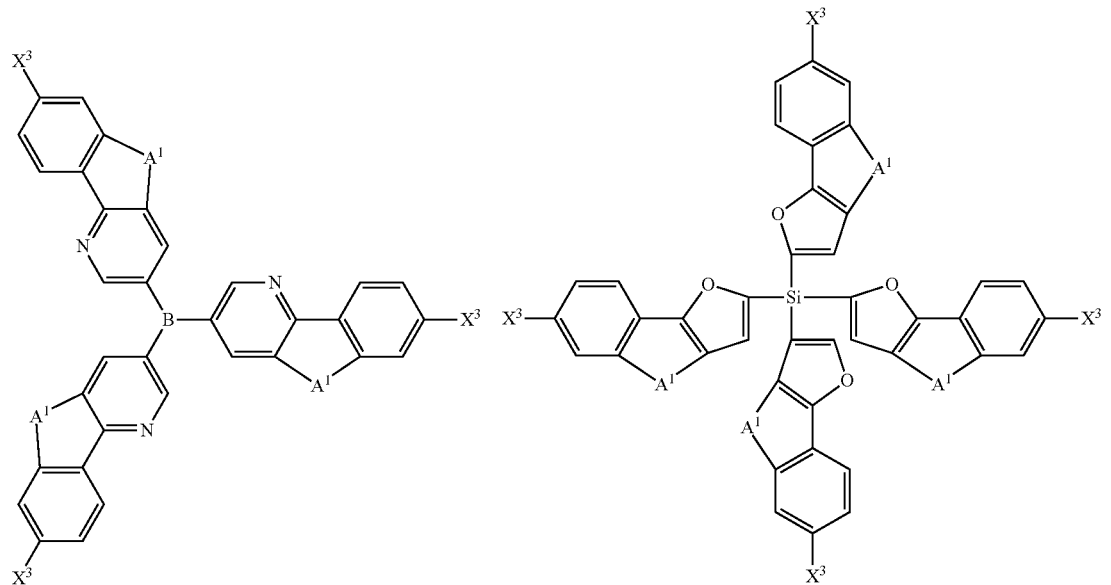
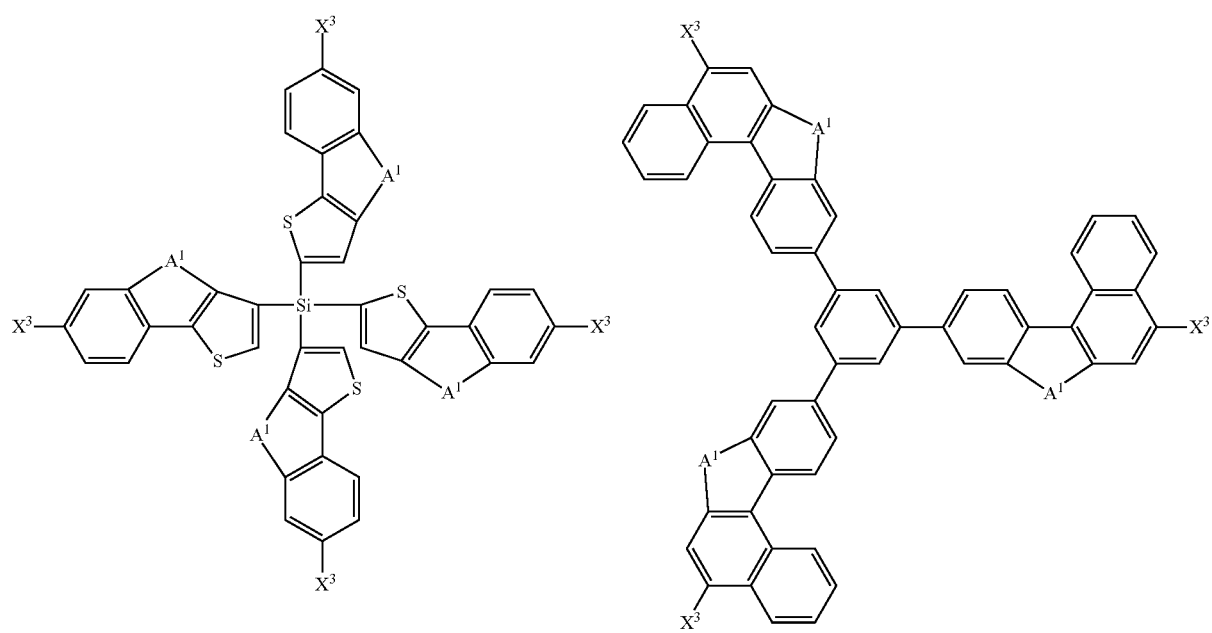

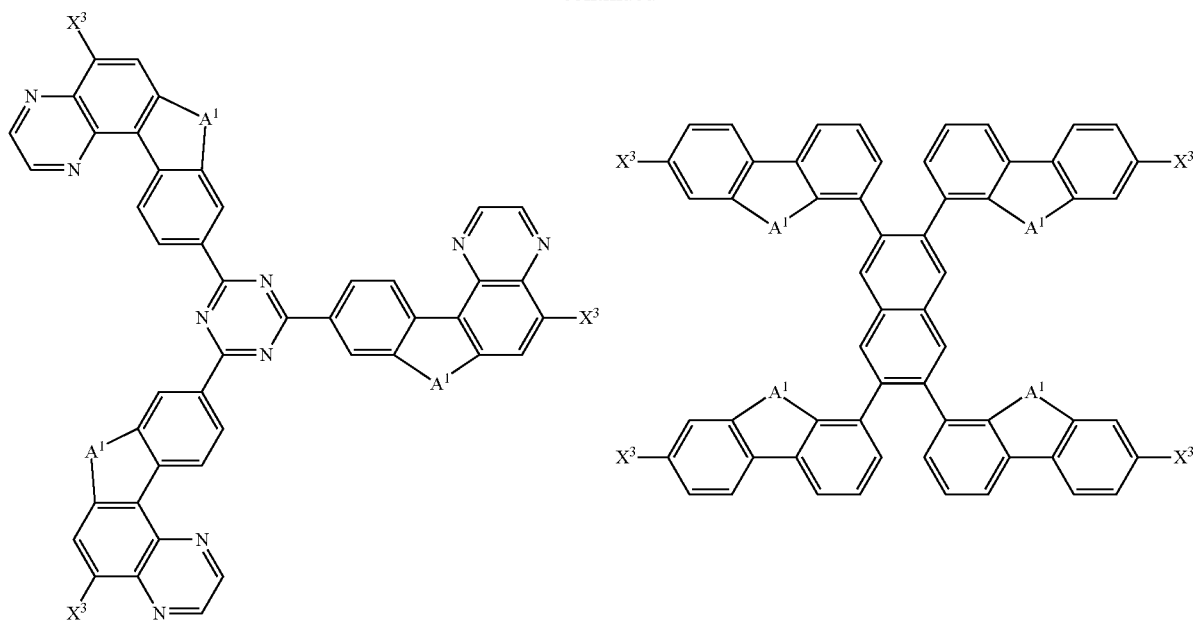
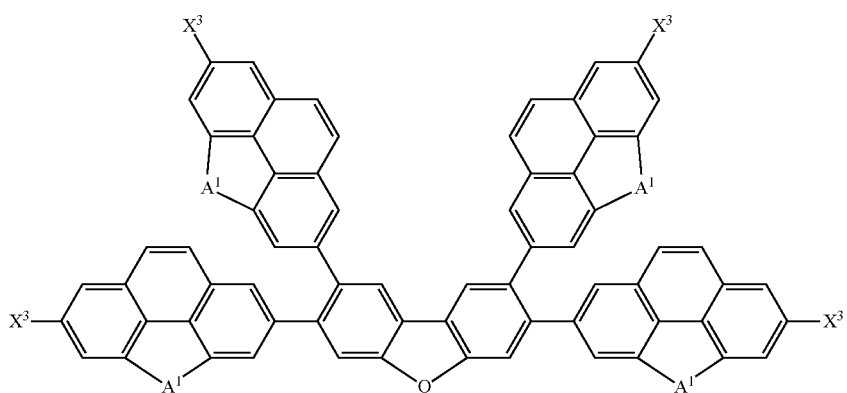
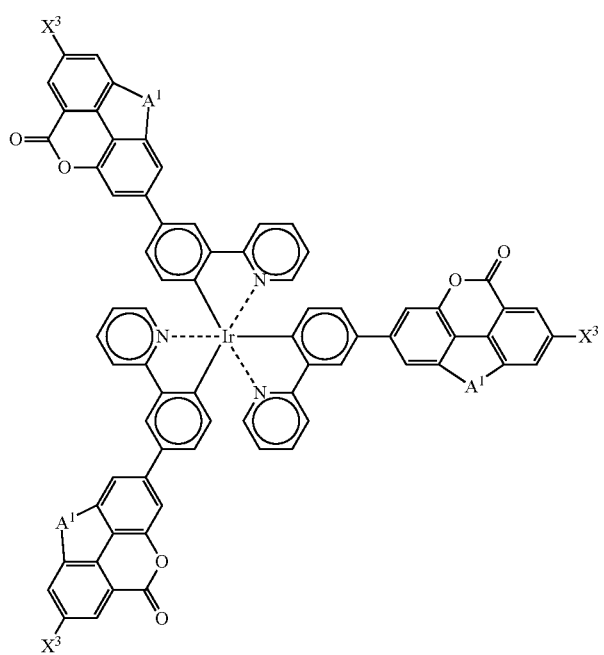

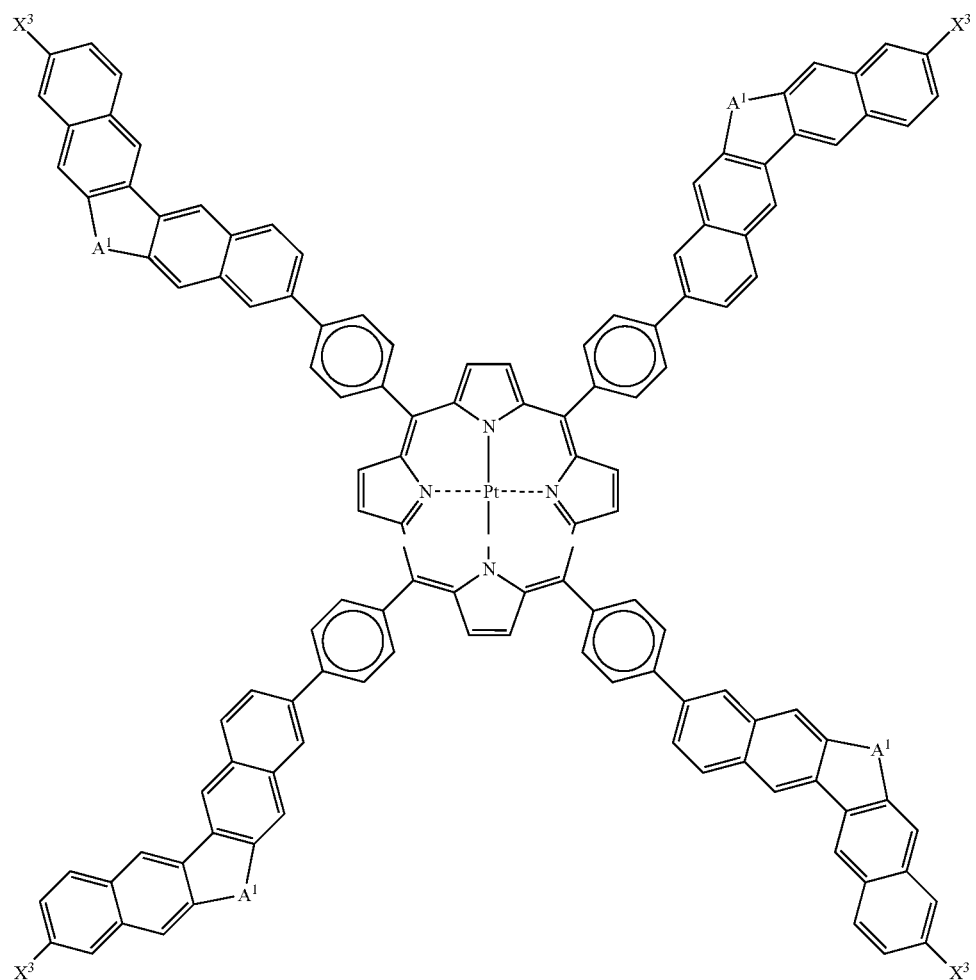
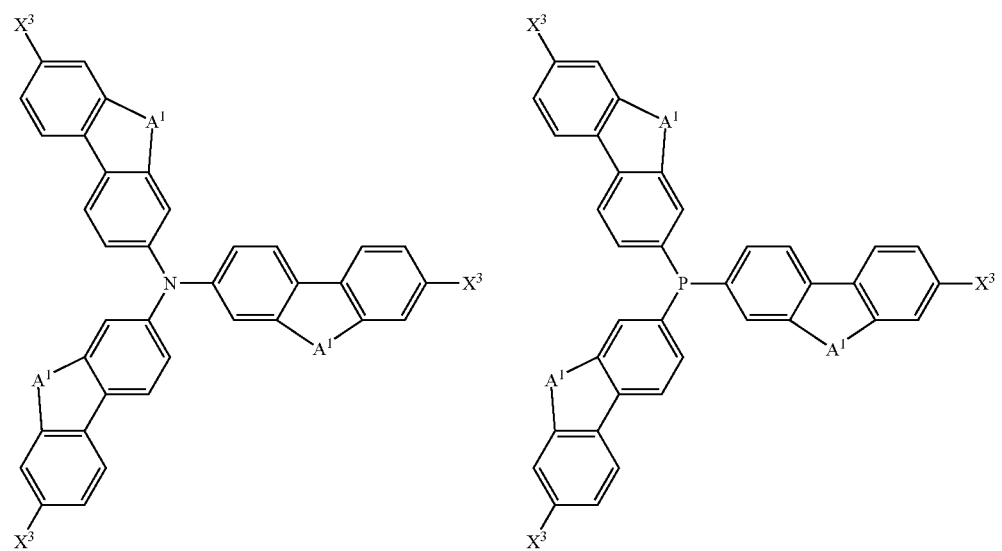

-continued
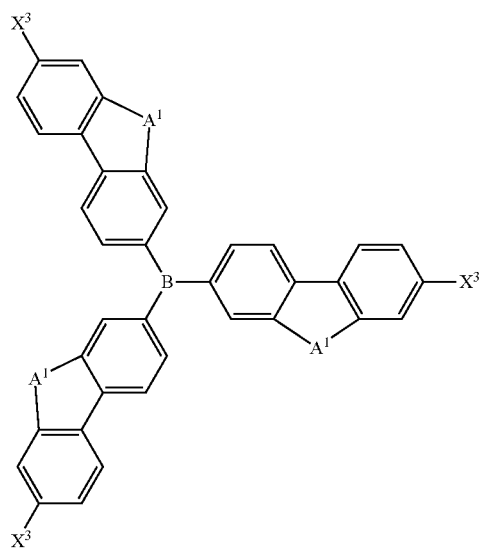
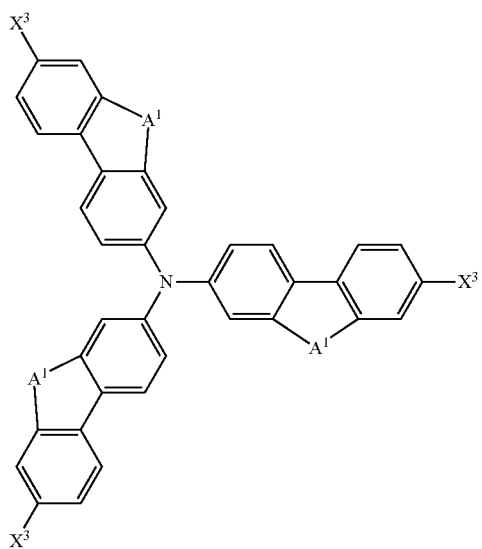
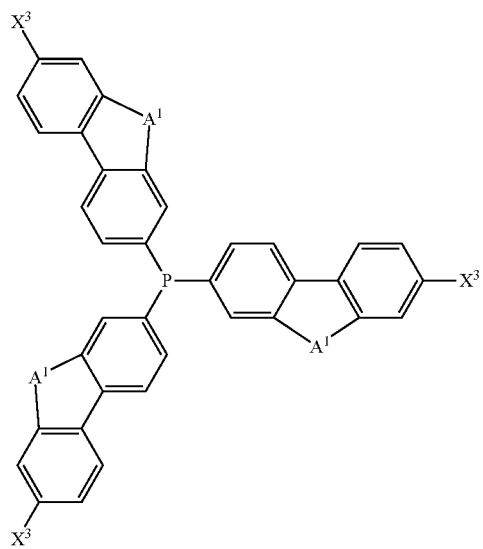
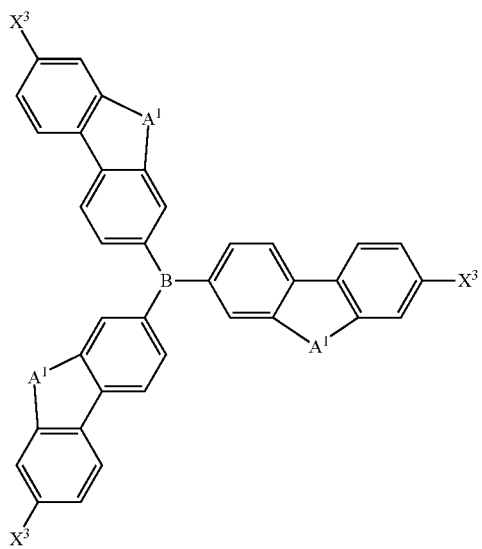
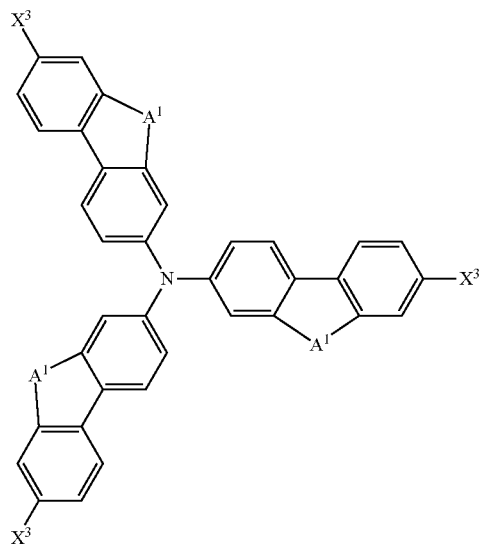
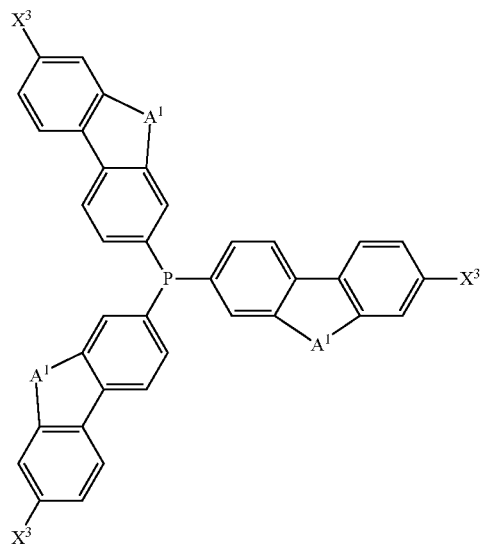

-continued
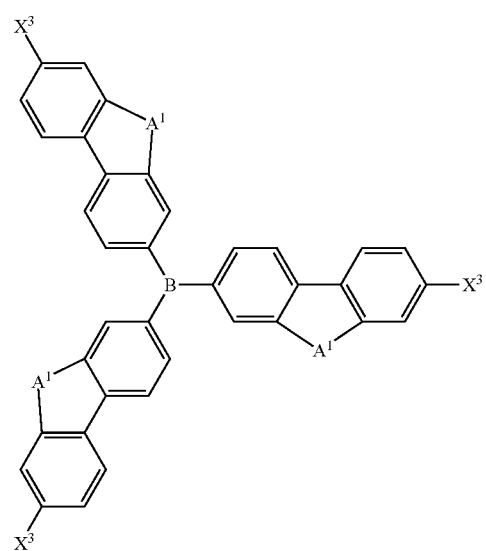
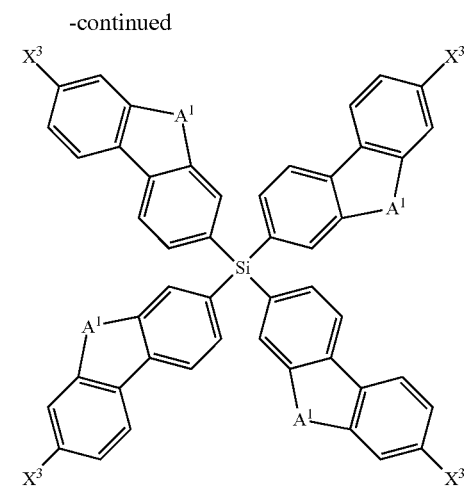
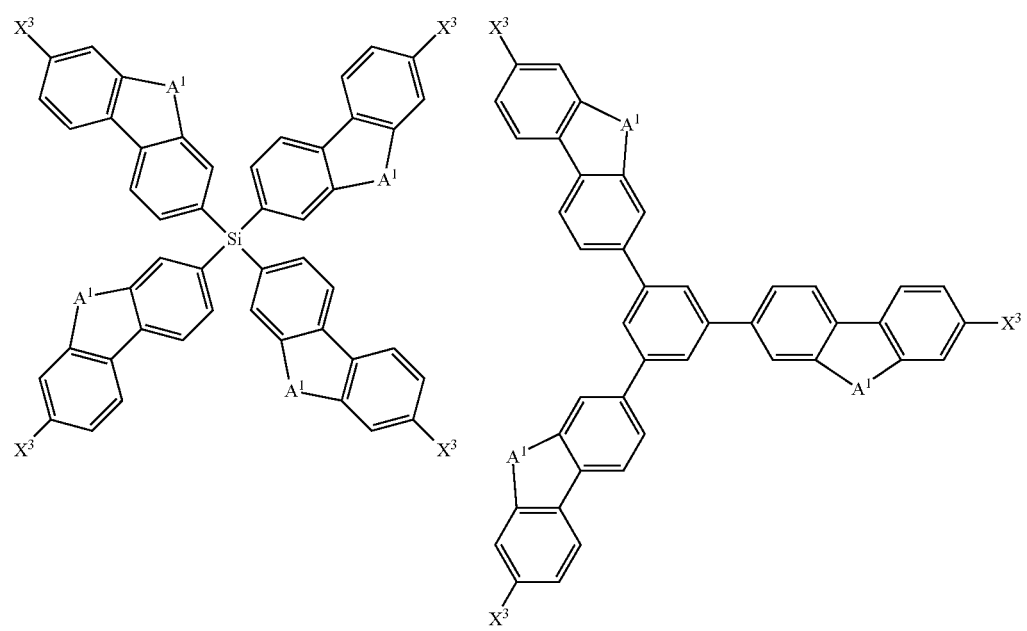

-continued
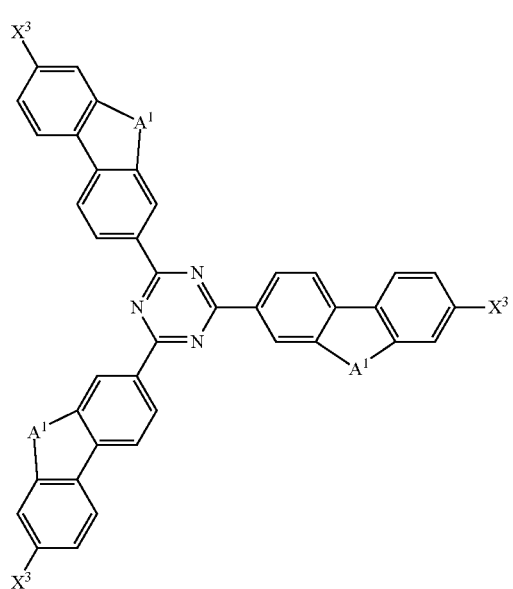
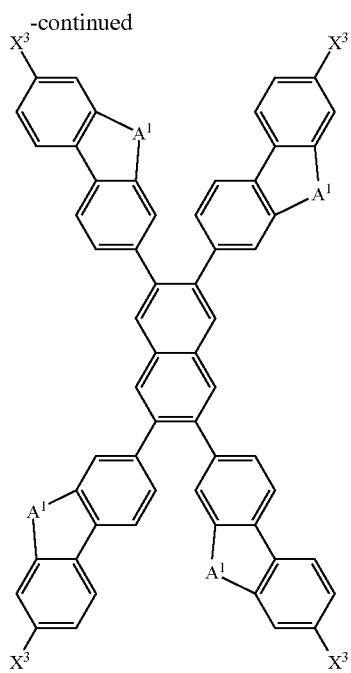
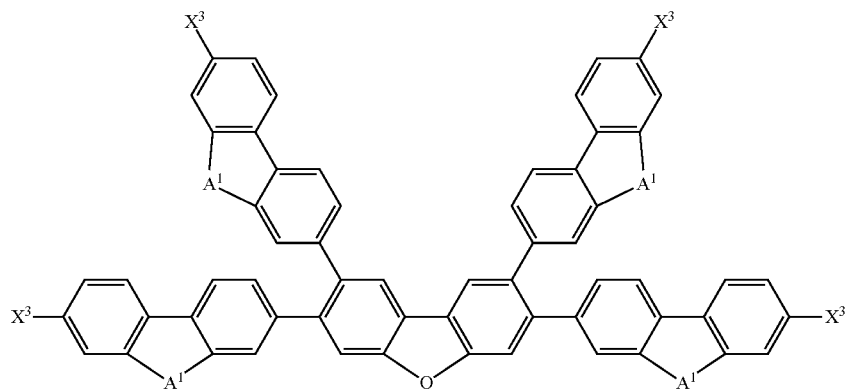
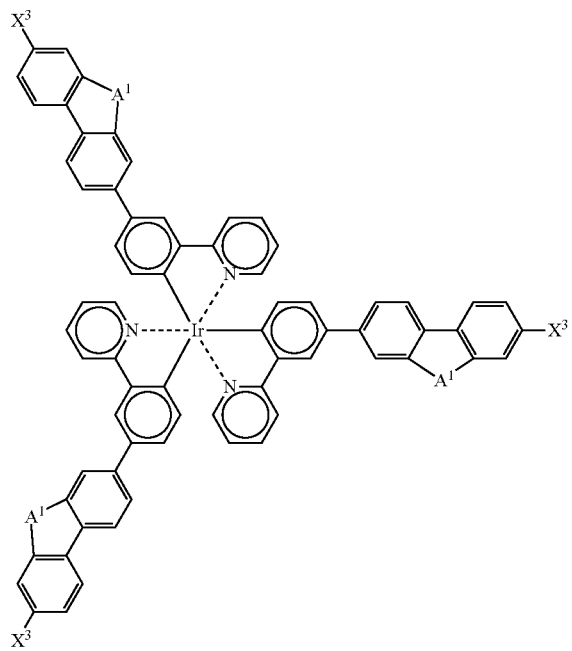

-continued

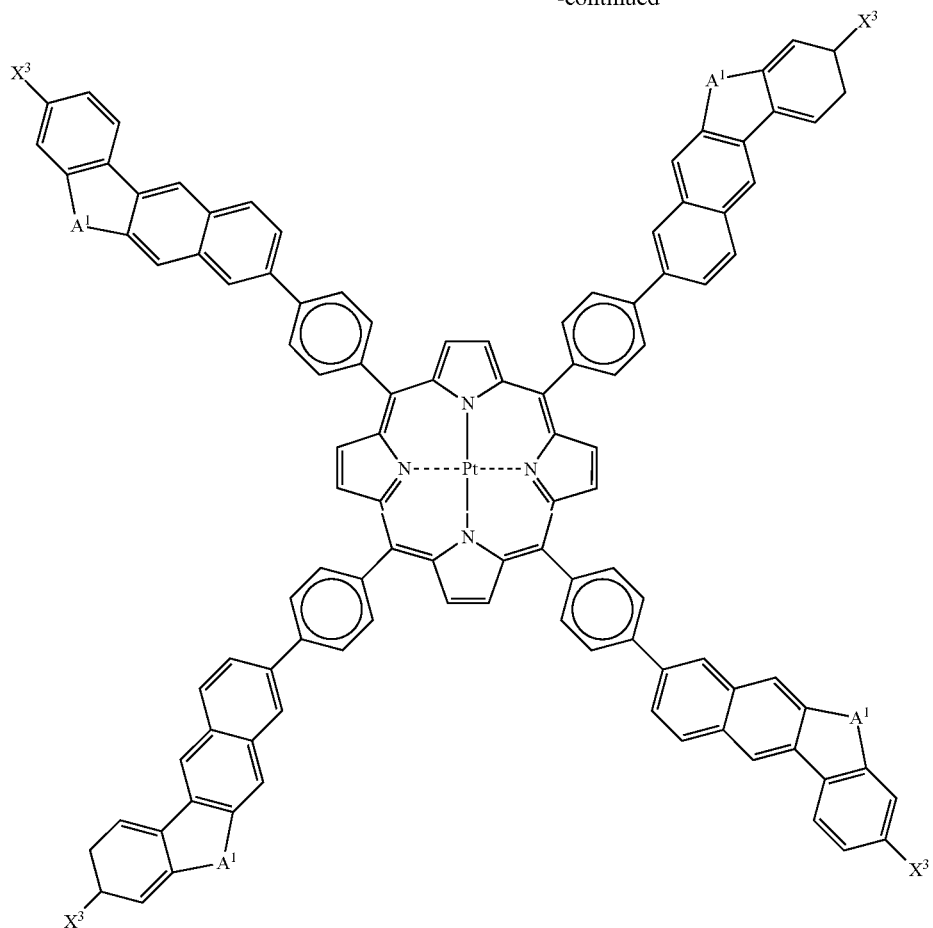

Particularly, it is preferable that $Ar^4$ and $Ar^5$ in formula (15) represent an aromatic hydrocarbon group in view of stability of the compound.

Especially, compounds of the following formula (15-1) are preferable in view of stability of the compound.

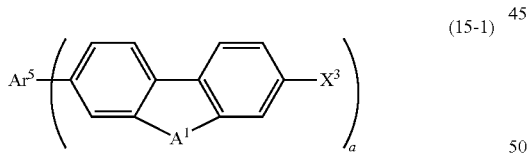

(15-1)

wherein, $A^1$, $A^5$, $X^3$ and a represent the same meaning as described above. Benzene rings may carry a substituent, and substituents may be mutually connected to form a ring. The substituent includes alkyl group, alkyloxy group, alkylthio group, aryl group, aryloxy group, arylthio group, arylalkyl group, arylalkyloxy group, arylalkylthio group, acyl group, acyloxy group, amide group, acid imide group, imine residue, amino group, substituted amino group, substituted silyl group, substituted silyloxy group, substituted silylthio group, substituted silylamino group, mono-valent heterocyclic group, heteroaryloxy group, heteroarylthio group, arylalkenyl group, arylethynyl group, carboxyl group or cyano group.

A method of producing a compound of formula (15) is described below. When $A^5$ represents a boron atom, aluminum atom, gallium atom, silicon atom, germanium atom, phosphorus atom or arsenic atom, the compound can be produced by a method of reacting the following formulae (15-2) and (15-3), and the like. In the formulae, $A^1$, $A^5$, $Ar^4$, $Ar^5$ and $X^3$ are the same as described above. M represents a lithium atom, sodium atom, potassium atom or magnesium atom. $X^{33}$ represents a halogen atom.

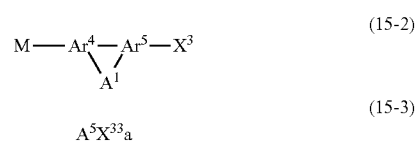

(15-2)

(15-3)

The production method is exemplified below.

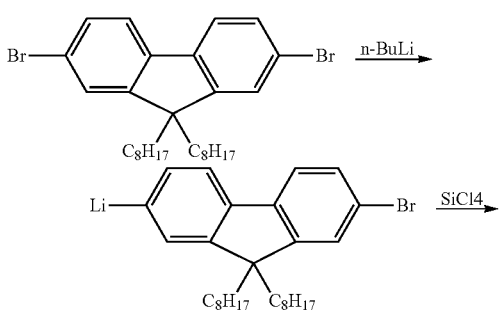

-continued

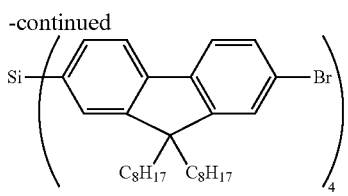

When $A^5$ is an a-valent aromatic hydrocarbon group, a-valent heterocyclic group or a-valent group having a metal complex structure, the compound can be produced by a method of cross-coupling a compound of formula (15-4) and a compound of formula (15-5), and the like. In the formulae, $A^1, A^5, Ar^4, Ar^5$ and $X^3$ are the same as described above. $X^{34}$ and $X^{35}$ each independently represent a halogen atom, alkylsulfonate group, arylsulfonate group, arylalkylsulfonate group, trialkyltin group, boric ester group or —$B(OH)_2$. As the cross coupling method, Suzuki coupling, Grignard coupling, Stille coupling and the like are exemplified.

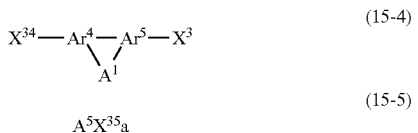

The production method is exemplified below.

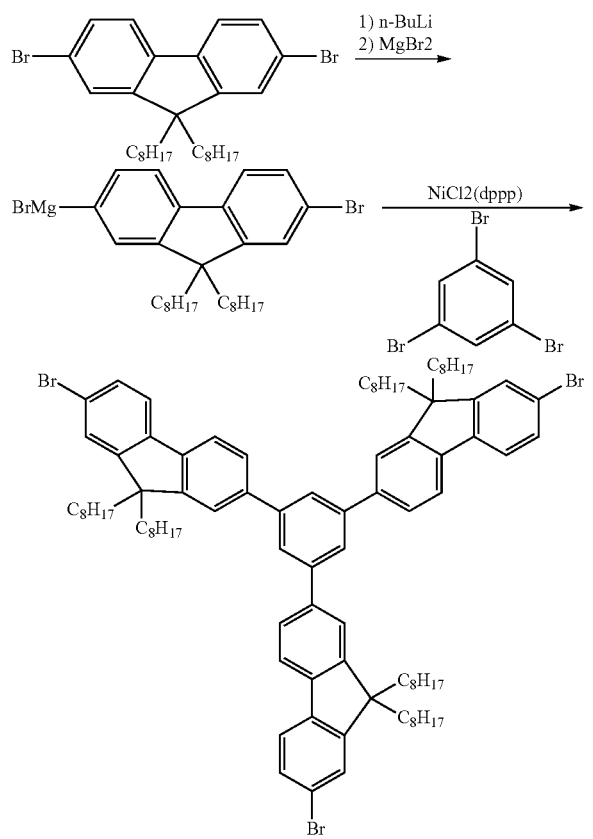

As the condensation reaction method, when connected via a vinylene group, the compound can be produced, for example, by a method described in Japanese Patent Application Laid-Open (JP-A) No. 5-202355. When two or more condensation-reactive functional groups are carried, a condensation polymerization reaction can also be used.

Namely, exemplified are [1] Wittig reaction of a compound having an aldehyde group and a compound having a phosphonium base, [2] Heck reaction of a compound having a vinyl group and a compound having a halogen atom, [3] Horner-Wadsworth-Emmons reaction of a compound having an aldehyde group and a compound having an alkylphosphonate group, [4] Knoevenagel reaction of a compound having a formyl group and a compound having a cyano group, [5] McMurry reaction of a compound having two or more formyl groups, and the like.

The above reactions [1] to [5] shown by the following formulae.

Branched oligomers and branched polymers can be produced by subjecting a compound of the present invention to a condensation polymerization reaction.

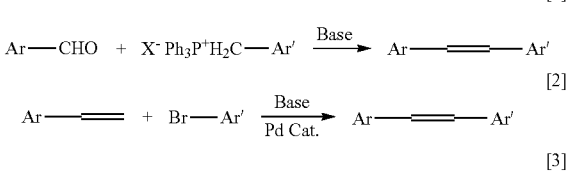

As the method of condensation reaction for forming a direct bond, for example, [6] Suzuki coupling reaction, [7] Grignard coupling reaction, [8] condensation reaction using Ni(0) catalyst, and the like, are exemplified.

The above polymerization methods [6] to [8] are shown by the following formulae.

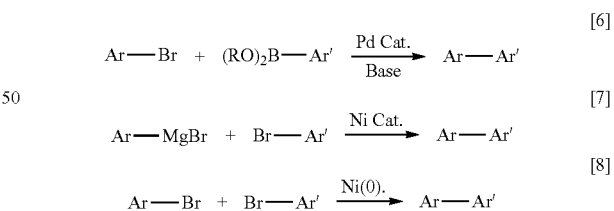

As the reaction method, a compound of the present invention can be dissolved if necessary in an organic solvent and reacted at temperatures not lower than the melting point and not higher than the boiling point of the organic solvent using, for example, an alkali or suitable catalyst. Known methods described, for example, in "Organic Reactions", vol. 14, p. 270-490, John Wiley & Sons, Inc., 1965, "Organic Reactions", vol. 27, p. 345-390, John Wiley & Sons, Inc., 1982, "Organic Syntheses", Collective Volume VI, p. 407-411, John Wiley & Sons, Inc., 1988, Chem. Rev., vol. 95, p. 2457

(1995), J. Organomet. Chem., vol. 576, p. 147 (1999), J. Prakt. Chem. Vol. 336, p. 247 (1994), Makromol. Chem. Macromol. Symp., vol. 12, p. 229 (1987), and the like, can be used.

The organic solvent varies depending on compounds and reactions used, and in general, for suppressing a side reaction, it is preferable that the solvent to be used is subjected sufficiently to a deoxygenation treatment and a reaction is progressed in an inert atmosphere. Likewise, a dehydration treatment is preferably conducted. (Here, a reaction in a two-phase system with water such as Suzuki coupling reaction is not included).

For the reaction, an alkali or suitable catalyst is appropriately added. This may be advantageously selected depending on the reaction to be used. It is preferable that the alkali or catalyst is dissolved sufficiently in the solvent used in the reaction. As a method of mixing an alkali or catalyst, a method of slowly adding a solution of an alkali or catalyst while stirring the reaction liquid under an atmosphere of an inert gas such as argon, nitrogen and the like, or a method of slowing adding the reaction liquid to a solution of an alkali or catalyst, reversely, is exemplified. Further, purification can be performed by usual methods such as re-precipitation purification, fractionation by chromatography and the like after synthesis.

The reaction conditions are described more specifically. In the cases of Wittig reaction, Horner reaction, Knoevengel reaction and the like, an alkali is used in an amount of not smaller than 1 equivalent, preferably 1 to 3 equivalents based on a functional group of a monomer. The alkali is not particularly restricted, and for example, potassium-t-butoxide, sodium-t-butoxide, metal alcoholates such as sodium ethylate, lithium methylate and the like, hydride reagents such as sodium hydride and the like, amides such as sodiumamide and the like can be used. As the solvent, N,N-dimethylformamide, tetrahydrofuran, dioxane, toluene and the like are used. The reaction can be progressed usually at temperatures of from room temperature to about 150° C. The reaction time is, for example, 5 minutes to 40 hours, and times for sufficient progress of the reaction are advantageous, and since there is no need to leave for long time after completion of the reaction, the reaction time is preferably 10 minutes to 24 hours. Since concentration in the reaction is too thin, reaction efficiency is poor and when to dense, the reaction cannot be controlled easily, the concentration may be appropriately selected in a range from about 0.01 wt % to the maximum concentration for dissolution, and usually from 0.1 wt % to 20 wt %. In the case of Heck reaction, monomers are reacted in the presence of a base such as triethylamine and the like using a palladium catalyst. A solvent having relatively high boiling point is used such as N,N-dimethylformamide, N-methylpyrrolidone and the like, the reaction temperature is about 80 to 160° C., and the reaction time is approximately from 1 hour to 100 hours.

In the case of Suzuki coupling reaction, an inorganic base such as potassium carbonate, sodium carbonate, barium hydroxide and the like, an organic base such as triethylamine and the like, and an inorganic salt such as cesium fluoride and the like are added and reacted in an amount of not smaller than 1 equivalent, preferably to 10 equivalents based on monomers using, for example, palladium[tetrakis(triphenylphosphine)], palladium acetates and the like as a catalyst. The inorganic salt may be reacted in the form of aqueous solution in a two-phase system. As the solvent, N,N-dimethylformamide, toluene, dimethoxyethane, tetrahydrofuran and the like are exemplified. Temperatures of approximately from 50 to 160° C. are suitably used depending on the solvent. The reaction temperature may be raised to near the boiling point of the solvent to cause reflux. The reaction time is about 1 to 200 hours.

In the case of Grignard reaction, a method is exemplified in which a halide and metal Mg are reacted in an ether-based solvent such as tetrahydrofuran, diethyl ether, dimethoxyethane and the like to give a Grignard reagent solution, this solution is mixed with a monomer solution prepared separately, a nickel or palladium catalyst is added while paying attention an excess reaction, then, the temperature is raised and the reaction is performed while refluxing. The Grignard reagent is used in an amount of not smaller than 1 equivalent, preferably 1 to 1.5 equivalents, more preferably 1 to 1.2 equivalents based on monomers. Also in the case of polymerization by methods other than these methods, the reaction can be performed according to a known method.

Examples are shown below for illustrating the present invention more in detail but the present invention is not limited to them.

Synthesis Example 1

Synthesis of Compound A

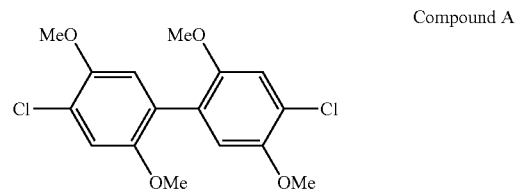 [SMILES: COc1cc(-c2cc(OC)c(Cl)cc2OC)c(OC)cc1Cl]

Compound A

A raw material 2,2',5,5'-tetramethoxy-1,1'-biphenyl was synthesized from 1-bromo-2,5-dimethoxybenzene by a coupling reaction using zero-valent nickel.

Into a three-necked flask under an inert atmosphere was charged 2,2',5,5'-tetramethoxy-1,1'-biphenyl (7.0 g, 26 mmol) which was then dissolved in dehydrated N,N-dimethylformamide (100 ml). While cooling the flask in an ice bath, a solution of N-chlorosuccinimide (6.8 g, 52 mmol) in dehydrated N,N-dimethylformamide (70 ml) was dropped from a dropping funnel over a period of 15 minutes. After completion of dropping, the temperature was returned to room temperature while slowly stirring the mixture, and the mixture was stirred for 1 day.

To the reaction liquid was added water (300 ml), and the deposited precipitate was recovered by filtration. The resultant precipitate was re-crystallized from toluene/hexane to obtain an intended substance (yield: 5.8 g).

$^1$H-NMR (300 MHz/CDCl$_3$):
δ3.74 (s, 6H), 3.87 (s, 6H), 6.85 (s, 2H), 7.02 (s, 2H)

Synthesis Example 2

Synthesis of Compound B

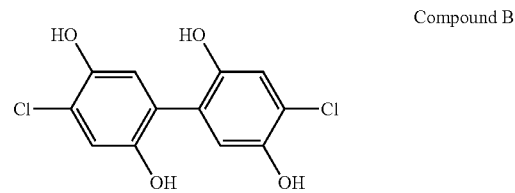 [SMILES: Oc1cc(-c2cc(O)c(Cl)cc2O)c(O)cc1Cl]

Compound B

Into a three-necked flask under an inert atmosphere was charged compound A (5.8 g, 17 mmol) which was then dissolved in dehydrated methylene chloride (100 ml). While cooling the flask in an ice bath, a solution of boron tribromide in methylene chloride (1 mol/L, 50 ml) was dropped from a dropping funnel over a period of 30 minutes. After completion of dropping, the temperature was returned to room temperature while slowly stirring the mixture, and the mixture was stirred over night.

The reaction liquid was extracted with ethyl acetate, an organic layer was washed with water, then, the solvent was distilled off to obtain an intended substance (yield: 4.9 g).

$^1$H-NMR (300 MHz/CDCl$_3$):
δ6.64 (s, 2H), 6.82 (s, 2H), 8.9 to 9.1 (br, 2H), 9.37 (s, 2H)

Example 1

Synthesis of Compound C

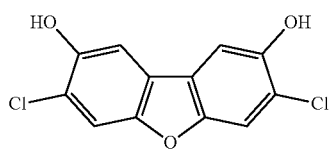

Compound C

Into a three-necked flask under an inert atmosphere was added compound B (4.8 g, 17 mmol), zeolite (6.7 g, Zeolite HSZ 360HUA (Tosoh)) and o-dichlorobenzene (170 ml) dried over molecular sieves. The mixture was stirred for 13 hours while heating in an oil bath (bath temperature: 180° C.). The reaction liquid was cooled to near room temperature, and hexane (200 ml) was added. The deposited precipitate was filtrated, and washed and dried over hexane. The precipitate was extracted with ethyl acetate, and the solution was subjected bottom cut in a short column of silica gel, then, the solvent was distilled off to obtain an intended substance (yield: 3.5 g).

MS spectrum: [M−H]$^−$ 267.0

Example 2

Synthesis of Compound D

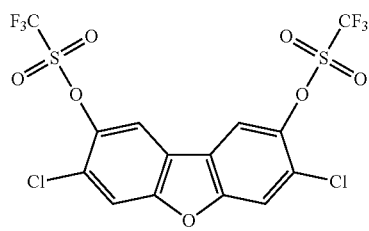

Compound D

Into a three-necked flask under an inert atmosphere was charged compound C (4.2 g) and 4-N,N-dimethylaminopyridine (5.7 g) which were then dissolved in dehydrated methylene chloride (40 ml). While cooling the flask in an ice bath, trifluoromethanesulfonic anhydride (11 g) was dropped over a period of 30 minutes. The temperature as slowly raised up to room temperature without any other treatment and the mixture was stirred for 5 hours. Toluene was added and the mixture was filtrated, and the filtrate was subjected to bottom cut in a short column of silica gel, then, the solvent was distilled off. The resultant solid was re-crystallized from a toluene/hexane system to obtain an intended substance (7.6 g).

$^1$H-NMR (300 MHz/CDCl$_3$):
δ7.80 (s, 2H), 7.93 (s, 2H)

Synthesis Example 3

Synthesis of Compound E

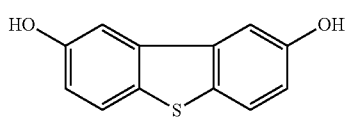

Compound E

Into a 1-L four-necked flask under an inert atmosphere was added 7 g of 2,8-dibromodibenzothiophene and 280 ml of THF, and the mixture was stirred and dissolved at room temperature, then, cooled down to −78° C. 29 ml (1.6 mol hexane solution) of n-butyllithium was dropped. After completion of dropping, the mixture was stirred for hours while maintaining the temperature, and 13 g of trimethoxyboronic acid was dropped. After completion of dropping, the temperature was slowly returned to room temperature. The mixture was stirred for 3 hours at room temperature, then, disappearance of raw materials was confirmed by TLC. 100 ml of 5% sulfuric acid was added to terminate the reaction, and the mixture was stirred at room temperature for 12 hours. Water was added for washing, and an organic layer was extracted. The solvent was substituted by ethyl acetate, then, 5 ml of 30% hydrogen peroxide water was added and the mixture was stirred at 40° C. for 5 hours. Thereafter, an organic layer was extracted, and washed with a 10% ammonium sulfate iron (II) aqueous solution, then, dried to remove the solvent, obtaining 4.43 g of brown solid.

MS (APCI(−)): (M−H)$^−$ 215

Synthesis Example 4

Synthesis of Compound F

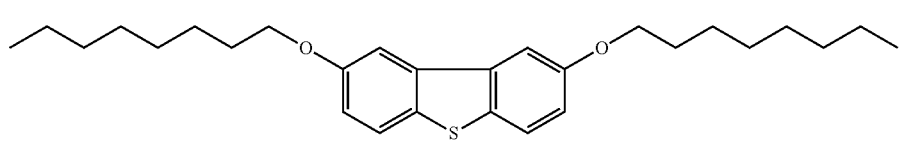

Compound F

Into a 200 ml three-necked flask under an inert atmosphere was charged 4.43 g of compound E, 25.1 g of n-octyl bromide and 12.5 g (23.5 mmol) of potassium carbonate, and 50 ml of methyl isobutyl ketone was added as a solvent to this, and the mixture was heated under reflux at 125° C. for 6 hours. After completion of the reaction, the solvent was removed, and separation was effected between chloroform and water, an organic layer was extracted, further, washed with water twice. The product was dried over anhydrous sodium sulfate, then, purified by a silica gel column (developing solvent: toluene/cyclohexane=1/10), to obtain 8.49 g of compound F.

$^1$H-NMR (300 MHz/CDCl$_3$):

δ0.91 (t, 6H), 1.31 to 1.90 (m, 24H), 4.08 (t, 4H), 7.07 (dd, 2H), 7.55 (d, 2H), 7.68 (d, 2H)

Synthesis Example 5

Synthesis of Compound G

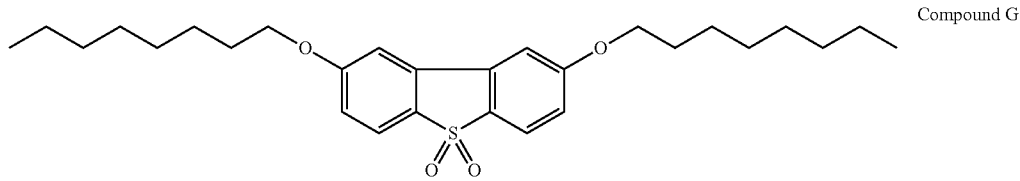 [SMILES: CCCCCCCCOc1ccc2c(c1)-c1cc(OCCCCCCCC)ccc1S2(=O)=O]

Compound G

Into a 100 ml three-necked flask was charged 6.67 g of compound F and 40 ml of acetic acid, and the temperature was raised up to a bath temperature of 140° C. in an oil bath. Subsequently, 13 ml of 30% hydrogen peroxide water was added through a cooling tube, and the mixture was vigorously stirred for 1 hour, then, the mixture was poured into 180 ml of cold water to terminate the reaction. The reaction mixture was extracted with chloroform, and dried, then, the solvent was removed to obtain 6.96 g of compound G.

$^1$H-NMR (300 MHz/CDCl$_3$):

δ0.90 (t, 6H), 1.26 to 1.87 (m, 24H), 4.06 (t, 4H), 7.19 (dd, 2H), 7.68 (d, 2H), 7.84 (d, 2H)

MS (APCI (+)): (M+H)$^+$ 473

Example 3

Synthesis of Compound H

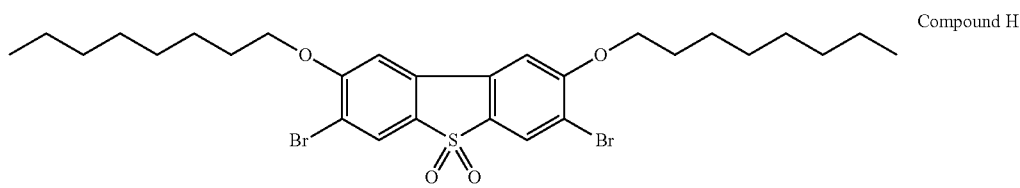 [SMILES: CCCCCCCCOc1cc2c(cc1Br)S(=O)(=O)c1cc(Br)c(OCCCCCCCC)cc1-2]

Compound H

Into a 200 ml four-necked flask under an inert atmosphere was charged 3.96 g of compound G and 15 ml of an acetic acid/chloroform=1:1 mixed solution, and the mixture was stirred to be dissolved. Subsequently, 6.02 g of bromine was dissolved in 3 ml of the above solvent and added to this and the mixture was stirred for 3 hours. An aqueous sodium thiosulfate solution was added to remove unreacted bromine, separation was effected between chloroform and water, an organic layer was extracted and dried. The solvent was removed and purified by a silica gel column (developing solvent: chloroform/hexane=1/4), to obtain 4.46 g of compound H.

$^1$H-NMR (300 MHz/CDCl$_3$):

δ0.95 (t, 6H), 1.30 to 1.99 (m, 24H), 4.19 (t, 4H), 7.04 (s, 2H), 7.89 (s, 2H)

MS (FD$^+$)M$^+$ 630

Example 4

Synthesis of Compound I

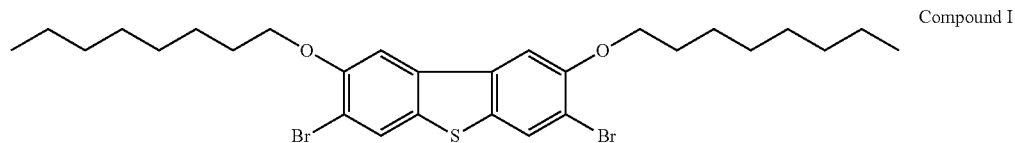 [SMILES: CCCCCCCCOc1cc2c(cc1Br)sc1cc(Br)c(OCCCCCCCC)cc12]
Compound I

Into a 200 ml three-necked flask under an inert atmosphere was charged 3.96 g of compound H and 50 ml of diethyl ether, and the mixture was heated up to 40° C. and stirred. 1.17 g of lithium aluminum hydride was added portion-wise and reacted for 5 hours. By adding water portion-wise, excess lithium aluminum hydride was decomposed, and the reaction solution was washed with 5.7 ml of 36% hydrochloric acid. Separation was effected between chloroform and water, an organic layer was extracted, then, dried. The product was purified by a silica gel column (developing solvent: chloroform/hexane=1/5), to obtain 1.8 g of compound I.

$^1$H-NMR (300 MHz/CDCl$_3$):

δ0.90 (t, 6H), 1.26 to 1.97 (m, 24H), 4.15 (t, 4H), 7.45 (s, 2H), 7.94 (s, 2H)

MS (FD$^+$)M$^+$598

Example 5

Synthesis of Compound J

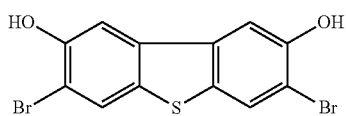
Compound J

Compound I was dissolved in dichloromethane, and boron tribromide was added and the mixture was stirred. After completion of the reaction, water was added, an aqueous phase was extracted with ethyl acetate, and the solvent was distilled off to obtain compound J.

Example 6

Synthesis of Compound K

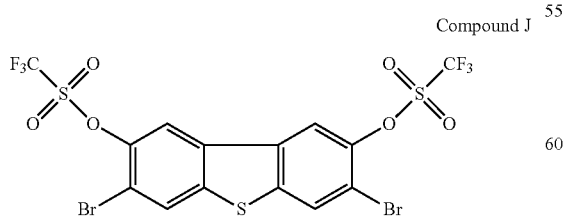
Compound J

Compound I was dissolved in dichloromethane, and boron tribromide was added and the mixture was stirred. After completion of the reaction, water was added, an aqueous phase was extracted with ethyl acetate, and the solvent was distilled off to obtain compound J.

Synthesis Example 6

Synthesis of Compound K

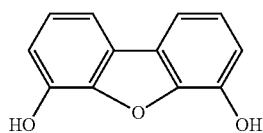
Compound K

A 500 ml three-necked flask was purged with argon, then, 3.00 g of dibenzofuran was placed and dissolved in 60 ml of dehydrated diethyl ether, and 8.2 ml of N,N,N',N'-tetramethylethylenediamine was added to this. The mixture was cooled to −78° C., then, 54 ml of s-butyllithium (0.99 M cyclohexane-hexane solution) was dropped over a period of 10 minutes. The mixture was heated up to room temperature, and stirred for 4 hours, then, cooled to −78° C., and 7.1 ml of trimethoxyborane was added in one time. The mixture was heated up to room temperature, and stirred for 4 hours. The mixture was cooled down to 0° C., and 20 ml of 30% hydrogen peroxide water was dropped over a period of 30 minutes. After dropping, the mixture was stirred for 1 hour, and 20 ml of a saturated sodium hydrogen sulfite aqueous solution was dropped over 20 minutes. The mixture was stirred at room temperature for 3 hours, then, 1N hydrochloric acid was added to render the solution acidic, and the mixture was extracted with 100 ml of diethyl ether three times. The mixture was dried over sodium sulfate, then, 3.76 g of compound K was obtained.

$^1$H-NMR (CD3OD, 300 MHz):

δ7.46 (2H, d), 7.18 (2H, t), 6.97 (2H, d)

MS (ESI-negative, KCl addition) m/z: 199.1 ([M−H]$^-$)

Synthesis Example 7

Synthesis of Compound L

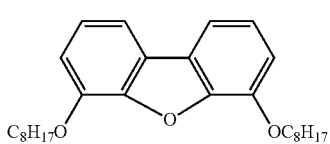
Compound L

A 100 ml three-necked flask was purged with nitrogen, then, 0.50 g of compound K was placed and dissolved in 18 ml of dehydrated DMF, and 0.80 g of potassium carbonate and 0.9 ml of 1-bromooctane were added to this. The mixture was stirred for 2 hours at a bath temperature of 120° C., then, the mixture was allowed to cool, and 50 ml of water was added and the mixture was extracted with 50 ml of toluene three times. Organic phases were combined and filtrated through silica gel, then, the solvent was distilled off to obtain 0.90 g of compound L.

$^1$H-NMR (CDCl$_3$, 300 MHz): δ7.05 (2H, d), 7.22 (2H, t), 6.97 (2H, d), 4.24 (4H, t), 1.96 to 1.87 (4H, m), 1.58 to 1.48 (4H, m), 1.43 to 1.30 (16H, m), 0.89 (6H, t)

$^{13}$C-NMR (CDCl$_3$, 300 MHz): 6146.0, 145.6, 126.4, 123.6, 113.0, 111.3, 69.7, 32.1, 29.7, 29.6, 29.5, 26.3, 23.0, 14.4

MS (APCI-positive) m/z: 425.3 ([M+H]$^+$)

Example 7

Synthesis of Compound M

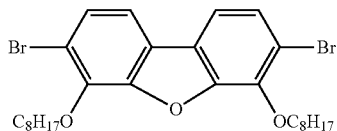

Compound M

A 100 ml three-necked flask was purged with nitrogen, then, 0.83 g of compound L was placed and dissolved in 17 ml of dehydrated diethyl ether, and 0.8 ml of N,N,N',N'-tetramethylethylenediamine was added to this, and the mixture was cooled to −78° C. 5.1 ml of s-butyllithium (0.99 M cyclohexane-hexane solution) was dropped over a period of 5 minutes. After dropping, the mixture was stirred for 10 minutes, then, the cooling bath was removed, and the mixture was stirred at room temperature for 4 hours, then, cooled to −78° C. Onto this solution was dropped a solution prepared by dissolving 0.7 ml of 1,2-dibromo-1,1,2,2-tetrafluoroethane in 5 ml of diethyl ether over a period of 5 minutes. The mixture was stirred for 5 minutes, then, the cooling bath was removed, and the mixture was stirred at room temperature for 3 hours. 10 ml of a saturated sodium hydrogen carbonate aqueous solution was added and an aqueous phase was extracted with 10 ml of toluene twice. Organic phases were combined and filtrated through silica gel, then, the solvent was distilled off to obtain 1.10 g of compound M.

$^1$H-NMR (CDCl$_3$, 300 MHz): δ7.47 (2H, d), 7.39 (2H, d), 4.47 (4H, t), 1.92 to 1.83 (4H, m), 1.61 to 1.51 (4H, m), 1.40 to 1.25 (16H, m), 0.89 (6H, t)

$^{13}$C-NMR (CDCl$_3$, 300 MHz): 6147.7, 142.3, 128.3, 125.9, 115.3, 114.1, 74.1, 32.1, 30.5, 29.7, 29.6, 26.3, 23.0, 14.4

MS (ESI-positive) m/z: 619.0, 621.0, 622.5 ([M+H]$^+$)

Example 8

Synthesis of Compound N

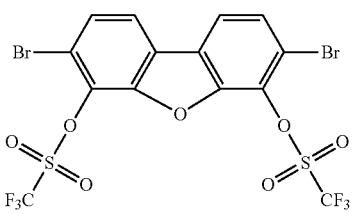

Compound N

Compound N can be synthesized by the same treatment as in Examples 5 and 6.

Synthesis Example 8

Synthesis of Compound O

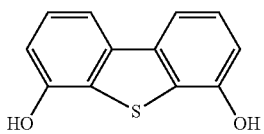

Compound O

A 500 ml three-necked flask was purged with argon, then, 5.00 g of dibenzothiophene was placed and dissolved in 100 ml of dehydrated diethyl ether, and 12.5 ml of N,N,N',N'-tetramethylethylenediamine was added to this. The mixture was cooled down to −78° C., then, 82 ml of s-butyllithium was dropped over a period of 10 minutes. The mixture was heated up to room temperature, and stirred for 3 hours, then, cooled down to −78° C., and 11 ml of trimethoxyborane was added in one time. The mixture was heated up to room temperature, and stirred for 1.5 hours. The mixture was cooled to 0° C., and 30 ml of 30% hydrogen peroxide water was dropped over a period of 20 minutes. After dropping, the mixture was stirred for 1 hour, and 30 ml of a saturated sodium hydrogen sulfite aqueous solution was dropped over a period of 10 minutes. The mixture was stirred at room temperature for 3 hours, then, 1N hydrochloric acid was added to render the mixture acidic, and the mixture was extracted with 100 ml of diethyl ether three times. The mixture was dried over sodium sulfate, then, 6.31 g of a crude product was obtained. The product was re-crystallized from a toluene/ethanol=5:1 mixed solvent twice to obtain 0.61 g of compound O.

$^1$H-NMR (CD3OD, 300 MHz): δ7.69 (2H, d), 7.31 (2H, t), 6.90 (2H, d)

MS (ESI-negative, KCl addition) m/z: 215.1 ([M−H]$^−$)

Synthesis Example 9

Synthesis of Compound P

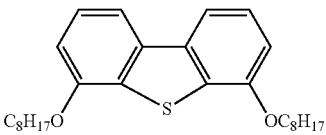

Compound P

A 100 ml three-necked flask was purged with nitrogen, then, 0.50 g of compound O was placed and dissolved in 14 ml of dehydrated DMF, and 0.86 g of potassium carbonate and 0.9 ml of 1-bromooctane were added. The mixture was stirred for 2 hours at a bath temperature of 120° C., then, allowed to cool, and 50 ml of water was added and the mixture was extracted with 50 ml of toluene three times. Organic phases were combined and filtrated through silica gel, then, the solvent was distilled off to obtain 0.95 g of compound P.

$^1$H-NMR (CDCl$_3$, 300 MHz): δ7.69 (2H, d), 7.35 (2H, t), 6.86 (2H, d), 4.14 (4H, t), 1.92 to 1.82 (4H, m), 1.54 to 1.47 (4H, m), 1.42 to 1.30 (16H, m), 0.89 (6H, t)

$^{13}$C-NMR (CDCl$_3$, 300 MHz): 6154.6, 138.0, 129.2, 125.8, 114.5, 107.9, 68.9, 32.2, 29.7, 29.6, 26.4, 23.0, 14.5

Example 9

Synthesis of Compound Q

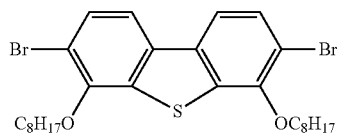
Compound Q

A 500 ml three-necked flask was purged with argon, then, 9.00 g of compound P was placed and dissolved in 180 ml of dehydrated diethyl ether, and 8.7 ml of N,N,N',N'-tetramethylethylenediamine was added. The mixture was cooled down to −78° C., then, 57 ml of s-butyllithium (0.99 M cyclohexane-hexane solution) was dropped over a period of 10 minutes. The mixture was heated up to room temperature gradually, then, refluxed for 5 hours, then, cooled down to −78° C., and a solution prepared by dissolving 8 ml of 1,2-bromo-1,1,2,2-tetrafluoroethane in 40 ml of dehydrated diethyl ether was dropped over a period of 30 minutes. The mixture was heated up to room temperature, and stirred for 3 hours. 100 ml of a saturated sodium hydrogen carbonate aqueous solution was added to this and the mixture was extracted with 100 ml of hexane twice. The mixture was passed through a silica gel short column, then, the solvent was distilled off to obtain 11.20 g of compound Q.

$^1$H-NMR (CDCl$_3$, 300 MHz): δ7.62 (2H, d), 7.56 (2H, d), 4.20 (4H, t), 1.96 to 1.84 (4H, m), 1.64 to 1.48 (4H, m), 1.40 to 1.25 (16H, m), 0.90 (6H, t)

MS (APPI-positive) m/z: 600, 598, 596 ([M]$^+$)

Example 10

Synthesis of Compound S

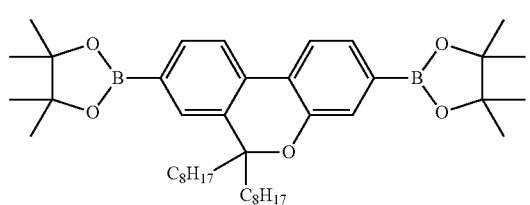
R

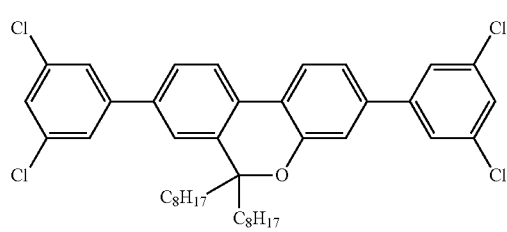
S

A 50 ml two-necked flask was purged with nitrogen, then, 100 mg (0.15 mmol) of compound R (disclosed in JP-A No. 2004-168999), 120 mg (0.44 mmol) of 1,3-dichloro-5-iodobenzene and 10 mg (0.01 mmol) of tetrakis(triphenylphosphine)palladium (0) were placed which were then dissolved in 1 ml of toluene. 1 ml of a 1M potassium carbonate aqueous solution was added, and the mixture was stirred for 20 hours under reflux. Liquid separation was effected, and an organic was washed with water and saturated saline, then, the solvent was distilled off to obtain a crude product.

MS (ESI-negative) m/z: 729 ([M+Cl]$^-$)

Example 11

Synthesis of Compound V

Compound T (disclosed in JP-A No. 2004-168999) was treated with boron tribromide in a dichloromethane solvent, to obtain compound U. Compound U can be subjected to the same treatment as in Example 2, to obtain compound V.

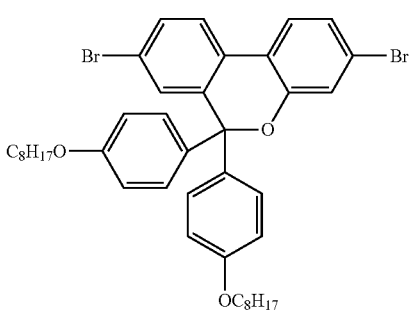
T

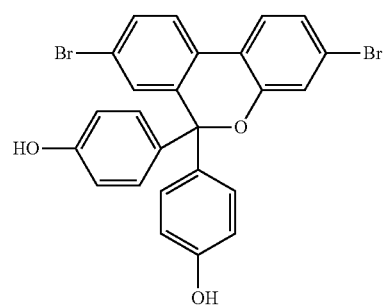
U

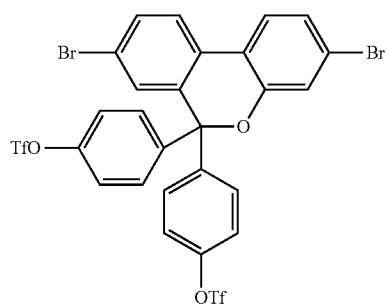
V

Example 12

Synthesis of Compound W

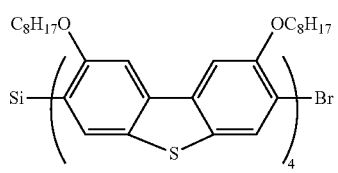

Compound I synthesized above was treated with 1 equivalent of n-butyllithium at −78° C. in a THF solvent, then, reacted with 1/4 equivalent of silicon tetrachloride, to obtain compound W.

INDUSTRIAL APPLICABILITY

The aromatic compound of the present invention is a novel aromatic compound having 3 or 4 condensation-reactive functional groups or precursors thereof, and useful as a monomer for producing a branched polymer compound, and the like.

Condensation reaction compounds, oligomers, dendrimers and polymer compounds synthesized using aromatic compounds of the present invention can be used as medical and agricultural chemicals, organic electron materials and intermediates thereof.

Oligomers, dendrimers and polymer compounds synthesized using aromatic compounds of the present invention shows fluorescence or phosphorescence in solid condition, and can be used as a light emitting polymer (light emitting material of higher molecular weight). The polymer compound has an excellent electron transporting ability, and can be suitably used as a polymer LED material or electric charge transporting material. The polymer LED using this light emitting polymer is a polymer LED of high performance capable of being driven at low voltage with high efficiency. Thus, this polymer LED can be preferably used in apparatuses such as back lights of liquid crystal displays, light sources having a curved surface or flat surface for illumination, displays of segment type, flat panel displays of dot matrices, and the like.

Oligomers, dendrimers and polymer compounds synthesized using aromatic compounds of the present invention can also be used as coloring matters for laser, materials for organic solar batteries, organic semiconductors for organic transistors, and materials for conductive thin film such as light emitting thin film, conductive thin film, organic semiconductor thin film and the like.

The invention claimed is:

1. An aromatic compound of the following formula (6-1):

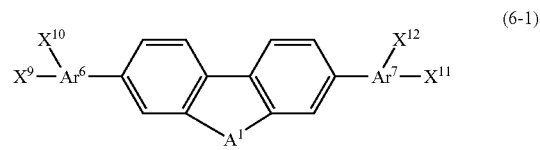

wherein $X^9$, $X^{10}$, $X^{11}$ and $X^{12}$ each independently represent a halogen atom, an alkylsulfonate group, an arylsulfonate group, an arylalkylsulfonate group, a boric ester group, —B(OH)$_2$, a monohalogenated-methyl group, a sulfonium-methyl group, a phosphonium-methyl group, a phosphonate-methyl group, a cyano methyl group, a formyl group or a vinyl group;

Ar$^6$ and Ar$^7$ each independently represent a trivalent aromatic hydrocarbon group or a trivalent heterocyclic group, wherein Ar$^6$ and Ar$^7$ may have a substituent;

A$^1$ represents —Z$^1$—, wherein Z$^1$ represents O, S, C(=O), S(=O), SO$_2$, C(R$^1$)(R$^2$), Si(R$^3$)(R$^4$), N(R$^5$), B(R$^6$), P(R$^7$) or P(=O)(R$^8$), wherein R$^1$, R$^2$, R$^3$, R$^4$, R$^5$, R$^6$, R$^7$ and R$^8$ each independently represent a hydrogen atom, a halogen atom, an alkyl group, an alkyloxy group, an alkylthio group, an aryl group, an aryloxy group, an arylthio group, an arylalkyl group, an arylalkyloxy group, an arylalkylthio group, an acyl group, an acyloxy group, an amide group, an acid imide group, an imine residue, an amino group, a substituted amino group, a substituted silyl group, a substituted silyloxy group, a substituted silylthio group, a substituted silylamino group, a mono-valent heterocyclic group, a heteroaryloxy group, a heteroarylthio group, an arylalkenyl group, an arylethynyl group, a carboxyl group, an alkyloxycarbonyl group, an aryloxycarbonyl group, an arylalkyloxycarbonyl group, a heteroaryloxycarbonyl group or a cyano group, wherein R$^1$, R$^2$, R$^3$ and R$^4$ may be mutually connected to form a ring, and wherein the compound represented by formula (6-1) may have a substituent on the benzene ring in the compound, and substituents may be mutually connected to form a ring.

* * * * *